(12) United States Patent
McClain et al.

(10) Patent No.: US 11,369,498 B2
(45) Date of Patent: Jun. 28, 2022

(54) STENT AND STENT DELIVERY SYSTEM WITH IMPROVED DELIVERABILITY

(75) Inventors: James B. McClain, Raleigh, NC (US);
Douglas Taylor, Franklinton, NC (US);
David Enscore, Alpharetta, GA (US)

(73) Assignee: MT Acquisition Holdings LLC, Pine Plains, NY (US)

( * ) Notice: Subject to any disclaimer, the term of this patent is extended or adjusted under 35 U.S.C. 154(b) by 68 days.

(21) Appl. No.: 13/014,632

(22) Filed: Jan. 26, 2011

(65) Prior Publication Data

US 2011/0190864 A1     Aug. 4, 2011

Related U.S. Application Data

(60) Provisional application No. 61/300,764, filed on Feb. 2, 2010.

(51) Int. Cl.
*A61F 2/958*     (2013.01)
*A61F 2/00*     (2006.01)
*A61F 2/82*     (2013.01)

(52) U.S. Cl.
CPC .............. *A61F 2/958* (2013.01); *A61F 2/0077* (2013.01); *A61F 2002/826* (2013.01); *A61F 2250/003* (2013.01)

(58) Field of Classification Search
CPC ...... A61F 2/82; A61F 2/95; A61F 2210/0076; A61F 2250/0014; A61F 2250/0018;
(Continued)

(56) References Cited

U.S. PATENT DOCUMENTS 3,087,660 A    4/1963    Endicott
3,087,860 A    4/1963    Endicott
(Continued)

FOREIGN PATENT DOCUMENTS

CA    2237466 A1    11/1998
CA    2589761       12/2004
(Continued)

OTHER PUBLICATIONS

Ong and Serruys, "Technology Insight: an overview of research in drug-eluting stents," Nat. Clin. Parct. Cardiovas. Med. 2(12):647-658 (2005).
(Continued)

*Primary Examiner* — Darwin P Erezo
*Assistant Examiner* — Erin L Colello
(74) *Attorney, Agent, or Firm* — Joseph Hajjar

(57) ABSTRACT

Stent delivery systems having improved deliverability comprising an elongate member having an inflation lumen and a guidewire lumen therein; a balloon having an interior that is in fluid communication with the inflation lumen; and a stent comprising a coating mounted on the balloon. Methods for making stent delivery systems having improved deliverability. Methods for delivering two stent delivery systems concurrently through a guiding catheter, each stent delivery system comprising elongate member having an inflation lumen and a guidewire lumen therein, a balloon having an interior that is in fluid communication with the inflation lumen, and a stent comprising a coating mounted on the balloon. Stent coatings may comprise a pharmaceutical agent at least a portion of which is in crystalline form.

16 Claims, 2 Drawing Sheets

(58) Field of Classification Search
CPC ...... A61F 2250/0019; A61F 2250/0021; A61F 2250/0029; A61F 2250/0036; A61F 2310/00389; A61F 2250/0009; A61F 2002/3006; A61F 2002/3007; A61F 2002/30072; A61M 2025/0062; A61M 2025/0063; A61M 25/0045; A61M 2025/0046; A61M 25/0053; A61L 31/08; A61L 31/082
USPC .......... 623/1.11, 1.15, 1.42, 1.43, 1.44, 1.45, 623/1.46
See application file for complete search history.

(56) References Cited

U.S. PATENT DOCUMENTS

| | | |
|---|---|---|
| 3,123,077 A | 3/1964 | Alcamo |
| 3,457,280 A | 7/1969 | Schmitt et al. |
| 3,597,449 A | 8/1971 | Deprospero et al. |
| 3,737,337 A | 6/1973 | Schnoring et al. |
| 3,773,919 A | 11/1973 | Boswell et al. |
| 3,929,992 A | 12/1975 | Sehgal et al. |
| 4,000,137 A | 12/1976 | Dvonch et al. |
| 4,188,373 A | 2/1980 | Krezanoski |
| 4,285,987 A | 8/1981 | Ayer et al. |
| 4,326,532 A | 4/1982 | Hammar |
| 4,336,381 A | 6/1982 | Nagata et al. |
| 4,389,330 A | 6/1983 | Tice et al. |
| 4,474,572 A | 10/1984 | McNaughton et al. |
| 4,474,751 A | 10/1984 | Haslam et al. |
| 4,478,822 A | 10/1984 | Haslam et al. |
| 4,530,840 A | 7/1985 | Tice et al. |
| 4,582,731 A | 4/1986 | Smith |
| 4,606,347 A | 8/1986 | Fogarty et al. |
| 4,617,751 A | 10/1986 | Johansson |
| 4,655,771 A | 4/1987 | Wallsten |
| 4,675,189 A | 6/1987 | Kent et al. |
| 4,733,665 A | 3/1988 | Palmaz |
| 4,734,227 A | 3/1988 | Smith |
| 4,734,451 A | 3/1988 | Smith |
| 4,758,435 A | 7/1988 | Schaaf |
| 4,762,593 A | 8/1988 | Youngner |
| 4,931,037 A | 6/1990 | Wetterman |
| 4,950,239 A | 8/1990 | Gahara |
| 4,985,625 A | 1/1991 | Hurst |
| 5,000,519 A | 3/1991 | Moore |
| 5,090,419 A | 2/1992 | Palestrant |
| 5,096,848 A | 3/1992 | Kawamura |
| 5,102,417 A | 4/1992 | Palmaz |
| 5,104,404 A | 4/1992 | Wolff |
| 5,106,650 A | 4/1992 | Hoy et al. |
| 5,125,570 A | 6/1992 | Jones |
| 5,158,986 A | 10/1992 | Cha et al. |
| 5,185,776 A | 2/1993 | Townsend |
| 5,195,969 A | 3/1993 | Wang et al. |
| 5,243,023 A | 9/1993 | Dezern |
| 5,270,086 A | 12/1993 | Hamlin |
| 5,272,012 A * | 12/1993 | Opolski ............... A61L 29/085 427/2.1 |
| 5,288,711 A | 2/1994 | Mitchell et al. |
| 5,320,634 A | 6/1994 | Vigil et al. |
| 5,324,049 A | 6/1994 | Mistrater et al. |
| 5,340,614 A | 8/1994 | Perman et al. |
| 5,342,621 A | 8/1994 | Eury |
| 5,350,361 A | 9/1994 | Tsukashima et al. |
| 5,350,627 A | 9/1994 | Nemphos et al. |
| 5,356,433 A | 10/1994 | Rowland et al. |
| 5,360,403 A | 11/1994 | Mische |
| 5,362,718 A | 11/1994 | Skotnicki et al. |
| 5,366,504 A | 11/1994 | Andersen et al. |
| 5,368,045 A | 11/1994 | Clement et al. |
| 5,372,676 A | 12/1994 | Lowe |
| 5,385,776 A | 1/1995 | Maxfield et al. |
| 5,387,313 A | 2/1995 | Thoms |
| 5,403,347 A | 4/1995 | Roby et al. |
| 5,470,603 A | 11/1995 | Staniforth et al. |
| 5,494,620 A | 2/1996 | Liu et al. |
| 5,500,180 A | 3/1996 | Anderson et al. |
| 5,514,379 A | 5/1996 | Weissleder et al. |
| 5,545,208 A | 8/1996 | Wolff et al. |
| 5,556,383 A | 9/1996 | Wang et al. |
| 5,562,922 A | 10/1996 | Lambert |
| 5,569,463 A | 10/1996 | Helmus et al. |
| 5,570,537 A | 11/1996 | Black et al. |
| 5,578,709 A | 11/1996 | Woiszwillo |
| 5,599,576 A * | 2/1997 | Opolski ................... 427/2.3 |
| 5,605,696 A | 2/1997 | Eury et al. |
| 5,607,442 A | 3/1997 | Fischell et al. |
| 5,609,629 A | 3/1997 | Fearnot et al. |
| 5,626,611 A | 5/1997 | Liu et al. |
| 5,626,862 A | 5/1997 | Brem et al. |
| 5,632,772 A | 5/1997 | Alcime et al. |
| 5,669,932 A | 9/1997 | Fischell et al. |
| 5,674,192 A * | 10/1997 | Sahatjian ................ A61F 2/90 604/28 |
| 5,674,242 A | 10/1997 | Phan et al. |
| 5,674,286 A | 10/1997 | D'Alessio et al. |
| 5,725,570 A | 3/1998 | Heath |
| 5,733,303 A | 3/1998 | Israel et al. |
| 5,766,158 A | 6/1998 | Opolski |
| 5,800,511 A | 9/1998 | Mayer |
| 5,807,404 A | 9/1998 | Richter |
| 5,811,032 A | 9/1998 | Kawai et al. |
| 5,824,049 A | 10/1998 | Ragheb et al. |
| 5,837,313 A | 11/1998 | Ding et al. |
| 5,843,120 A | 12/1998 | Israel et al. |
| 5,871,436 A | 2/1999 | Eury |
| 5,873,904 A | 2/1999 | Ragheb et al. |
| 5,876,426 A | 3/1999 | Kume et al. |
| 5,876,452 A | 3/1999 | Athanasiou et al. |
| 5,913,895 A | 6/1999 | Burpee et al. |
| 5,924,631 A | 7/1999 | Rodrigues et al. |
| 5,948,020 A | 9/1999 | Yoon et al. |
| 5,957,975 A | 9/1999 | Lafont et al. |
| 5,981,568 A | 11/1999 | Kunz et al. |
| 5,981,719 A | 11/1999 | Woiszwillo et al. |
| 6,013,855 A | 1/2000 | McPherson et al. |
| 6,036,978 A | 3/2000 | Gombotz et al. |
| 6,039,721 A | 3/2000 | Johnson et al. |
| 6,068,656 A | 5/2000 | Von Oepen |
| 6,071,308 A | 6/2000 | Ballou et al. |
| 6,077,880 A | 6/2000 | Castillo et al. |
| 6,090,925 A | 7/2000 | Woiszwillo et al. |
| 6,129,755 A | 10/2000 | Mathis et al. |
| 6,143,037 A | 11/2000 | Goldsten et al. |
| 6,143,314 A | 11/2000 | Chandrashekar et al. |
| 6,146,356 A | 11/2000 | Wang et al. |
| 6,146,404 A | 11/2000 | Kim et al. |
| 6,147,135 A | 11/2000 | Yuan et al. |
| 6,153,252 A | 11/2000 | Hossainy et al. |
| 6,171,327 B1 | 1/2001 | Daniel et al. |
| 6,190,699 B1 | 2/2001 | Luzzi et al. |
| 6,193,744 B1 | 2/2001 | Ehr et al. |
| 6,206,914 B1 | 3/2001 | Soykan et al. |
| 6,217,608 B1 * | 4/2001 | Penn ...................... A61F 2/82 623/1.15 |
| 6,231,599 B1 | 5/2001 | Ley |
| 6,231,600 B1 | 5/2001 | Zhong et al. |
| 6,245,104 B1 | 6/2001 | Alt |
| 6,248,127 B1 | 6/2001 | Shah et al. |
| 6,248,129 B1 | 6/2001 | Froix |
| 6,251,980 B1 | 6/2001 | Lan et al. |
| 6,268,053 B1 | 7/2001 | Woiszwillo et al. |
| 6,273,913 B1 | 8/2001 | Wright et al. |
| 6,284,758 B1 | 9/2001 | Egi et al. |
| 6,299,635 B1 | 10/2001 | Frantzen |
| 6,309,669 B1 | 10/2001 | Setterstrom et al. |
| 6,319,541 B1 | 11/2001 | Pletcher et al. |
| 6,325,821 B1 | 12/2001 | Gaschino et al. |
| 6,336,934 B1 | 1/2002 | Gilson et al. |
| 6,342,062 B1 | 1/2002 | Suon et al. |
| 6,344,055 B1 * | 2/2002 | Shukov ................... A61F 2/91 29/896.6 |
| 6,355,691 B1 | 3/2002 | Goodman |

(56) References Cited

U.S. PATENT DOCUMENTS

| | | |
|---|---|---|
| 6,358,556 B1 | 3/2002 | Ding et al. |
| 6,361,819 B1 | 3/2002 | Tedeschi et al. |
| 6,362,718 B1 | 3/2002 | Patrick et al. |
| 6,364,903 B2 | 4/2002 | Tseng et al. |
| 6,368,658 B1 | 4/2002 | Schwartz et al. |
| 6,372,246 B1 | 4/2002 | Wei et al. |
| 6,387,121 B1 | 5/2002 | Alt |
| 6,409,716 B1 | 6/2002 | Sahatjian et al. |
| 6,414,050 B1 | 7/2002 | Howdle et al. |
| 6,416,779 B1 | 7/2002 | D-Augustine et al. |
| 6,448,315 B1 | 9/2002 | Lidgren et al. |
| 6,458,387 B1 | 10/2002 | Scott et al. |
| 6,461,380 B1 | 10/2002 | Cox |
| 6,461,644 B1 | 10/2002 | Jackson et al. |
| 6,488,703 B1 | 12/2002 | Kveen et al. |
| 6,495,163 B1 | 12/2002 | Jordan |
| 6,497,729 B1 | 12/2002 | Moussy et al. |
| 6,506,213 B1 | 1/2003 | Mandel et al. |
| 6,511,748 B1 | 1/2003 | Barrows |
| 6,517,860 B1 | 2/2003 | Rosser et al. |
| 6,521,258 B1 | 2/2003 | Mandel et al. |
| 6,524,698 B1 | 2/2003 | Schmoock |
| 6,530,951 B1 | 3/2003 | Bates et al. |
| 6,537,310 B1 | 3/2003 | Palmaz et al. |
| 6,541,033 B1 | 4/2003 | Shah |
| 6,572,813 B1 | 6/2003 | Zhang et al. |
| 6,602,281 B1 | 8/2003 | Klein |
| 6,605,696 B1 | 8/2003 | Rosey |
| 6,610,013 B1 | 8/2003 | Fenster et al. |
| 6,627,246 B2 | 9/2003 | Mehta et al. |
| 6,649,627 B1 | 11/2003 | Cecchi et al. |
| 6,660,176 B2 | 12/2003 | Tepper et al. |
| 6,669,785 B2 | 12/2003 | DeYoung et al. |
| 6,669,980 B2 | 12/2003 | Hanson et al. |
| 6,670,407 B2 | 12/2003 | Howdle et al. |
| 6,673,053 B2 * | 1/2004 | Wang .................. A61L 29/085 604/172 |
| 6,682,757 B1 | 1/2004 | Wright |
| 6,706,283 B1 | 3/2004 | Appel et al. |
| 6,710,059 B1 | 3/2004 | Fernand et al. |
| 6,720,003 B2 | 4/2004 | Cheng et al. |
| 6,723,913 B1 | 4/2004 | Barbetta |
| 6,726,712 B1 | 4/2004 | Raeder-Devens et al. |
| 6,736,996 B1 | 5/2004 | Carbonell et al. |
| 6,743,505 B2 | 6/2004 | Antall et al. |
| 6,749,902 B2 | 6/2004 | Yonker et al. |
| 6,755,871 B2 | 6/2004 | Damaso et al. |
| 6,756,084 B2 | 6/2004 | Fulton et al. |
| 6,767,558 B2 | 7/2004 | Wang et al. |
| 6,780,475 B2 | 8/2004 | Fulton et al. |
| 6,794,902 B2 | 9/2004 | Becker et al. |
| 6,800,663 B2 | 10/2004 | Asgarzadeh et al. |
| 6,815,218 B1 | 11/2004 | Jacobsen et al. |
| 6,821,549 B2 | 11/2004 | Jayaraman |
| 6,837,611 B2 | 1/2005 | Kuo et al. |
| 6,838,089 B1 | 1/2005 | Carlsson et al. |
| 6,838,528 B2 | 1/2005 | Zhou |
| 6,858,598 B1 | 2/2005 | McKearn et al. |
| 6,868,123 B2 | 3/2005 | Bellas et al. |
| 6,884,377 B1 | 4/2005 | Burnham et al. |
| 6,897,205 B2 | 5/2005 | Beckert et al. |
| 6,884,823 B1 | 6/2005 | Plerick et al. |
| 6,905,555 B2 | 6/2005 | DeYoung et al. |
| 6,908,624 B2 | 6/2005 | Hossainy et al. |
| 6,916,800 B2 | 7/2005 | McKearn et al. |
| 6,923,979 B2 | 8/2005 | Fotland et al. |
| 6,936,270 B2 | 8/2005 | Watson et al. |
| 6,939,569 B1 | 9/2005 | Green et al. |
| 6,973,718 B2 | 12/2005 | Sheppard et al. |
| 7,056,591 B1 | 6/2006 | Pacetti et al. |
| 7,094,256 B1 | 8/2006 | Shah et al. |
| 7,148,201 B2 | 12/2006 | Stern et al. |
| 7,152,452 B2 | 12/2006 | Kokish |
| 7,160,592 B2 | 1/2007 | Rypacek et al. |
| 7,163,715 B1 | 1/2007 | Kramer |
| 7,169,404 B2 | 1/2007 | Hossainy et al. |
| 7,171,255 B2 | 1/2007 | Holupka et al. |
| 7,201,750 B1 | 4/2007 | Eggers et al. |
| 7,201,940 B1 | 4/2007 | Kramer |
| 7,229,837 B2 | 6/2007 | Chen |
| 7,278,174 B2 | 10/2007 | Villalobos |
| 7,282,020 B2 | 10/2007 | Kaplan |
| 7,308,748 B2 | 12/2007 | Kokish |
| 7,323,454 B2 | 1/2008 | De Nijs et al. |
| 7,326,734 B2 | 2/2008 | Zi et al. |
| 7,329,383 B2 | 2/2008 | Stinson |
| 7,378,105 B2 | 5/2008 | Burke et al. |
| 7,419,696 B2 | 9/2008 | Berg et al. |
| 7,429,378 B2 | 9/2008 | Serhan et al. |
| 7,444,162 B2 | 10/2008 | Hassan |
| 7,455,658 B2 | 11/2008 | Wang |
| 7,456,151 B2 | 11/2008 | Li et al. |
| 7,462,593 B2 | 12/2008 | Cuttitta et al. |
| 7,470,281 B2 * | 12/2008 | Tedeschi .................. A61F 2/90 623/1.11 |
| 7,485,113 B2 | 2/2009 | Varner et al. |
| 7,498,042 B2 | 3/2009 | Igaki et al. |
| 7,524,865 B2 | 4/2009 | D'Amato et al. |
| 7,527,632 B2 * | 5/2009 | Houghton ............... A61F 2/958 606/108 |
| 7,537,610 B2 | 5/2009 | Reiss |
| 7,537,785 B2 | 5/2009 | Loscalzo et al. |
| 7,544,381 B2 * | 6/2009 | Kangas ................. A61L 29/085 427/2.1 |
| 7,553,827 B2 | 6/2009 | Attawia et al. |
| 7,713,538 B2 | 5/2010 | Lewis et al. |
| 7,727,275 B2 * | 6/2010 | Betts et al. .................. 623/1.46 |
| 7,745,566 B2 | 6/2010 | Chattopadhyay et al. |
| 7,763,277 B1 | 7/2010 | Canham et al. |
| 7,771,468 B2 | 8/2010 | Whitbourne et al. |
| 7,837,726 B2 | 11/2010 | Von Oepen et al. |
| 7,842,312 B2 | 11/2010 | Burgermeister et al. |
| 7,919,108 B2 | 4/2011 | Rees et al. |
| 7,955,383 B2 | 6/2011 | Krivoruchko et al. |
| 7,967,855 B2 * | 6/2011 | Furst ........................ A61F 2/91 606/198 |
| 7,972,661 B2 | 7/2011 | Pui et al. |
| 8,070,796 B2 | 12/2011 | Furst et al. |
| 8,109,904 B1 | 2/2012 | Papp |
| 8,298,565 B2 * | 10/2012 | Taylor et al. ................. 424/423 |
| 8,333,803 B2 | 12/2012 | Park et al. |
| 8,377,356 B2 | 2/2013 | Huang |
| 8,535,372 B1 | 9/2013 | Fox et al. |
| 8,709,071 B1 | 4/2014 | Huang et al. |
| 8,753,659 B2 | 6/2014 | Lewis et al. |
| 8,753,709 B2 | 6/2014 | Hossainy et al. |
| 8,758,429 B2 | 6/2014 | Taylor et al. |
| 8,795,762 B2 | 8/2014 | Fulton et al. |
| 8,834,913 B2 | 9/2014 | Shaw et al. |
| 8,852,625 B2 * | 10/2014 | DeYoung et al. ............. 424/426 |
| 8,900,651 B2 | 12/2014 | McClain et al. |
| 9,090,029 B2 | 7/2015 | Prevost |
| 9,433,516 B2 | 9/2016 | McClain et al. |
| 9,486,431 B2 | 11/2016 | McClain et al. |
| 10,117,972 B2 | 11/2018 | McClain et al. |
| 2001/0026804 A1 | 10/2001 | Boutignon |
| 2001/0027299 A1 * | 10/2001 | Yang .................... A61L 29/085 604/265 |
| 2001/0034336 A1 | 10/2001 | Shah et al. |
| 2001/0037143 A1 | 11/2001 | Oepen |
| 2001/0044629 A1 * | 11/2001 | Stinson ........................ 606/108 |
| 2001/0049551 A1 | 12/2001 | Tseng et al. |
| 2002/0002353 A1 * | 1/2002 | Michal .................... C08L 89/00 604/265 |
| 2002/0007209 A1 | 1/2002 | Scheerder et al. |
| 2002/0051485 A1 | 5/2002 | Bottomley |
| 2002/0051845 A1 | 5/2002 | Bottomley |
| 2002/0082679 A1 | 6/2002 | Sirhan et al. |
| 2002/0082680 A1 * | 6/2002 | Shanley et al. ................. 623/1.16 |
| 2002/0091433 A1 | 7/2002 | Ding et al. |
| 2002/0099332 A1 | 7/2002 | Slepian et al. |
| 2002/0125860 A1 | 9/2002 | Schworn et al. |
| 2002/0133072 A1 | 9/2002 | Wang et al. |
| 2002/0144757 A1 | 10/2002 | Craig et al. |

(56) References Cited

U.S. PATENT DOCUMENTS

| | | |
|---|---|---|
| 2002/0151959 A1 | 10/2002 | Von Oepen |
| 2003/0001830 A1 | 1/2003 | Wampler et al. |
| 2003/0004563 A1 | 1/2003 | Jackson et al. |
| 2003/0028244 A1 | 2/2003 | Bates et al. |
| 2003/0031699 A1 | 2/2003 | Van Antwerp |
| 2003/0077200 A1 | 4/2003 | Charles et al. |
| 2003/0088307 A1 | 5/2003 | Shulze et al. |
| 2003/0125800 A1 | 7/2003 | Shulze et al. |
| 2003/0143315 A1 | 7/2003 | Pui et al. |
| 2003/0170305 A1 | 9/2003 | O'Neil et al. |
| 2003/0180376 A1 | 9/2003 | Dalal et al. |
| 2003/0185964 A1 | 10/2003 | Weber et al. |
| 2003/0204238 A1* | 10/2003 | Tedeschi .............. A61F 2/90 623/1.11 |
| 2003/0209835 A1 | 11/2003 | Chun et al. |
| 2003/0222017 A1* | 12/2003 | Fulton et al. ............. 210/634 |
| 2003/0222018 A1 | 12/2003 | Yonker et al. |
| 2003/0232014 A1 | 12/2003 | Burke et al. |
| 2004/0013792 A1 | 1/2004 | Epstein et al. |
| 2004/0018228 A1* | 1/2004 | Fischell et al. ............ 424/450 |
| 2004/0022400 A1 | 2/2004 | Magrath |
| 2004/0022853 A1* | 2/2004 | Ashton et al. ............. 424/468 |
| 2004/0044397 A1 | 3/2004 | Stinson |
| 2004/0059290 A1 | 3/2004 | Palasis et al. |
| 2004/0096477 A1 | 5/2004 | Chauhan et al. |
| 2004/0102758 A1* | 5/2004 | Davila .............. A61B 17/0644 604/500 |
| 2004/0106982 A1 | 6/2004 | Jalisi |
| 2004/0122205 A1 | 6/2004 | Nathan |
| 2004/0126542 A1 | 7/2004 | Fujiwara et al. |
| 2004/0143317 A1 | 7/2004 | Takashi et al. |
| 2004/0144317 A1 | 7/2004 | Chuman et al. |
| 2004/0147904 A1 | 7/2004 | Hung et al. |
| 2004/0157789 A1 | 8/2004 | Geall |
| 2004/0170685 A1 | 9/2004 | Carpenter et al. |
| 2004/0193177 A1* | 9/2004 | Houghton .............. A61F 2/958 606/108 |
| 2004/0193262 A1 | 9/2004 | Shadduck |
| 2004/0220660 A1 | 11/2004 | Shanley et al. |
| 2004/0224001 A1 | 11/2004 | Pacetti et al. |
| 2004/0234748 A1 | 11/2004 | Stenzel |
| 2004/0236416 A1 | 11/2004 | Falotico |
| 2004/0260000 A1 | 12/2004 | Chaiko |
| 2004/0267345 A1* | 12/2004 | Lorenzo .............. A61F 2/958 623/1.11 |
| 2005/0003074 A1 | 1/2005 | Brown et al. |
| 2005/0004661 A1 | 1/2005 | Lewis et al. |
| 2005/0004663 A1* | 1/2005 | Llanos .............. A61B 17/0644 623/1.46 |
| 2005/0010275 A1 | 1/2005 | Sahatjian et al. |
| 2005/0015046 A1 | 1/2005 | Weber et al. |
| 2005/0019747 A1 | 1/2005 | Anderson et al. |
| 2005/0033414 A1 | 2/2005 | Zhang et al. |
| 2005/0033417 A1* | 2/2005 | Borges .............. A61K 9/0024 623/1.46 |
| 2005/0038498 A1 | 2/2005 | Dubrow et al. |
| 2005/0048121 A1 | 3/2005 | East et al. |
| 2005/0049694 A1 | 3/2005 | Neary |
| 2005/0053639 A1 | 3/2005 | Shalaby |
| 2005/0060028 A1 | 3/2005 | Horres et al. |
| 2005/0069630 A1 | 3/2005 | Fox et al. |
| 2005/0070989 A1 | 3/2005 | Lye et al. |
| 2005/0070990 A1 | 3/2005 | Stinson |
| 2005/0070997 A1 | 3/2005 | Thornton et al. |
| 2005/0074479 A1 | 4/2005 | Weber et al. |
| 2005/0075714 A1 | 4/2005 | Cheng et al. |
| 2005/0079199 A1 | 4/2005 | Heruth et al. |
| 2005/0079274 A1 | 4/2005 | Palasis et al. |
| 2005/0084533 A1 | 4/2005 | Howdle et al. |
| 2005/0095267 A1 | 5/2005 | Campbell et al. |
| 2005/0131008 A1 | 6/2005 | Betts et al. |
| 2005/0131513 A1 | 6/2005 | Myers et al. |
| 2005/0147734 A1 | 7/2005 | Seppala et al. |
| 2005/0159704 A1 | 7/2005 | Scott et al. |
| 2005/0166841 A1 | 8/2005 | Robida |
| 2005/0170071 A1* | 8/2005 | Eramo .............. A61L 29/085 427/2.1 |
| 2005/0175772 A1 | 8/2005 | Worsham et al. |
| 2005/0177223 A1 | 8/2005 | Palmaz |
| 2005/0191491 A1 | 9/2005 | Wang et al. |
| 2005/0196424 A1 | 9/2005 | Chappa |
| 2005/0208102 A1 | 9/2005 | Schultz |
| 2005/0209244 A1* | 9/2005 | Prescott .............. A61K 31/502 514/252.18 |
| 2005/0209680 A1 | 9/2005 | Gale et al. |
| 2005/0216075 A1 | 9/2005 | Wang et al. |
| 2005/0220839 A1* | 10/2005 | DeWitt .............. A61L 29/085 424/423 |
| 2005/0222676 A1 | 10/2005 | Shanley et al. |
| 2005/0238829 A1 | 10/2005 | Motherwell et al. |
| 2005/0245637 A1 | 11/2005 | Hossainy et al. |
| 2005/0255327 A1 | 11/2005 | Chaney |
| 2005/0260186 A1 | 11/2005 | Bookbinder et al. |
| 2005/0268573 A1 | 12/2005 | Maxfield et al. |
| 2005/0288481 A1 | 12/2005 | Desnoyer et al. |
| 2005/0288629 A1 | 12/2005 | Kunis |
| 2006/0001011 A1 | 1/2006 | Wilson et al. |
| 2006/0002974 A1 | 1/2006 | Pacetti et al. |
| 2006/0020325 A1 | 1/2006 | Burgermeister et al. |
| 2006/0030652 A1 | 2/2006 | Adams et al. |
| 2006/0045901 A1 | 3/2006 | Weber et al. |
| 2006/0067974 A1 | 3/2006 | Labrecque et al. |
| 2006/0073329 A1 | 4/2006 | Boyce et al. |
| 2006/0089705 A1 | 4/2006 | Ding et al. |
| 2006/0093771 A1 | 5/2006 | Rypacek et al. |
| 2006/0094744 A1 | 5/2006 | Maryanoff et al. |
| 2006/0104969 A1 | 5/2006 | Oray et al. |
| 2006/0106455 A1 | 5/2006 | Furst et al. |
| 2006/0116755 A1 | 6/2006 | Stinson |
| 2006/0121080 A1 | 6/2006 | Lye et al. |
| 2006/0121089 A1 | 6/2006 | Michal et al. |
| 2006/0134168 A1 | 6/2006 | Chappa et al. |
| 2006/0134211 A1 | 6/2006 | Lien et al. |
| 2006/0136041 A1 | 6/2006 | Schmid et al. |
| 2006/0147698 A1 | 7/2006 | Carroll et al. |
| 2006/0153729 A1 | 7/2006 | Stinson |
| 2006/0160455 A1 | 7/2006 | Sugyo et al. |
| 2006/0188547 A1 | 8/2006 | Bezwada |
| 2006/0193886 A1 | 8/2006 | Owens et al. |
| 2006/0193890 A1 | 8/2006 | Owens |
| 2006/0198868 A1 | 9/2006 | Dewitt et al. |
| 2006/0210638 A1 | 9/2006 | Liversidge et al. |
| 2006/0216324 A1 | 9/2006 | Stucke et al. |
| 2006/0222756 A1 | 10/2006 | Davila et al. |
| 2006/0228415 A1 | 10/2006 | Oberegger et al. |
| 2006/0228453 A1 | 10/2006 | Cromack et al. |
| 2006/0235506 A1 | 10/2006 | Ta et al. |
| 2006/0276877 A1 | 12/2006 | Owens et al. |
| 2006/0287611 A1 | 12/2006 | Fleming |
| 2007/0009564 A1 | 1/2007 | McClain et al. |
| 2007/0009664 A1 | 1/2007 | Fallais et al. |
| 2007/0026041 A1 | 2/2007 | DesNoyer et al. |
| 2007/0026042 A1* | 2/2007 | Narayanan .............. A61L 17/005 424/426 |
| 2007/0032864 A1* | 2/2007 | Furst .............. A61L 31/06 623/1.42 |
| 2007/0038227 A1 | 2/2007 | Massicotte et al. |
| 2007/0038289 A1 | 2/2007 | Nishide et al. |
| 2007/0043434 A1 | 2/2007 | Meerkin et al. |
| 2007/0059350 A1 | 3/2007 | Kennedy et al. |
| 2007/0065478 A1 | 3/2007 | Hossainy |
| 2007/0110888 A1 | 5/2007 | Radhakrishnan et al. |
| 2007/0123973 A1* | 5/2007 | Roth .............. A61F 2/91 623/1.15 |
| 2007/0123977 A1 | 5/2007 | Cottone et al. |
| 2007/0128274 A1 | 6/2007 | Zhu et al. |
| 2007/0148251 A1 | 6/2007 | Hossainy et al. |
| 2007/0154513 A1 | 7/2007 | Atanasoska et al. |
| 2007/0154554 A1 | 7/2007 | Burgermeister et al. |
| 2007/0196242 A1 | 8/2007 | Boozer et al. |
| 2007/0196423 A1 | 8/2007 | Ruane et al. |
| 2007/0198081 A1 | 8/2007 | Castro et al. |
| 2007/0200268 A1 | 8/2007 | Dave |

(56) References Cited

U.S. PATENT DOCUMENTS

| | | |
|---|---|---|
| 2007/0203569 A1 | 8/2007 | Burgermeister et al. |
| 2007/0219579 A1 | 9/2007 | Paul |
| 2007/0225795 A1 | 9/2007 | Granada et al. |
| 2007/0250157 A1 | 10/2007 | Nishide et al. |
| 2007/0259017 A1 | 11/2007 | Francis |
| 2007/0280992 A1 | 12/2007 | Margaron et al. |
| 2008/0030066 A1 | 2/2008 | Mercier et al. |
| 2008/0051866 A1 | 2/2008 | Chen et al. |
| 2008/0065192 A1 | 3/2008 | Berglund |
| 2008/0071347 A1 | 3/2008 | Cambronne |
| 2008/0071358 A1* | 3/2008 | Weber et al. ............... 623/1.42 |
| 2008/0071359 A1 | 3/2008 | Thornton et al. |
| 2008/0075753 A1 | 3/2008 | Chappa |
| 2008/0077232 A1 | 3/2008 | Nishide |
| 2008/0085880 A1 | 4/2008 | Viswanath et al. |
| 2008/0091008 A1 | 4/2008 | Viswanath et al. |
| 2008/0095919 A1 | 4/2008 | McClain et al. |
| 2008/0097575 A1 | 4/2008 | Cottone |
| 2008/0097591 A1 | 4/2008 | Savage et al. |
| 2008/0098178 A1 | 4/2008 | Veazey et al. |
| 2008/0107702 A1 | 5/2008 | Jennissen |
| 2008/0118543 A1 | 5/2008 | Pacetti et al. |
| 2008/0118544 A1 | 5/2008 | Wang |
| 2008/0124372 A1 | 5/2008 | Hossainy et al. |
| 2008/0138375 A1 | 6/2008 | Yan et al. |
| 2008/0206304 A1 | 8/2008 | Lindquist et al. |
| 2008/0213464 A1 | 9/2008 | O'Connor |
| 2008/0233267 A1 | 9/2008 | Berglund |
| 2008/0255510 A1 | 10/2008 | Wang |
| 2008/0269449 A1 | 10/2008 | Chattopadhyay et al. |
| 2008/0286325 A1 | 11/2008 | Reyes et al. |
| 2008/0292776 A1* | 11/2008 | Dias ..................... A61L 29/085 427/2.24 |
| 2008/0300669 A1 | 12/2008 | Hossainy |
| 2008/0300689 A1 | 12/2008 | Hossainy |
| 2009/0011116 A1* | 1/2009 | Herweck ................ A61F 2/86 427/2.1 |
| 2009/0043379 A1 | 2/2009 | Prescott |
| 2009/0062909 A1* | 3/2009 | Taylor et al. ............... 623/1.42 |
| 2009/0068266 A1 | 3/2009 | Raheja et al. |
| 2009/0076446 A1 | 3/2009 | Dubuclet et al. |
| 2009/0082855 A1* | 3/2009 | Borges ................... A61K 9/0024 623/1.42 |
| 2009/0098178 A1 | 4/2009 | Hofmann et al. |
| 2009/0105687 A1 | 4/2009 | Deckman et al. |
| 2009/0105809 A1* | 4/2009 | Lee ..................... A61F 2/91 623/1.17 |
| 2009/0110711 A1 | 4/2009 | Trollsas et al. |
| 2009/0111787 A1 | 4/2009 | Lim et al. |
| 2009/0123515 A1 | 5/2009 | Taylor et al. |
| 2009/0123521 A1 | 5/2009 | Weber et al. |
| 2009/0186069 A1 | 7/2009 | DeYoung et al. |
| 2009/0202609 A1 | 8/2009 | Keough et al. |
| 2009/0216317 A1 | 8/2009 | Cromack et al. |
| 2009/0227949 A1 | 9/2009 | Freyman et al. |
| 2009/0231578 A1 | 9/2009 | Ling et al. |
| 2009/0263460 A1 | 10/2009 | McDonald |
| 2009/0285974 A1 | 11/2009 | Kerrigan |
| 2009/0292351 A1 | 11/2009 | McClain et al. |
| 2009/0292776 A1 | 11/2009 | Nesbitt et al. |
| 2009/0297578 A1 | 12/2009 | Trollsas et al. |
| 2009/0300689 A1 | 12/2009 | Conte et al. |
| 2010/0000328 A1 | 1/2010 | Mahmoud |
| 2010/0006358 A1 | 1/2010 | Ishikawa |
| 2010/0015200 A1 | 1/2010 | McClain et al. |
| 2010/0030261 A1 | 2/2010 | McClain et al. |
| 2010/0042206 A1* | 2/2010 | Yadav ................... A61F 2/91 623/1.42 |
| 2010/0055145 A1* | 3/2010 | Betts ................... A61L 31/10 424/423 |
| 2010/0055294 A1* | 3/2010 | Wang et al. ............... 427/2.25 |
| 2010/0063570 A1 | 3/2010 | Pacetti et al. |
| 2010/0063580 A1 | 3/2010 | McClain et al. |
| 2010/0074934 A1 | 3/2010 | Hunter |
| 2010/0131044 A1* | 5/2010 | Patel ..................... A61F 2/915 623/1.16 |
| 2010/0155496 A1 | 6/2010 | Stark et al. |
| 2010/0166869 A1 | 7/2010 | Desai et al. |
| 2010/0196482 A1 | 8/2010 | Radovic-Moreno et al. |
| 2010/0198330 A1 | 8/2010 | Hossainy et al. |
| 2010/0198331 A1 | 8/2010 | Rapoza et al. |
| 2010/0211164 A1 | 8/2010 | McClain et al. |
| 2010/0228348 A1 | 9/2010 | McClain et al. |
| 2010/0233332 A1 | 9/2010 | Xing et al. |
| 2010/0239635 A1 | 9/2010 | McClain et al. |
| 2010/0241220 A1 | 9/2010 | McClain et al. |
| 2010/0256746 A1 | 10/2010 | Taylor et al. |
| 2010/0256748 A1 | 10/2010 | Taylor et al. |
| 2010/0262224 A1 | 10/2010 | Kleiner |
| 2010/0272775 A1 | 10/2010 | Cleek et al. |
| 2010/0272778 A1 | 10/2010 | McClain et al. |
| 2010/0285085 A1 | 11/2010 | Stankus et al. |
| 2010/0298928 A1 | 11/2010 | McClain et al. |
| 2010/0303881 A1 | 12/2010 | Hoke et al. |
| 2010/0305689 A1 | 12/2010 | Venkatraman et al. |
| 2011/0009953 A1 | 1/2011 | Luk et al. |
| 2011/0034422 A1 | 2/2011 | Kannan et al. |
| 2011/0034989 A1* | 2/2011 | Al-Marashi ............. A61F 2/915 623/1.11 |
| 2011/0060073 A1 | 3/2011 | Huang et al. |
| 2011/0159069 A1 | 6/2011 | Shaw et al. |
| 2011/0160751 A1 | 6/2011 | Granja |
| 2011/0172763 A1 | 7/2011 | Ndondo-Lay |
| 2011/0189299 A1 | 8/2011 | Okubo et al. |
| 2011/0190864 A1 | 8/2011 | McClain et al. |
| 2011/0223212 A1 | 9/2011 | Taton et al. |
| 2011/0238161 A1 | 9/2011 | Fulton et al. |
| 2011/0243884 A1 | 10/2011 | O'Shea et al. |
| 2011/0257372 A1 | 10/2011 | McClain et al. |
| 2011/0264190 A1 | 10/2011 | McClain et al. |
| 2011/0301697 A1 | 12/2011 | Hoffmann et al. |
| 2012/0064124 A1 | 3/2012 | McClain et al. |
| 2012/0064143 A1 | 3/2012 | Sharp et al. |
| 2012/0065723 A1 | 3/2012 | Drasler et al. |
| 2012/0101566 A1 | 4/2012 | Mews et al. |
| 2012/0150275 A1 | 6/2012 | Shaw-Klein |
| 2012/0160408 A1 | 6/2012 | Clerc et al. |
| 2012/0172787 A1 | 7/2012 | McClain et al. |
| 2012/0177742 A1 | 7/2012 | McClain et al. |
| 2012/0231037 A1 | 9/2012 | Levi et al. |
| 2012/0239161 A1 | 9/2012 | Datta et al. |
| 2012/0271396 A1 | 10/2012 | Zheng et al. |
| 2012/0280432 A1 | 11/2012 | Chen et al. |
| 2012/0290075 A1 | 11/2012 | Mortisen et al. |
| 2012/0323311 A1 | 12/2012 | McClain et al. |
| 2013/0006351 A1 | 1/2013 | Taylor et al. |
| 2013/0035754 A1 | 2/2013 | Shulze et al. |
| 2013/0087270 A1 | 4/2013 | Hossainy et al. |
| 2013/0110138 A1 | 5/2013 | Hurtado et al. |
| 2013/0172853 A1 | 7/2013 | McClain et al. |
| 2013/0291476 A1 | 11/2013 | Broughton, Jr. et al. |
| 2014/0343667 A1 | 11/2014 | McClain |
| 2014/0350522 A1 | 11/2014 | McClain et al. |
| 2014/0371717 A1 | 12/2014 | McClain et al. |
| 2015/0024116 A1 | 1/2015 | Matson et al. |
| 2015/0025620 A1 | 1/2015 | Taylor et al. |
| 2015/0250926 A1 | 9/2015 | McClain et al. |
| 2016/0095726 A1 | 4/2016 | McClain et al. |

FOREIGN PATENT DOCUMENTS

| | | |
|---|---|---|
| CA | 2615452 A1 | 1/2007 |
| CA | 2650590 A1 | 11/2007 |
| CA | 2679712 A1 | 7/2008 |
| CA | 2684482 A1 | 10/2008 |
| CA | 2721832 A1 | 12/2009 |
| CN | 2423899 Y | 3/2001 |
| CN | 1465410 | 1/2004 |
| CN | 1575860 A | 2/2005 |
| CN | 1649551 | 8/2005 |
| CN | 1684641 A | 10/2005 |
| CN | 101161300 A | 4/2008 |
| CN | 102481195 A | 5/2012 |

(56) References Cited

FOREIGN PATENT DOCUMENTS

| | | |
|---|---|---|
| DE | 4336209 A1 | 3/1995 |
| DE | 29702671 U1 | 4/1997 |
| DE | 29716476 U1 | 12/1997 |
| DE | 19633901 A1 | 2/1998 |
| DE | 29716467 U1 | 2/1998 |
| DE | 19740506 A1 | 3/1998 |
| DE | 19754870 A1 | 8/1998 |
| DE | 19822157 A1 | 11/1999 |
| DE | 69611186 T2 | 5/2001 |
| EP | 0335341 | 10/1989 |
| EP | 0604022 | 6/1994 |
| EP | 800801 A1 | 10/1997 |
| EP | 0876806 A1 | 11/1998 |
| EP | 0982041 | 3/2000 |
| EP | 1195822 A2 | 4/2002 |
| EP | 1325758 A2 | 7/2003 |
| EP | 1327422 A1 | 7/2003 |
| EP | 1454677 | 9/2004 |
| EP | 1502655 A2 | 2/2005 |
| EP | 1626752 A2 | 2/2006 |
| EP | 1750784 A1 | 2/2007 |
| EP | 1909973 A2 | 4/2008 |
| EP | 2197070 A1 | 6/2010 |
| EP | 2293357 A1 | 3/2011 |
| EP | 2293366 A1 | 3/2011 |
| FR | 2758253 A1 | 7/1998 |
| JP | 1994-098902 | 4/1994 |
| JP | H06218063 A | 8/1994 |
| JP | H08206223 A | 8/1996 |
| JP | H09-056807 | 3/1997 |
| JP | H1029524 A | 2/1998 |
| JP | H10151207 A | 6/1998 |
| JP | H10314313 A | 12/1998 |
| JP | H1157018 A | 3/1999 |
| JP | 2000316981 A | 11/2000 |
| JP | 2003-533493 | 11/2001 |
| JP | 2001521503 A | 11/2001 |
| JP | 2002239013 A | 8/2002 |
| JP | 2003-205037 | 7/2003 |
| JP | 2003-533286 | 11/2003 |
| JP | 2003-533493 | 11/2003 |
| JP | 2004512059 A | 4/2004 |
| JP | 2004/173770 | 6/2004 |
| JP | 2004-518458 | 6/2004 |
| JP | 2004-529674 | 9/2004 |
| JP | 2004528060 A | 9/2004 |
| JP | 2005-505318 | 2/2005 |
| JP | 2005168646 A | 6/2005 |
| JP | 2005519080 A | 6/2005 |
| JP | 2005-523119 | 8/2005 |
| JP | 2005-523332 | 8/2005 |
| JP | 2005-296690 | 10/2005 |
| JP | 2006506191 A | 2/2006 |
| JP | 2006512175 A | 4/2006 |
| JP | 2007502281 A | 2/2007 |
| JP | 2007215620 A | 8/2007 |
| JP | 2009-501566 | 1/2009 |
| JP | 2009529399 A | 8/2009 |
| JP | 2010052503 A | 3/2010 |
| JP | 2010515539 A | 5/2010 |
| JP | 2010516307 A | 5/2010 |
| JP | 2011517589 A | 6/2011 |
| JP | 2012527318 A | 11/2012 |
| JP | 2013153822 A | 8/2013 |
| KR | 10-2004-0034064 | 4/2004 |
| KR | 10-1231197 B1 | 2/2013 |
| WO | 9409010 A1 | 4/1994 |
| WO | WO-95/006487 | 3/1995 |
| WO | 9616691 A1 | 6/1996 |
| WO | WO 96/20698 | 7/1996 |
| WO | 9632907 A1 | 10/1996 |
| WO | 9641807 A1 | 12/1996 |
| WO | WO 97/045502 | 12/1997 |
| WO | 9802441 A2 | 1/1998 |
| WO | 9908729 A1 | 2/1999 |
| WO | 9915530 A1 | 4/1999 |
| WO | 9917680 A1 | 4/1999 |
| WO | 99016388 A1 | 4/1999 |
| WO | 0006051 A1 | 2/2000 |
| WO | 0025702 A1 | 5/2000 |
| WO | 00032238 A1 | 6/2000 |
| WO | 0114387 A1 | 3/2001 |
| WO | WO-2001/054662 | 8/2001 |
| WO | 0187345 A1 | 11/2001 |
| WO | 0187368 A1 | 11/2001 |
| WO | WO-2001-087371 | 11/2001 |
| WO | WO-2001/087372 | 11/2001 |
| WO | 0226281 A1 | 4/2002 |
| WO | WO-2002/040702 | 5/2002 |
| WO | WO-2002/043799 | 6/2002 |
| WO | 02055122 A1 | 7/2002 |
| WO | WO-2002-074194 A2 | 9/2002 |
| WO | WO-2002/090085 | 11/2002 |
| WO | 02100456 A1 | 12/2002 |
| WO | WO-2003/039553 | 5/2003 |
| WO | WO-2003-082368 A | 10/2003 |
| WO | 03090684 A2 | 11/2003 |
| WO | WO-2003/101624 A1 | 12/2003 |
| WO | WO-2004/009145 | 1/2004 |
| WO | 2004028406 A1 | 4/2004 |
| WO | WO-2004/028589 | 4/2004 |
| WO | WO-2004/043506 | 5/2004 |
| WO | 2004045450 A2 | 6/2004 |
| WO | WO-2004/045450 | 6/2004 |
| WO | WO-2004/098574 | 11/2004 |
| WO | 2005018696 A1 | 3/2005 |
| WO | WO-2005-042623 A1 | 5/2005 |
| WO | WO-2005/063319 | 7/2005 |
| WO | WO-2005/069889 | 8/2005 |
| WO | WO-2005-117942 A2 | 12/2005 |
| WO | WO-2006/014534 | 2/2006 |
| WO | WO-2006/052575 | 5/2006 |
| WO | 2006063430 A1 | 6/2006 |
| WO | WO-2006/065685 | 6/2006 |
| WO | WO-2006-083796 A2 | 8/2006 |
| WO | WO-2006-099276 A2 | 9/2006 |
| WO | 2007017707 A2 | 1/2007 |
| WO | 2007017708 A3 | 1/2007 |
| WO | WO-2007-002238 | 1/2007 |
| WO | WO-2007-011707 A2 | 1/2007 |
| WO | WO-2007-011707 A3 | 1/2007 |
| WO | WO-2007-011708 A2 | 1/2007 |
| WO | WO-2007-011708 A3 | 1/2007 |
| WO | WO-2007-127363 A2 | 1/2007 |
| WO | WO-2007/092179 | 8/2007 |
| WO | 2007106441 A2 | 9/2007 |
| WO | WO 2007/143609 | 12/2007 |
| WO | 2008024626 A2 | 2/2008 |
| WO | WO-2008/042909 | 4/2008 |
| WO | WO-2008-046641 A2 | 4/2008 |
| WO | WO-2008-046642 A2 | 4/2008 |
| WO | WO-2008/052000 | 5/2008 |
| WO | WO-2008/070996 | 6/2008 |
| WO | WO 2008/086369 | 7/2008 |
| WO | WO-2008/131131 A1 | 10/2008 |
| WO | WO-2008-131131 A1 | 10/2008 |
| WO | WO-2008/0148013 | 12/2008 |
| WO | 09039553 A1 | 4/2009 |
| WO | 2009051614 A1 | 4/2009 |
| WO | WO-2009/051614 | 4/2009 |
| WO | WO-2009/051780 | 4/2009 |
| WO | 2009096822 A1 | 8/2009 |
| WO | 2009113605 A1 | 9/2009 |
| WO | 2009120361 A2 | 10/2009 |
| WO | WO-2009/0146209 | 12/2009 |
| WO | 2010001932 A1 | 1/2010 |
| WO | WO 2010/009335 | 1/2010 |
| WO | WO-2010/075590 | 7/2010 |
| WO | 2010086863 A2 | 8/2010 |
| WO | WO-2010-111196 A2 | 9/2010 |
| WO | WO-2010-111196 A3 | 9/2010 |
| WO | WO-2010-111232 A3 | 9/2010 |
| WO | WO-2010-111232 A9 | 9/2010 |
| WO | WO-2010-111238 A2 | 9/2010 |

(56) References Cited

FOREIGN PATENT DOCUMENTS

| WO | WO-2010-111238 A3 | 9/2010 |
|---|---|---|
| WO | WO-2010-120552 A2 | 10/2010 |
| WO | WO-2010-120552 A3 | 10/2010 |
| WO | WO-2010-121187 A2 | 10/2010 |
| WO | WO-2010-121187 A3 | 10/2010 |
| WO | 2010135369 A1 | 11/2010 |
| WO | 2010136604 A1 | 12/2010 |
| WO | WO-2010/136604 A1 | 12/2010 |
| WO | WO-2011-009096 A1 | 1/2011 |
| WO | WO-2011/097103 | 8/2011 |
| WO | 2011119159 A1 | 9/2011 |
| WO | WO-2011/119762 | 9/2011 |
| WO | WO-2011/130448 | 10/2011 |
| WO | WO-2011/133655 | 10/2011 |
| WO | 2011140519 A2 | 11/2011 |
| WO | 2012009684 A2 | 1/2012 |
| WO | WO-2012/009684 | 1/2012 |
| WO | WO-2012/034079 | 3/2012 |
| WO | 2012078955 A1 | 6/2012 |
| WO | WO-2012/082502 | 6/2012 |
| WO | WO-2012/092504 | 7/2012 |
| WO | WO-2012/142319 | 10/2012 |
| WO | WO-2012/166819 | 12/2012 |
| WO | 2013003644 A1 | 1/2013 |
| WO | WO-2013/012689 | 1/2013 |
| WO | WO-2013/025535 | 2/2013 |
| WO | WO-2013/059509 | 4/2013 |
| WO | WO-2013/173657 | 11/2013 |
| WO | WO-2013/177211 | 11/2013 |
| WO | WO-2014/063111 | 4/2014 |
| WO | WO-2014/165264 | 10/2014 |
| WO | 2014186532 A1 | 11/2014 |

OTHER PUBLICATIONS

PCT/US06/24221 Search Report dated Jan. 29, 2007.
PCT/US06/27321 Search Report dated Oct. 16, 2007.
PCT/US06/27322 Search Report dated Apr. 25, 2007.
PCT/US07/10227 Search Report dated Aug. 8, 2008.
PCT/US07/82275 Search Report dated Apr. 18, 2008.
PCT/US07/080213 Search Report dated Apr. 16, 2008.
PCT/US08/11852 Search Report dated Dec. 19, 2008.
PCT/US08/50536 Search Report dated Jun. 2, 2008.
PCT/US08/60671 Search Report dated Sep. 5, 2008.
PCT/US08/64732 Search Report dated Sep. 4, 2008.
PCT/US09/41045 Search Report dated Aug. 11, 2009.
PCT/US09/50883 Search Report dated Nov. 17, 2009.
Latella et al., "Nanoindentation hardness. Young's modulus, and creep behavior of organic-inorganic silica-based sol-gel thin films on copper," J Mater Res 23(9): 2357-2365 (2008).
Schmidt et al., "In vitro measurement of quality parameters of stent-catheter systems," Biomed Techn 50(S1):1505-1506 (2005).
PCT/US10/28265 Search Report and Written Opinion dated Dec. 13, 2010.
U.S. Appl. No. 11/158,724 Office Action dated Sep. 17, 2009.
Akoh et al., "One-Stage Synthesis of Raffinose Fatty Acid Polyesters." Journal Food Science (1987) 52:1570.
Albert et al., "Antibiotics for preventing recurrent urinary tract infection in non-pregnant women," Cochrane Database System Rev. 3, CD001209 (2004).
Au et al., "Methods to improve efficacy of intravesical mitomycin C: Results of a randomized phase III trial," Journal of the National Cancer Institute, 93(8), 597-604 (2001).
AU2006270221 Exam Report dated Apr. 6, 2010.
AU2011232760 Exam Report dated Apr. 10, 2013.
AU2012203203 Exam Report dated Apr. 12, 2013.
AU2007243268 Exam Report dated May 15, 2013.
AU2007243268 Exam Report dated Aug. 31, 2011.
AU2009251504 Exam Report dated Dec. 8, 2011.
AU2009270849 Exam Report dated Feb. 14, 2012.
AU2012203577 Exam Report dated Jun. 7, 2013.
AU2011256902 Exam Report dated Jun. 13, 2013.
Balss et al., "Quantitative spatial distribution of sirolumus and polymers in drug-eluting stents using confocal Raman microscopy," J. of Biomedical Materials Research Part A, 258-270 (2007).
Belu et al., "Three-Dimensional Compositional Analysis of Drug Eluting Stent Coatings Using Cluster Secondary Ioan Mass Spectroscopy," Anal. Chem. 80:624-632 (2008).
Belu, et al., "Chemical imaging of drug eluting coatings: Combining surface analysis and confocal Rama microscopy" J. Controlled Release 126: 111-121 (2008).
Boneff, "Topical Treatment of Chronic Prostatitis and Premature Ejaculation," International Urology and Nephrology 4(2):183-186 (1971).
Bookbinder et al., "A recombinant human enzyme for enhanced interstitial transport of therapeutics," Journal of Controlled Release 114:230-241 (2006).
Borchert et al., "Prevention and treatement of urinary tract infection with probiotics: Review and research perspective," Indian Journal Urol. 24(2):139-144 (2008).
Brunstein et al., "Histamine, a vasoactive agent with vascular disrupting potential improves tumour response by enhancing local drug delivery," British Journal of Cancer 95:1663-1669 (2006).
Bugay et al., "Raman Analysis of Pharmaceuticals," in "Applications of Vibrational Spectroscopy in Pharmaceutical Research and Development," Ed. Pivonka, D.E., Chalmers, J.M., Griffiths, P.R. (2007) Wiley and Sons.
CA 2615452 Office Action dated Dec. 19, 2012.
CA 2684482 Office Action dated Jul. 11, 2012.
CA 2684482 Office Action dated Nov. 10, 2011.
CA 2688314 Office Action dated Jun. 6, 2012.
CA 2730995 Office Action dated Sep. 26, 2012.
CA 2757276 Office Action dated Feb. 15, 2013.
CA 2756307 Office action dated Feb. 18, 2013.
CA 2756386 Office action dated Mar. 15, 2013.
CA 2759015 Office action dated Apr. 8, 2013.
CA 2756388 Office Action dated Apr. 11, 2013.
CA 2613280 Office Action dated Oct. 2, 2012.
CA 2730995 Office action dated May 29, 2013.
CA 2650590 Office action dated Jul. 23, 2013.
Cadieux et al., "Use of triclosan-eluting ureteral stents in patients with long-term stents," J. Endourol (Epub) (Jun. 19, 2009).
Channon et al., "Nitric Oxide Synthase in Atherosclerosis and Vascular Injury: Insights from Experimental Gene Therapy," Arteriosclerosis, Thrombosis and Vascular Biology, 20(8): 1873-1881 (2000).
Chen et al. Immobilization of heparin on a silicone surface through a heterobifunctional PEG spacer. Biomaterials. Dec. 2005;26(35):7418-24.
Chlopek et al. "The influence of carbon fibres on the resorption time and mechanical properties of the lactide-glycolide co-polymer." J. Biomater. Sci. Polymer Edn, vol. 18, No. 11, pp. 1355-1368 (2007).
Clair and Burks, "Thermoplastic/Melt-Processable Polyimides," NASA Conf. Pub. #2334 (1984), pp. 337-355.
CN 2006800258093 Office Action dated May 30, 2012.
CN 200880007308.1 Office Action dated Nov. 23, 2011.
CN 200880007308.1 Office Action dated Oct. 18, 2012.
CN 200880020515 Office Action dated Oct. 9, 2012.
CN 200880100102.3 Office Action dated Jun. 1, 2012.
CN 200980122691 Office Action dated Oct. 10, 2012.
CN 200780047425.6 Office action dated Aug. 3, 2012.
CN 200780047425.6 Office action dated Feb. 28, 2013.
CN 200980136432.2 Office action dated Jan. 14, 2013.
CN 200880100102.3 Office Action dated Apr. 11, 2013.
CN 200880007308.1 Office Action dated Jul. 3, 2013.
CN200880020515 Office Action dated Jul. 22, 2013.
Cohen, et al. "Sintering Technique for the Preparation of Polymer Matrices fro the Controlled Release of Macromolecules." Journal of Pharamceutical Sciences, vol. 73, No. 8, 1984, p. 1034-1037.
CRC Handbook of chemistry and physics. 71st ed. David R. Lide, Editor-in-Chief. Boca Raton, FL, CRC Press; 1990; 6-140.
Cyrus et al., "Intramural delivery of rapamycin with alphavbeta3-targeted paramagnetic nanoparticles inhibits stenosis after balloon injury," Arterioscler Thromb Vasc Biol 2008;28:820-826.

(56) References Cited

OTHER PUBLICATIONS

DERWENT-ACC-No. 2004-108578 Abstracting 2004003077; Jan. 8, 2004; 3 pages.
DiStasi et al., "Percutaneous sequential bacillus Calmette-Guerin and mitomycin C for panurothelial carcinomatosis," Can. J. Urol. 12(6):2895-2898 (2005).
Domingo, C. et al., "Precipication of ultrafine organic crystals from the rapid expansion of supercritical solutions over a capillary and a frit nozzle," J. Supercritical Fluids 10:39-55 (1997).
Dzik-Jurasz, "Molecular imaging in vivo: an introduction," The British Journal of Radiology, 76:S98-S109 (2003).
EA 201001497 Office Action dated Feb. 11, 2013.
EA 200901254/28 Office Action dated Jul. 18, 2012.
Electrostatic Process, Wiley Encyclopedia of Electrical and Electronics Engineering, John Wiley & Sons, Inc. 1999; 7:15-39.
Eltze et al., "Imidazoquinolinon, imidazopyridine, and isoquinolindione derivatives as novel and potent inhibitors of the poly (ADP-ribose) polymerase (PARP): a comparison with standard PARP inhibitors," Mol. Pharmacol 74(6):1587-1598 (2008).
EP06773731.2 Search Report dated Oct. 2, 2012.
EP06787258.0 Search Report dated Feb. 6, 2012.
EP07756094.4 Search Report dated Aug. 31, 2012.
EP08733210.2 Search Report dated Oct. 23, 2012.
EP08756215.3 Search Report dated Oct. 5, 2011.
EP08756215.3 Search Report dated Jan. 28, 2013.
EP09805981.9 Office Action dated Feb. 13, 2013.
EP06787258.0 Office Action dated Mar. 15, 2013.
EP09755571.8 Search Report dated Apr. 9, 2013.
EP08705772.5 Search Report dated Feb. 20, 2013.
EP07756094.4 Office action dated May 29, 2013.
EP08733210.2 Office action dated Jul. 16, 2013.
Ettmayer et al. Lessons learned from marketed and investigational prodrugs. J Med Chem. May 6, 2004;47(10):2393-404.
Fibbi et al., "Chronic inflammation in the pathogenesis of benign prostatic hyperplasia," Int J Androl. Jun. 1, 2010;33(3):475-88.
Fleischmann et al., "High Expression of Gastrin-Releasing Peptide Receptors in the Vascular bed of Urinary Tract Cancers: Promising Candidates for Vascular Targeting Applications." Jun. 2009, Endocr. Relat. Cancer 16(2):623-33.
Froehlich et al., "Conscious sedation for gastroscopy: patient tolerance and cardiorespiratory parameters," Gastroenterology 108(3):697-704 (1995).
Fujiwara et al., "Insulin-like growth factor 1 treatment via hydrogels rescues cochlear hair cells from ischemic injury," Oct. 29, 2008, NeuroReport 19(16):1585-1588.
Fulton et al. Thin Fluoropolymer films and nanoparticle coatings from the rapid expansion of supercritical carbon dioxide solutions with electrostatic collection, Polymer Communication. 2003; 2627-3632.
Green et al., "Simple conjugated polymer nanoparticles as biological labels," Proc Roy Soc A. published online Jun. 24, 2009 doi:10.1098/rspa.2009.0181.
Griebenow et al., "On Protein Denaturation in Aqueous-Organic Mixtures but not in Pure Organic Solvents," J. Am Chem Soc., vol. 118. No. 47, 11695-11700 (1996).
Hamilos et al., "Differential effects of Drug-Eluting Stents on Local Endothelium-Dependent Coronary Vasomotion." JACC vol. 51, No. 22, 2008, Endothelium and DES Jun. 3, 2008:2123-9.
Hartmann et al., "Tubo-ovarian abscess in virginal adolescents: exposure of the underlying etiology," J. Pediatr Adolesc Gynecol, 22(3):313-16 (2009).
Hasegawa et al., "Nylong 6/Na-montmorillonite nano composites prepared by compounding Nylon 6 with Na-montmorillonite slurry," Polymer 44 (2003) 2933-2937.
Hinds, WC. Aerosol Technology, Properties, Behavior and Measurement of Airborne Particles, Department of Environmental Health Sciences, Harvard University School of Public Health, Boston, Massachusetts. 1982; 283-314.
Hladik et al., "Can a topical microbicide prevent rectal HIV transmission?" PLoS Med. 5(8):e167 (2008).

Iconomidou et al., "Secondary Structure of Chorion Proteins of the Teleosatan Fish Dentex dentex by ATR FR-IR and FT-Raman Spectroscopy," J. of Structural Biology, 132, 112-122 (2000).
IN-368/DELNP/2008 Exam Report dated Oct. 17, 2011.
IL-208648 Official Notification dated Feb. 9, 2012.
Jackson et al., "Characterization of perivascular poly(lactic-co-glycolic acid) films containing paclitaxel" Int. J. of Pharmaceutics, 283:97-109 (2004), incorporated in its entirety herein by reference.
Jensen et al., Neointimal hyperplasia after sirollmus-eluting and paclitaxel-eluting stend implantation in diabetic patients: the randomized diabetes and drug eluting stent (DiabeDES) intravascular ultrasound trial. European heart journal (29), pp. 2733-2741. Oct. 2, 2008. Retrieved from the Internet. Retrieved on [Jul. 17, 2012]. URL:<http://eurheartj.oxfordjournals.org/content/29/22/2733.full.pdf> entire document.
Jewell, et al., "Release of Plasmid DNA from Intravascular Stents Coated with Ultrathin Multilayered Polyelectrolyte Films" *Biomacromolecules.* 7: 2483-2491 (2006).
Johns, H.E, J.R.Cunningham, Thomas, Charles C., Publisher, "The Physics of Radiology," 1983, Springfield, IL, pp. 133-143.
Joner et al. "Site-specific targeting of nanoparticle prednisolone reduces in-stent restenosis in a rabbit model of established atheroma," Arterioscler Thromb Vase Biol. 2008;28:1960-1966.
Mei et al., "Local Delivery of Modified Paclitaxel-Loaded Poly(ε-caprolactone)/Pluronic F68 Nanoparticles for Long-Term Inhibition of Hyperplasia," Journal of Pharmaceutical Sciences, vol. 98, No. 6, Jun. 2009.
Jovanovic et al. "Stabilization of Proteins in Dry Powder Formulations Using Supercritical Fluid Technology," Pharm. Res. 2004; 21(11).
JP 2008-521633 Office Action dated Oct. 12, 2012.
JP2008-521633 Office Action dated Dec. 28, 2011.
JP-2009-534823 Office Action dated Sep. 20, 2012.
JP-2009-534823 Office Action dated Feb. 21, 2012.
JP-2009-545647 Office Action dated Jun. 5, 2012.
JP-2010-504253 Office Action dated Dec. 12, 2011.
JP-2010-504253 Office Action dated Dec. 7, 2012.
JP-2011-518920 Office action dated Dec. 17, 2012.
JP-2009-534823 Office Action dated Apr. 23, 2013.
JP-2012-503677 Office action dated Jan. 18, 2013.
JP-2011-505248 Office action dated Jun. 4, 2013.
JP-2010-510441 Office action dated May 7, 2013.
JP-2009-545647 Office Action dated May 14, 2013.
Kazemi et al., "The effect of betamethasone gel in reducing sore throat, cough, and hoarseness after laryngo-tracheal intubation," Middle East J. Anesthesiol. 19(1):197-204 (2007).
Kehinde et al., "Bacteriology of urinary tract infection associated with indwelling J ureteral stents," J. Endourol. 18(9):891-896 (2004).
Kelly et al., "Double-balloon trapping technique for embolization of a large wide-necked superior cerebellar artery aneurysm: case report," Neurosurgery 63(4 Suppl 2):291-292 (2008).
Khan et al., "Cyclic Acetals of 4,1',6'-Trichloro-4,1',6',-Trideoxy-Trideoxy-galacto-Sucrose and their Conversion into Methyl Ether Derivatives.". Carb. Res. (1990) 198:275-283.
Khan et al., "Chemistry and the new uses of Sucrose: How Important?" Pur and Appl. Chem (1984) 56:833-844.
Khan et al., "Enzymic Regioselective Hydrolysis of Peracetylated Reducing Disaccharides, Specifically at the Anomeric Centre: Intermediates for the Synthesis of Oligosaccharides." Tetrahedron Letters (1933) 34:7767.
Koh et al. "A novel nanostructured poly(lactic-co-glycolic-acid)-multi-walled carbon nanotube composite for blood-contacting applications: Thrombogenicity studies."
KR10-2008-7003756 Office Action dated Oct. 30, 2012.
Kurt et al., "Tandem oral, rectal and nasal administrations of Ankaferd Blood Stopper to control profuse bleeding leading to hemodynamic instability," Am J. Emerg. Med. 27(5):631, e1-2 (2009).
Labhasetwar et al., "Arterial uptake of biodegradable nanoparticles: effect of surface modifications," Journal of Pharmaceutical Sciences, vol. 87, No. 10, Oct. 1998; 1229-1234.

(56) References Cited

OTHER PUBLICATIONS

Lamm et al., "Bladder Cancer: Current Optimal Intravesical Treatment: Pharmacologic Treatment," Urologic Nursing 25(5):323-6, 331-2 (Oct. 26, 2005).
Lee et al., "Novel therapy for hearing loss: delivery of insulin-like growth factor 1 to the cochlea using gelatin hydrogel," Otol. Neurotol. 28(7):976-81 (2007).
Lehmann et al., "Drug treatment of nonviral sexually transmitted diseases: specific issues in adolescents," Pediatr Drugs 3(7):481-494 (2001.
Mahoney et al., "Three-Dimensional Compositional Analysis of Drug Eluting Stent Coatings Using Cluster Secondary Ion mass Spectrometry," Anal. Chem. , 80, 624-632 (2008).
Mario, C.D. et al., "Drug-Eluting Bioabsorbable Magnesium Stent," J. Interventional Cardiology 16(6):391-395 (2004).
McAlpine, J.B. et al., "Revised NMR Assignments for Rapamycine," J. Antibiotics 44:688-690 (1991).
Mehik et al., "Alfuzosin treatment for chronic prostatitis/chronic pelvic pain syndrome: a prospecitve, randomized, double-blind, placebo-controlled, pilot study," Urology 62(3):425-429 (2003).
Melonakos et al., Treatment of low-grade bulbar transitional cell carcinoma with urethral instillation of mitomycin C, Oct. 28, 2008, Adv. Urol., 173694 Epub.
Merrett et al., "Interaction of corneal cells with transforming growth factor beta2-modified poly dimethyl siloxane surfaces," Journal of Biomedical Materials Research, Part A, vol. 67A, No. 3, pp. 981-993 (2003).
Middleton and Tipton, Synthetic biodegradable polymers as orthopedic devises. Biomaterials 2000; 21:2335-46.
Minoque et al., "Laryngotracheal topicalization with lidocaine before intubation decreases the incidence of coughing on emergence from general anesthesia," Anesth. Analg. 99(4):1253-1257 (2004).
Mocco et al., "Pharos neurovascular intracranail stent: Elective use for a symptomatic stenosis refractory to medical therapy," Catheter Cardiovasc. Interv. (epub) (Mar. 2009).
Mollen et al., "Prevalence of tubo-ovarian abcess in adolescents diagnosed with pelvice inflammatory disease in a pediatric emergency department," Pediatr. Emerg. Care, 22(9): 621-625 (2006).
Moroni et al., "Post-ischemic brain damage:Targeting PARP-1 within the ischemic neurovaschular units as a realistic avenue to stroke treatment," FEBS J. 276(1):36-45 (2009).
Muhlen et al., "Magnetic Resonance Imaging Contrast Agent Targeted Toward Activated Platelets Allows in Vivo Detection of Thrombosis and Monitoring of Thrombolysis Circulation," 118:258-267 (2008).
NZ 588549 Examination Report dated Mar. 28, 2011.
PCT/US08/50536 International Search Report dated Jun. 2, 2008.
PCT/US12/46545 International Search Report dated Nov. 20, 2012.
PCT/US12/50408 International Search Report dated Oct. 19, 2012.
PCT/US2012/040040 International Search Report dated Sep. 7, 2012.
Perry et al., Chemical Engineer's Handbook, 5th Edition, McGraw-Hill, New York, 1973; 20-106.
Torchlin, "Micellar Nanocarriers: Pharmaecutial Perspectives," Pharmaceutical Research, vol. 24, No. 1, Jan. 2007.
Plas et al., "Tubers and tumors: rapamycin therapy for benign and malignant tumors", Curr Opin Cell Bio 21: 230-236, (2009).
Poling et al., The Properties of Gases and Liquids. McGraw-Hill, 2001; 9:1-9.97.
Pontari, "Chronic prostatitis/chronic pelvic pain syndrome in elderly men: toward better understanding and treatment," Drugs Aging 20(15):1111-1115 (2003).
Pontari, "Inflammation and anti-inflammatory therapy in chronic prostatits," Urology 60(6Suppl):29-33 (2002).
Raganath et al., "Hydrogel matrix entrapping PLGA-paclitaxel microspheres: drug delivery with near zero-order release and implantability advantages for malignant brain tumour," Pharm Res (Epub) Jun. 20, 2009).
Ranade et al., "Physical characterization of controlled release of paclitaxel from the TAXUS Express2 drug-eluting stent," J. Biomed Mater. Res. 71(4):625-634 (2004).
Reddy et al., "Inhibition of apoptosis through localized delivery of rapamycin-loaded nanoparticles prevented neointimal hyperplasia and reendothelialized injured artery," Circ Cardiovasc Interv 2008;1;209-216.
Sahajanand Medical Technologies (Supralimus Core; Jul. 6, 2008).
Schmidt et al., "A Comparison of the Mechanical Performance Characteristics of Seven Drug-Eluting Stent Systems," Catheterization and Cardiovascular Interventions 73:350-360 (2009).
Schmidt et al., "New aspects of in vitro testing of arterial stents based on the new European standard," EN 14299, [online] (2009), [retrieved on Mar. 10, 2001] http://www.lib0ev.de/pl/pdf/EN14299.pdf (2009).
Schmidt et al., "Trackability, Crossability, and Pushability of Coronary Stent Systems—An Experimental Approach," Biomed Techn 47 (2002), Erg. 1, S. 124-126.
Schreiber, S.L. et al., "Atomic Structure of the Rapamycin Human Immunophilin FKBP-12 Complex," J. Am. Chem. Soc. 113:7433-7435 (1991).
Sen et al., "Topical heparin: A promising agent for the prevention of tracheal stenosis in airway surgery," J. Surg. Res (Epub ahead of print) Feb. 21, 2009.
Serruys, Patrick et al., Comparison of Coronary-Artery Bypass Surgery and Stenting for the Treatment of Multivessel Disease, N. Engl. J. Med., 2001, vol. 344, No. 15, pp. 1117-1124.
SG201007602-4 Examination Report dated Feb. 13, 2013.
Shekunov et al. "Crystallization Processes in Pharmaceutical Technology and Drug Delivery Design." Journal of Crystal Growth 211 (2000), pp. 122-136.
Simpson et al., "Hyaluronan and hyaluronidase in genitourinary tumors." Front Biosci. 13:5664-5680.
Smith et al., "Mitomycin C and the endoscopic treatment of laryngotracheal stenosis: are two applications better than one?" Laryngoscope 119(2):272-283 (2009).
Szabadits et al., "Flexibility and trackability of laser cut coronary stent systems," Acta of Bioengineering and Biomechanics 11(3):11-18 (2009).
Thalmann et al., "Long-term experience with bacillus Calmette-Guerin therapy of upper urinary tract transitional cell carcinoma in patients not eligible for surgery," J Urol. 168(4 Pt 1):1381-1385 (2002).
Merriam-Webster Online Dictionary, obtained onlie at: http://www.merriam-webster.com/dictionary/derivative, downloaded 07 Jul. 5, 2008.
U.S. Appl. No. 11/158,724 Office Action dated Sep. 8, 2008.
U.S. Appl. No. 11/877,591 Office Action dated Feb. 29, 2012.
U.S. Appl. No. 11/877,591 Office Action dated Sep. 21, 2012.
U.S. Appl. No. 11/995,685 Office Action dated Aug. 20, 2010.
U.S. Appl. No. 11/995,685 Office Action dated Nov. 24, 2009.
U.S. Appl. No. 11/995,687 Office Action dated Sep. 28, 2011.
U.S. Appl. No. 12/298,459 Office Action dated Aug. 10, 2011.
U.S. Appl. No. 12/298,459 Office Action dated Apr. 6, 2012.
U.S. Appl. No. 12/426,198 Office Action dated Feb. 6, 2012.
U.S. Appl. No. 12/426,198 Office Action dated Mar. 23, 2011.
U.S. Appl. No. 12/443,959 Office Action dated Dec. 13, 2012.
U.S. Appl. No. 12/443,959 Office Action dated Feb. 15, 2012.
U.S. Appl. No. 12/504,597 Final Office Action dated Oct. 3, 2012.
U.S. Appl. No. 12/504,597 Office Action dated Dec. 5, 2011.
U.S. Appl. No. 12/522,379 Office Action dated Dec. 26, 2012.
U.S. Appl. No. 12/595,848 Office Action dated Jan. 13, 2012.
U.S. Appl. No. 12/601,101 Office Action dated Dec. 27, 2012.
U.S. Appl. No. 12/601,101 Office Action dated Mar. 27, 2012.
U.S. Appl. No. 12/648,106 Final Office Action dated Sep. 25, 2012.
U.S. Appl. No. 12/648,106 Office Action dated Jan. 30, 2012.
U.S. Appl. No. 12/729,156 Final Office Action dated Oct. 16, 2012.
U.S. Appl. No. 12/729,156 Office Action dated Feb. 1, 2012.
U.S. Appl. No. 12/729,580 Office Action dated Apr. 10, 2012.
U.S. Appl. No. 12/729,580 Office Action dated Jan. 22, 2013.
U.S. Appl. No. 12/729,603 Final Office Action dated Oct. 10, 2012.
U.S. Appl. No. 12/729,603 Office Action dated Mar. 27, 2012.
U.S. Appl. No. 12/751,902 Office Action dated Jul. 13, 2012.

(56) References Cited

OTHER PUBLICATIONS

U.S. Appl. No. 12/595,848 Office Action dated Mar. 15, 2013.
U.S. Appl. No. 12/738,411 Final Office action dated Apr. 11, 2013.
U.S. Appl. No. 13/605,904 Office Action dated Nov. 27, 2012.
U.S. Appl. No. 12/762,007 Office action dated Feb. 11, 2013.
U.S. Appl. No. 13/384,216 Office action dated Apr. 24, 2013.
U.S. Appl. No. 13/340,472 Office action dated Apr. 26, 2013.
U.S. Appl. No. 12/729,156 Office action dated May 8, 2013.
U.S. Appl. No. 13/086,335 Office action dated May 22, 2013.
U.S. Appl. No. 11/158,724 Office action dated May 23, 2013.
U.S. Appl. No. 12/601,101 Office action dated May 22, 2013.
U.S. Appl. No. 12/298,459 Office Action dated May 31, 2013.
U.S. Appl. No. 13/229,473 Office Action dated Jun. 17, 2013.
U.S. Appl. No. 13/605,904 Office Action dated Jun. 28, 2013.
U.S. Appl. No. 11/877,591 Office Action dated Jul. 1, 2013.
U.S. Appl. No. 12/748,134 Office Action dated Jul. 18, 2013.
U.S. Appl. No. 12/738,411 Office action dated Aug. 21, 2013.
U.S. Appl. No. 12/522,379 Final Office Action dated Aug. 28, 2013.
Unger et al., "Poly(ethylene carbonate): A thermoelastic and biodegradable biomaterial for drug eluting stent coatings?" Journal fo Controlled Release, vol. 117, Issue 3, 312-321 (2007).
Verma et al., "Effect of surface properties on nanoparticle-cell interactions," *Small* 2010, 6, No. 1, 12-21.
Wagenlehner et al., "A pollen extract (Cernilton) in patients with inflammatory chronic prostatitis/chronic pelvic pain syndrome: a multicentre, randomized, prospective, double-blind, placebo-controlled phase 3 study," Eur Urol 9 (Epub) (Jun. 3, 2009).
Wang et al. Controlled release of sirolimus from a multilayered PLGA stent matrix. Biomaterials 2000; 27:5588-95.
Wang et al., "Treatment with melagatran alone or in combination with thrombolytic therapy reduced ischemic brain injury," Exp. Neurol 213(1):171-175 (2008).
Warner et al., "Mitomycin C and airway surgery: how well does it work?" Ontolaryngol Head Neck Surg. 138(6):700-709 (2008).
Wermuth, CG Similarity in drugs: reflections on analogue design. Drug Discov Today. Apr. 2006;11(7-8):348-54.
Witjes et al., "Intravesical pharmacotherapy for non-muscle-invasive bladder cancer: a critical analysis of currently available drugs, treatment schedules, and long-term results," Eur. Urol. 53(1):45-52.
Wu et al., "Study on the preparation and characterization of biodegradable polylactide/multi-walled carbon nanotubes nanocomposites." Polymer 48 (2007) 4449-4458.
Xu et al., "Biodegradation of poly(l-lactide-co-glycolide tube stents in bile" *Polymer Degradation and Stability.* 93:811-817 (2008).
Xue et al., "Spray-as-you-go airway topical anesthesia in patients with a difficult airway: a randomized, double-blind comparison of 2% and 4% lidocaine," Anesth. Analg. 108(2): 536-543 (2009).
Yepes et al., "Tissue-type plasminogen activator in the ischemic brain: more than a thrombolytic," Trends Neurosci. 32(1):48-55 (2009).
Yousof et al., "Reveratrol exerts its neuroprotective effect by modulating mitochondrial dysfunction and associated cell death during cerebral ischemia," Brain Res. 1250:242-253 (2009).
Zhou et al. Synthesis and Characterization of Biodegradable Low Molecular Weight Aliphatic Polyesters and Their Use in Protein-Delivery Systems. J Appl Polym Sci 2004; 91:1848-56.
PCT/US2011/032371 International Search Report dated Jul. 7, 2011.
PCT/US10/42355 Search Report dated Sep. 2, 2010.
PCT/US10/28253 Search Report and Written Opinion dated Dec. 6, 2010.
PCT/US10/28265 Search Report and Written Opinion dated Dec. 3, 2010.
PCT/US10/28195 Search Report and Written Opinion dated Jan. 21, 2011.
PCT/US10/31470 Search Report and Written Opinion dated Jan. 28, 2011.
PCT/US10/29494 Search Report and Written Opinion dated Feb. 7, 2011.
PCT/US11/22623 Search Report and Written Opinion dated Mar. 28, 2011.
PCT/US2011/044263 International Search Report, International Preliminary Report on Patentability and Written Opinion dated Feb. 9, 2012.
PCT/US2007/82775 International Preliminary Report on Patentablity dated Apr. 28, 2009.
PCT/US09/69603 International Search Report dated Nov. 5, 2010.
PCT/US09/50883 International Preliminary Report on Patentability dated Jan. 18, 2011.
PCT/US10/28253 International Preliminary Report on Patentability dated Sep. 27, 2011.
PCT/US12/33367 International Search Report dated Aug. 1, 2012.
PCT/US10/28195 International Preliminary Report on Patentability dated Oct. 6, 2011.
PCT/US2011/051092 International Preliminary Report on Patentability dated Mar. 21, 2013.
PCT/US10/42355 International Preliminary Report on Patentability dated Jan. 17, 2012.
PCT/US2011/67921 Search Report and Written Opinion dated Jun. 22, 2012.
PCT/US2011/67921 International Preliminary Report on Patentability dated Jul. 11, 2013.
AU 2011256902 Office Action dated Jun. 10, 2014.
CA 2650590 Office action dated Sep. 18, 2014.
CA 2756307 Office action dated Mar. 24, 2014.
CA 2756386 Office Action dated May 16, 2014.
CA 2756388 Office Action dated Apr. 14, 2014.
CA 2759015 Office Action dated Jul. 21, 2014.
CA 2823355 Office action dated Apr. 14, 2014.
CN 200880020515 Office Action dated Apr. 15, 2014.
CN 200880020515 Office Action dated Oct. 21, 2014.
CN 200880100102.3 Office Action dated Aug. 27, 2014.
CN 200980136432.2 Office Action dated Jul. 3, 2014.
CN 201080024973.9 Office Action dated Aug. 7, 2014.
CN 201210206265.8 Office Action dated Sep. 15, 2014.
EP10800642.0 Search Report dated Mar. 19, 2014.
EP11772624.0 Search Report dated Jun. 5, 2014.
EP09798764.8 Office Action dated Jun. 30, 2014.
EP118077601.7 Search Report dated Sep. 17, 2014.
EP11852627.6 Search Report dated Sep. 17, 2014.
EP12771847.6 Search Report dated Oct. 15, 2014.
Han, et al., "Studies of a Novel Human Thrombomodulin Immobilized Substrate: Surface Characterization and Anticoagulation Activity Evaluation." J. Biomater. Sci. Polymer Edn, 2001, 12 (10), 1075-1089.
ID—W00201003529 Office action dated Apr. 28, 2014.
IN-7740/DELNP/2009 Office Action dated Jul. 29, 2014.
JP 2008-521633 Office Action Translation dated Oct. 3, 2014.
JP-2009-545647 Office Action dated Apr. 22, 2014.
JP-2013-024508 Office Action dated May 2, 2014.
JP-2013-190903 Office Action dated Sep. 2, 2014.
KR10-2013-7031237 Office action dated Mar. 17, 2014.
PCT/US2014/025017 International Search Report and Written Opinion dated Jul. 7, 2014.
PCT/US2014/038117 International Search Report and Written Opinion dated Oct. 7, 2014.
Putkisto, K. et al. "Polymer Coating of Paper Using Dry Surface Treatment—Coating Structure and Performance", ePlace newsletter, (Apr. 12, 2004), vol. 1, No. 8, pp. 1-20.
U.S. Appl. No. 11/158,724 Office Action dated Jun. 25, 2014.
U.S. Appl. No. 11/877,591 Office Action dated May 7, 2014.
U.S. Appl. No. 11/877,591 Final Office Action dated Sep. 29, 2014.
U.S. Appl. No. 11/995,685 Advisory Action dated Oct. 9, 2014.
U.S. Appl. No. 12/426,198 Office Action dated Nov. 3, 2014.
U.S. Appl. No. 12/504,597 Office Action dated Apr. 1, 2014.
U.S. Appl. No. 12/504,597 Office Action dated Oct. 23, 2014.
U.S. Appl. No. 12/522,379 Office Action dated Apr. 8, 2014.
U.S. Appl. No. 12/595,848 Office Action dated Jun. 3, 2014.
U.S. Appl. No. 12/601,101 Notice of Allowability dated Oct. 23, 2014.
U.S. Appl. No. 12/729,580 Office Action dated Sep. 10, 2014.
U.S. Appl. No. 12/729,603 Office Action dated Jun. 25, 2014.

(56) References Cited

OTHER PUBLICATIONS

U.S. Appl. No. 12/738,411 Office Action dated May 30, 2014.
U.S. Appl. No. 12/762,007 Final Office Action dated Apr. 30, 2014.
U.S. Appl. No. 13/086,335 Office Action dated Apr. 4, 2014.
U.S. Appl. No. 13/340,472 Office Action dated Aug. 29, 2014.
U.S. Appl. No. 13/090,525 Office Action dated Apr. 11, 2014.
U.S. Appl. No. 11/995,685 Office Action dated Jun. 18, 2014.
Abreu Filho et al., "Influence of metal alloy and the profile of coronary stents in patients with multivessel coronary disease," CLINICS 2011;66(6):985-989.
CA 2757276 Office Action dated Feb. 5, 2014.
CA 2794704 Office action dated Feb. 7, 2014.
CA 2615452 Office Action dated Oct. 8, 2013.
CA 2613280 Office action dated Dec. 10, 2013.
CA 2667228 Office action dated Jan. 22, 2014.
CA 2679712 Office action dated Feb. 24, 2014.
CA 2667228 office action dated May 7, 2013.
CA 2730995 Office Action dated Feb. 20, 2014.
CA 2756386 Office action dated Oct. 24, 2013.
CA 2805631 Office Action dated Jan. 17, 2014.
CN 200880007308.1 Office Action dated Jan. 2, 2014.
CN 200880100102.3 Office Action dated Dec. 11, 2013.
CN 200980136432.2 Office action dated Nov. 4, 2013.
CN 201080024973.9 Office action dated Dec. 20, 2013.
Colombo et al. "Selection of Coronary Stents," Journal of the American College of Cardiology, vol. 40, No. 6, 2002, p. 1021-1033.
EA 200901254 Office Action dated Jul. 29, 2013.
EA 201001497 Office Action dated Jul. 29, 2013.
EP07756094.4 Office Action dated Jan. 21, 2014.
EP08705772.5 Office Action dated Oct. 30, 2013.
EP09755571.8 Office Action dated Dec. 13, 2013.
EP09798764.8 Search Report dated Sep. 30, 2013.
EP10756676.2Search Report dated Jan. 31, 2014.
EP10756696.0 Search Report dated Oct. 10, 2013.
EP10764884.2 Search Report dated Oct. 28, 2013.
EP10765295.0 Search Report dated Oct. 17, 2013.
EP11769546.0 Search Report dated Sep. 19, 2013.
IL-201550 Official Notification dated Dec. 8, 2013.
IN-6884DEFNP2009 Office Action dated Oct. 31, 2013.
JP-2011-518920 Office action dated Oct. 23, 2013.
JP-2012-503677 Office action dated Nov. 1, 2013.
JP-2012-151964 Office Action dated Dec. 10, 2013.
KR10-2008-7003756 Office Action dated Sep. 23, 2013.
Matsumoto, D, et al. Neointimal Coverage of Sirolimus-Eluting Stents at 6-month Follow-up: Evaluated by Optical Coherence Tomography, European Heart Journal, Nov. 29, 2006; 28:961-967.
MX/a/2010/01 148 Office action dated Feb. 11, 2014.
PCT/US06/24221 International Preliminary Report on Patentability dated Dec. 24, 2007.
PCT/US06/27321 International Preliminary Report on Patentability dated Jan. 16, 2008.
PCT/US06/27322 International Preliminary Report on Patentability dated Jan. 16, 2008.
PCT/US07/10227 International Preliminary Report on Patentability dated Oct. 28, 2008.
PCT/US07/80213 International Preliminary Report on Patentability dated Apr. 7, 2009.
PCT/US08/11852 International Preliminary Report on Patentability dated Apr. 20, 2010.
PCT/US08/50536 International Preliminary Report on Patentability dated Jul. 14, 2009.
PCT/US08/60671 International Preliminary Report on Patentability dated Oct. 20, 2009.
PCT/US08/64732 International Preliminary Report on Patentability dated Dec. 1, 2009.
PCT/US09/41045 International Preliminary Report on Patentability dated Oct. 19, 2010.
PCT/US09/69603 International Preliminary Report on Patentability dated Jun. 29, 2011.
PCT/US10/28265 International Report on Patentability dated Sep. 27, 2011.
PCT/US10/29494 International Preliminary Report on Patentability dated Oct. 4, 2011.
PCT/US10/31470 International Preliminary Report on Patentability dated Oct. 18, 2011.
PCT/US11/032371 International Report on Patentability dated Oct. 16, 2012.
PCT/US11/051092 International Search Report dated Mar. 27, 2012.
PCT/US11/051092 Written Opinion dated Mar. 27, 2012.
PCT/US11/22623 International Preliminary Report on Patentability dated Aug. 7, 2012.
PCT/US11/29667 International Search Report and Written Opinion dated Jun. 1, 2011.
PCT/US12/33367 International Preliminary Report on Patentability dated Oct. 15, 2013.
PCT/US13/41466 International Search Report and Written Opinion dated Oct. 17, 2013.
PCT/US13/42093 International Search Report and Written Opinion dated Oct. 24, 2013.
PCT/US2011/033225 International Search Report and Written Opinion dated Jul. 7, 2011.
PCT/US2012/60896 International Search Report and Written Opinion dated Dec. 28, 2012.
PCT/US2013/065777 International Search Report and Written Opinion dated Jan. 29, 2014.
U.S. Appl. No. 11/158,724 Office action dated Dec. 31, 2013.
U.S. Appl. No. 11/877,591 Final Action dated Nov. 4, 2013.
U.S. Appl. No. 12/426,198 Office Action dated Feb. 7, 2014.
U.S. Appl. No. 12/595,848 Office Action dated Oct. 22, 2013.
U.S. Appl. No. 12/601,101 Office Action dated Feb. 13, 2014.
U.S. Appl. No. 12/648,106 Office Action dated Sep. 18, 2013.
U.S. Appl. No. 12/729,156 Office Action dated Feb. 13, 2014.
U.S. Appl. No. 12/729,580 Final Action dated Nov. 14, 2013.
U.S. Appl. No. 12/738,411 Office Action dated Feb. 6, 2014.
U.S. Appl. No. 12/751,902 Office Action dated Dec. 19, 2013.
U.S. Appl. No. 12/762,007 Final Office action dated Oct. 22, 2013.
U.S. Appl. No. 13/340,472 Office action dated Jan. 15, 2014.
U.S. Appl. No. 13/384,216 Final Action dated Nov. 6, 2013.
U.S. Appl. No. 13/445,723 Office action dated Mar. 14, 2014.
Zilberman et al., Drug-Eluting bioresorbable stents for various applications, Annu Rev Biomed Eng., 2006;8:158-180.
David Grant, Crystallization Impact on the Nature and Properties of the Crystalline Product, 2003, SSCI, http://www.ssci-inc.com/Information/RecentPublications/ApplicationNotes/CrystallizationImpact/tabid/138/Default.aspx.
Analytical Ultracentrifugation of Polymers and Nanoparticles, W. Machtle and L. Borger, (Springer) 2006, p. 41.
Chalmers, et al. (2007) Wiley and Sons.
Domb and Langer, "Polyanhydrides. I. Preparation of High Molecular Weight Polyanhydrides." J. Polym Sci. 25:3373-3386 (1987).
European International Search Report of PCT/EP01/05736 dated Oct. 24, 2001.
Finn et al. Differential Response of Delayed Healing . . . Circulation vol. 112 (2005) 270-8.
Greco et al. (Journal of Thermal Analysis and Calorimetry, vol. 72 (2003) 1167-1174.).
Handschumacher, R.E. et al., Purine and Pyrimidine Antimetabolites, Chemotherapeutic Agents, pp. 712-732, Ch. XV1-2, 3rd Edition, Edited by J. Holland, et al., Lea and Febigol, publishers.
Higuchi, Rate of Release of Medicaments from Ointment Bases Containing Drugs in Suspension, Journal of Pharmaceutical Sciences, vol. 50, No. 10, p. 874, Oct. 1961.
Ji, et al., "96-Wellliquid-liquid extraction liquid chromatographytandem mass spectrometry method for the quantitative determination of ABT-578 in human blood samples" Journal of Chromatography B. 805:67-75 (2004).
Ju et al., J. Pharm. Sci. vol. 84, No. 12, 1455-1463.
Khayankarn et al., "Adhesion and Permeability of Polyimide-Clay Nanocomposite Films for Protective Coatings," Journal of Applied Polymer Science, vol. 89,2875-2881 (2003).

(56) References Cited

OTHER PUBLICATIONS

Lawrance et al., "Rectal tacrolimus in the treatment of resistant ulcerative proctitis," Aliment. Pharmacol Ther. 28(10):1214-20 (2008).
Levit, et al., "Supercritical C02 Assisted Electrospinning" J. of Supercritical Fluids, 329-333, vol. 31, Issue 3, (Nov. 2004).
Lewis, D. H., "Controlled Release of Bioactive Agents from Lactides/ Glycolide Polymers" in Biodegradable Polymers as Drug Delivery Systems, Chasin, M. and Langer, R., eds., Marcel Decker (1990).
Luzzi, L.A., J. Phann. Psy. 59:1367 (1970).
Minchin, "Nanomedicine: sizing up targets with nanoparticles," Nature Nanotechnology, vol. 33, Jan. 2008, 12-13.
Mishima et al. "Microencapsulation of Proteins by Rapid Expansion orSupercritical Solution with a Nonsolvent," AIChE J. 2000;46(4):857-65.
Murphy et al., "Chronic prostatitis: management strategies," Drugs 69(1): 71-84 (2009).
O'Donnell et al., "Salvage intravesical therapy with interferon-alpha 2b plus low dose bacillus Calmette-Guerin is effective in patients with superficial bladder cancer in whom bacillus calmette-guerin alone previously failed," Journ. Urology, 166(4): 1300-1304 (2001).
O'Neil et al., "Extracellular matrix binding mixed micelles for drug delivery applications," Journal of Controlled Release 137 (2009) 146-151.
Olbert et al., "In vitro and in vivo effects of CpG-Oligodeoxynucleotides (CpG-ODN) on murine transitional cell carcinoma and on the native murine urinary bladder wall," Anticancer Res. 29(6):2067-2076 (2009).
Park et al., Pharm. Res. (1987) 4(6):457-464.
PCT/EP01/05736 International Preliminary Examination Report dated Jan. 14, 2002.
PCT/EP2000/004658 International Search Report from dated Sep. 15, 2000.
PCT/US06/27321 Written Opinion dated Oct. 16, 2007.
PCT/US09/50883 International Search Report dated Nov. 17, 2009.
PCT/US11/33225 International Search Report and Written Opinion dated Jul. 7, 2011.
PCT/US11/44263 International Search Report and Written Opinion dated Feb. 9, 2012.
PCT/US12/50408 International Search Report dated Oct. 16, 2012.
PCT/US13/41466 International Preliminary Report on Patentability dated Nov. 18, 2014.
PCT/US13/42093 International Preliminary Report on Patentability dated Nov. 25, 2014.
Ristikankare et al., "Sedation, topical pharnygeal anesthesia and cardiorespiratory safety during gastroscopy," J. Clin Gastorenterol. 40(1 ):899-905 (2006).
Salo et al., "Biofilm formation by *Escherichia coli* isolated from patients with urinary tract infections," Clin Nephrol. 71(5):501-507 (2009).
Saxena et al., "Haemodialysis catheter-related bloodstream infections: current treatment options and strategies for prevention," Swiss Med Wkly 135:127-138 (2005).
Schetsky, L. McDonald, "Shape Memory Alloys", Encyclopedia of Chemical Technology (3d Ed), John Wiley & Sons 1982, vol. 20 pp. 726-736.
Scheufler et al., "Crystal Structure of Human Bone Morphogenetic Protein-2 at 2.7 Angstrom resolution," Journal of Molecular Biology, vol. 287, Issue 1, Mar. 1999, pp. 103-115, [retrieved online] at http://www.sciencedirect.comlscience/article/pii/S002283 699925901.
Sumathi et al., "Controlled comparison between betamethasone gel and lidocaine jelly applied over tracheal tube to reduce postoperative sore throat, cough, and hoarseness of voice," Br. J. Anaesth. 100(2):215-218 (2008).
Testa, B., "Prodrug research: futile or fertile?", Biochem. Pharmacal. Dec. 1, 2004;68(11):2097-2106.
Wang et al. "Synthesis, characterization, biodegradation, and drug delivery application of biodegradable lactic/glycolic acid polymers: I. Synthesis and characterization" J. Biomater. Sci. Polymer Edn. 11(3):301-318 (2000).
Extended European Search Report for Application No. 14797966.0 dated Dec. 19, 2016.
Third Party Submission for Application No. JP2015-538086 dated Jun. 4, 2018.
Third Party Submission for Application No. JP2017-130734 dated Nov. 7, 2018, 2 pages.
Search Report from Singapore Application No. 2013054127 dated Jul. 26, 2017, 5 pages.
Handbook of Coronary Stents, Patrick, W. Serruys, University Hospital Dijkzigt, Rotterdam/London 1997.
Farah et al., "Crystalline coating of rapamycin onto a stent: Process development and characterization", International Journal of Pharmaceutics 445, Jan. 2013, pp. 20-28.
Chinese Search Report for Application No. 201910361865.3, dated Apr. 1, 2021, 11 pages.

\* cited by examiner

STENT AND STENT DELIVERY SYSTEM WITH IMPROVED DELIVERABILITY

CROSS REFERENCE

This application claims priority to U.S. Provisional Application No. 61/300,764, filed Feb. 2, 2010. The contents of this application are incorporated herein by reference in their entirety.

This application also relates to U.S. Provisional Application No. 61/325,090, filed Apr. 16, 2010, U.S. Provisional Application No. 61/243,955, filed Sep. 18, 2009, U.S. Provisional Application No. 61/212,964, filed Apr. 17, 2009, U.S. Provisional Application No. 61/165,880, filed Apr. 1, 2009, U.S. Provisional Application No. 61/104,669, filed Oct. 10, 2008, U.S. Provisional Application No. 61/045,928, filed Apr. 17, 2008, U.S. Provisional Application No. 60/912,394, filed Apr. 17, 2007, U.S. Provisional Application No. 60/771,066, filed Feb. 7, 2006, U.S. Provisional Application No. 60/771,725, filed Feb. 8, 2006, U.S. Provisional Application No. 60/745,731, filed Apr. 26, 2006, U.S. Provisional Application No. 60/745,733, filed Apr. 26, 2006, U.S. Provisional Application No. 60/745,733, filed Apr. 26, 2006, U.S. Provisional Application No. 60/752,338, filed Dec. 20, 2005, U.S. Provisional Application No. 60/699,650, filed Jul. 15, 2005. The contents of these applications are incorporated herein by reference in their entirety.

This application also relates to U.S. Provisional Application No. 60/912,408, filed Apr. 17, 2007, U.S. Provisional Application No. 60/912,394, filed Apr. 17, 2007, U.S. Provisional Application No. 60/884,005, filed Jan. 8, 2007, and U.S. Provisional Application No. 60/981,445, filed Oct. 19, 2007. The contents of these applications are incorporated herein by reference in their entirety.

BACKGROUND OF THE INVENTION

Drug-eluting stents are used to address the drawbacks of bare stents, namely to treat restenosis and to promote healing of the vessel after opening the blockage by PCI/stenting. Drug eluting stents are delivered by delivery systems, much like those that deliver bare stents. Some current drug eluting stents can have physical, chemical and therapeutic legacy in the vessel over time. Others may have less legacy, but are not optimized for thickness, deployment flexibility, access to difficult lesions, and minimization of vessel wall intrusion.

SUMMARY OF THE INVENTION

Provided herein are devices and systems having improved stent and/or stent delivery system deliverability and methods related thereto. Some devices and systems herein comprise stents comprising a bioabsorbable polymer and a pharmaceutical or biological agent deposited in powder form.

It is desirable to have a drug-eluting stent with minimal physical, chemical and therapeutic legacy in the vessel after a proscribed period of time. This period of time is based on the effective healing of the vessel after opening the blockage by PCI/stenting (currently believed by leading clinicians to be 6-18 months).

It is also desirable to have drug-eluting stents of minimal cross-sectional thickness for (a) flexibility of deployment (b) access to small vessels (c) minimized intrusion into the vessel wall and blood.

It is also desirable to have drug-eluting stents configured for improved deliverability through the vasculature and to the vessel wall.

It is also desirable to have drug-eluting stent delivery systems configured for improved deliverability through the vasculature and to the vessel wall Provided herein is a stent delivery system comprising: an elongate member having an inflation lumen and a guidewire lumen therein; a balloon having an interior that is in fluid communication with the inflation lumen; and a stent comprising a coating mounted on the balloon, in which for a stent of about 2.25 mm in diameter to about 4.0 mm in diameter by about 9 mm to about 30 mm in length in an expanded state, a stent system trackability expressed as peak force over the track length is at most 1.5 Newtons.

Provided herein is a stent delivery system comprising: an elongate member having an inflation lumen and a guidewire lumen therein; a balloon having an interior that is in fluid communication with the inflation lumen; and a stent comprising a coating mounted on the balloon, in which for a stent of about 2.25 mm in diameter to about 4.0 mm in diameter by about 9 mm to about 30 mm in length in an expanded state, a stent system trackability expressed as mean force over the track length is at most 0.5 Newtons.

In some embodiments, stent system trackability is tested according to Tortuosity test 1. In some embodiments, stent system trackability is tested according to Tortuosity test 2.

In some embodiments, the balloon comprises a polymer, and the stent mounted on the balloon has a crossing profile of at most 1.12 mm.

In some embodiments, the polymer of the balloon comprises polyamide. In some embodiments, the polymer of the balloon comprises at least one of: polyethylene, polyethylene terephthalate (PET), high density polyethylene (HDPE), Arnitel, Hyrtrel, polyetherether ketone (PEEK), urethane, polyurethane, urethane elastomer, nylon, polyamide, polyether block amide (PEBAX), a block copolymer of any polymer listed herein, Teflon, polyolefin, and a thermoplastic elastomer.

In some embodiments, the coating is at most 20 micrometers in thickness and comprises a polymer. In some embodiments, the polymer of the coating is hydrophilic. In some embodiments, the hydrophilic polymer of the coating comprises PLGA. In some embodiments, the polymer of the coating is bioaborbable. In some embodiments, the polymer of the coating comprises at least one of PLGA, a copolymer comprising PLGA (i.e. a PLGA copolymer), a PLGA copolymer with a ratio of about 40:60 to about 60:40, a PLGA copolymer with a ratio of about 70:30 to about 90:10, a PLGA copolymer having a molecular weight of about 10 kD, a PLGA copolymer having a molecular weight of about 19 kD, PGA poly(glycolide), LPLA poly(l-lactide), DLPLA poly(dl-lactide), PCL poly(e-caprolactone) PDO, poly(dioxolane) PGA-TMC, 85/15 DLPLG p(dl-lactide-co-glycolide), 75/25 DLPL, 65/35 DLPLG, 50/50 DLPLG, TMC poly(trimethylcarbonate), p(CPP:SA) poly(1,3-bis-p-(carboxyphenoxy)propane-co-sebacic acid), and a combination thereof.

In some embodiments, the coating comprises a pharmaceutical agent. In some embodiments, the pharmaceutical agent comprises at least one of rapamycin, a prodrug, a derivative, an analog, a hydrate, an ester, and a salt thereof; wherein at least a portion of the pharmaceutical agent is in crystalline form. In some embodiments, the pharmaceutical agent comprises one or more of rapamycin, biolimus (biolimus A9), 40-O-(2-Hydroxyethyl)rapamycin (everolimus), 40-O-Benzyl-rapamycin, 40-O-(4'-Hydroxymethyl)benzyl-rapamycin, 40-O-[4'-(1,2-Dihydroxyethyl)]benzyl-rapamycin, 40-O-Allyl-rapamycin, 40-O-[3'-(2,2-Dimethyl-1,3-dioxolan-4(S)-yl)-prop-2'-en-1'-yl]-rapamycin, (2':E,4'S)-40-O-(4',5'-Dihydroxypent-2'-en-1'-yl)-rapamycin 40-O-(2-Hydroxy)ethoxycar-bonylmethyl-rapamycin, 40-O-(3-Hydroxy)propyl-rapamycin 4O—O-(6-Hydroxy)hexyl-rapamycin 40-O-[2-(2-Hydroxy)ethoxy]ethyl-rapamycin 4O—O-[(3S)-2,2-Dimethyldioxolan-3-yl]methyl-rapamycin, 40-O-[(2S)-2,3-Dihydroxyprop-1-yl]-rapamycin, 4O—O-(2-Acetoxy)ethyl-rapamycin 4O—O-(2-Nicotinoyloxy)ethyl-rapamycin, 4O—O-[2-(N-Morpholino)acetoxy]ethyl-rapamycin 4O—O-(2-N-Imidazolylacetoxy)ethyl-rapamycin, 40-O-[2-(N-Methyl-N'-piperazinyl)acetoxy]ethyl-rapamycin, 39-O-Desmethyl-39,40-O,O-ethylene-rapamycin, (26R)-26-Dihydro-40-O-(2-hydroxy)ethyl-rapamycin, 28-O-Methyl-rapamycin, 4O—O-(2-Aminoethyl)-rapamycin, 4O—O-(2-Acetaminoethyl)-rapamycin 4O—O-(2-Nicotinamidoethyl)-rapamycin, 4O—O-(2-(N-Methyl-imidazo-2'-ylcarbethoxamido)ethyl)-rapamycin, 4O—O-(2-Ethoxycarbonylaminoethyl)-rapamycin, 40-O-(2-Tolylsulfonamidoethyl)-rapamycin, 40-O-[2-(4',5'-Dicarboethoxy-1',2',3'-triazol-1'-yl)-ethyl]-rapamycin, 42-Epi-(tetrazolyl)rapamycin (tacrolimus), 42-[3-hydroxy-2-(hydroxymethyl)-2-methylpropanoate]rapamycin (temsirolimus), (42S)-42-Deoxy-42-(1H-tetrazol-1-yl)-rapamycin (zotarolimus), picrolimus, novolimus, myolimus, and salts, derivatives, isomers, racemates, diastereoisomers, prodrugs, hydrate, ester, or analogs thereof.

In some embodiments, an uncoated stent strut thickness is at most 64 micrometers.

In some embodiments, stent system trackability expressed as peak force over the track length is at most 1 Newton. In some embodiments, stent system trackability expressed as mean force over the track length is at most 0.3 Newtons.

In some embodiments, the stent has a closed cell design. In some embodiments, the stent has an open cell design. In some embodiments, the stent has a hybrid of an open and a closed cell design.

In some embodiments, the elongate member has a useable length of about 140 centimeters.

In some embodiments, the stent system trackability is achieved with at least one of: at most 5% coating delamination, at most 10% coating delamination, at most 15% coating delamination, and at most 20% coating delamination. In some embodiments, the coating delamination is tested by visual inspection.

In some embodiments, the stent system trackability is achieved with at least one of: at most 5% coating cracking, at most 10% coating cracking, at most 15% coating cracking, and at most 20% coating cracking. In some embodiments, the coating cracking is tested by visual inspection.

Provided herein is a stent delivery system comprising: an elongate member having an inflation lumen and a guidewire lumen therein; a balloon having an interior that is in fluid communication with the inflation lumen; and a stent comprising a coating mounted on the balloon, in which a stent of about 2.25 mm in diameter to about 4.0 mm in diameter by about 9 mm to about 30 mm in length in an expanded state has a stent system pushability ((Fdist/Fprox)×100%) of at most 18%.

In some embodiments, the stent system pushability is measured according to Tortuosity Test 2.

In some embodiments, the balloon comprises a polymer, and the stent mounted on the balloon has a crossing profile of at most 1.06 mm for a 2.25 diameter balloon, at most 1.09 mm for a 2.5 diameter balloon, at most 1.11 mm for a 2.75 diameter balloon, at most 1.12 mm for a 3.0 diameter balloon, at most 1.18 mm for a 3.5 diameter balloon, and at most 1.35 mm for a 4.0 diameter balloon.

In some embodiments, the polymer of the balloon comprises polyamide. In some embodiments, the polymer of the balloon comprises at least one of: polyethylene, polyethylene terephthalate (PET), high density polyethylene (HDPE), Arnitel, Hyrtrel, polyetherether ketone (PEEK), urethane, polyurethane, urethane elastomer, nylon, polyamide, polyether block amide (PEBAX), a block copolymer of any polymer listed herein, Teflon, polyolefin, and a thermoplastic elastomer.

In some embodiments, the coating is at most 20 micrometers in thickness and comprises a polymer. In some embodiments, the polymer of the coating is hydrophilic. In some embodiments, the hydrophilic polymer of the coating comprises PLGA. In some embodiments, the polymer of the coating is bioabsorbable. In some embodiments, the polymer of the coating comprises at least one of PLGA, a copolymer comprising PLGA (i.e. a PLGA copolymer), a PLGA copolymer with a ratio of about 40:60 to about 60:40, a PLGA copolymer with a ratio of about 70:30 to about 90:10, a PLGA copolymer having a molecular weight of about 10 kD, a PLGA copolymer having a molecular weight of about 19 kD, PGA poly(glycolide), LPLA poly(l-lactide), DLPLA poly(dl-lactide), PCL poly(e-caprolactone) PDO, poly(dioxolane) PGA-TMC, 85/15 DLPLG p(dl-lactide-co-glycolide), 75/25 DLPL, 65/35 DLPLG, 50/50 DLPLG, TMC poly(trimethylcarbonate), p(CPP:SA) poly(1,3-bis-p-(carboxyphenoxy)propane-co-sebacic acid), and a combination thereof.

In some embodiments, the coating comprises a pharmaceutical agent. In some embodiments, the pharmaceutical agent comprises at least one of rapamycin, a prodrug, a derivative, an analog, a hydrate, an ester, and a salt thereof; wherein at least a portion of the pharmaceutical agent is in crystalline form. In some embodiments, the pharmaceutical agent comprises one or more of rapamycin, biolimus (biolimus A9), 40-O-(2-Hydroxyethyl)rapamycin (everolimus), 40-O-Benzyl-rapamycin, 40-O-(4'-Hydroxymethyl)benzyl-rapamycin, 40-O-[4'-(1,2-Dihydroxyethyl)]benzyl-rapamycin, 40-O-Allyl-rapamycin, 40-O-[3'-(2,2-Dimethyl-1,3-dioxolan-4(S)-yl)-prop-2'-en-1'-yl]-rapamycin, (2':E,4'S)-40-O-(4',5'-Dihydroxypent-2'-en-1'-yl)-rapamycin 40-O-(2-Hydroxy)ethoxycar-bonylmethyl-rapamycin, 40-O-(3-Hydroxy)propyl-rapamycin 4O—O-(6-Hydroxy)hexyl-rapamycin 40-O-[2-(2-Hydroxy)ethoxy]ethyl-rapamycin 4O—O-[(3S)-2,2-Dimethyldioxolan-3-yl]methyl-rapamycin, 40-O-[(2S)-2,3-Dihydroxyprop-1-yl]-rapamycin, 4O—O-(2-Acetoxy)ethyl-rapamycin 4O—O-(2-Nicotinoyloxy)ethyl-rapamycin, 4O—O-[2-(N-Morpholino)acetoxy]ethyl-rapamycin 4O—O-(2-N-Imidazolylacetoxy)ethyl-rapamycin, 40-O-[2-(N-Methyl-N-piperazinyl)acetoxy]ethyl-rapamycin, 39-O-Desmethyl-39,40-O,O-ethylene-rapamycin, (26R)-26-Dihydro-40-O-(2-hydroxy)ethyl-rapamycin, 28-O-Methyl-rapamycin, 4O—O-(2-Aminoethyl)-rapamycin, 4O—O-(2-Acetaminoethyl)-rapamycin 4O—O-(2-Nicotinamidoethyl)-rapamycin, 4O—O-(2-(N-Methyl-imidazo-2'-ylcarbethoxamido)ethyl)-rapamycin, 4O—O-(2-Ethoxycarbonylaminoethyl)-rapamycin, 40-O-(2-Tolylsulfonamidoethyl)-rapamycin, 40-O-[2-(4',5'-Dicarboethoxy-1',2',3'-triazol-1'-yl)-ethyl]-rapamycin, 42-Epi-(tetrazolyl)rapamycin (tacrolimus), 42-[3-hydroxy-2-(hydroxymethyl)-2-methylpropanoate]rapamycin (temsirolimus), (42S)-42-Deoxy-42-(1H-tetrazol-1-yl)-rapamycin (zotarolimus), picrolimus, novolimus, myolimus, and salts, derivatives, isomers, racemates, diastereoisomers, prodrugs, hydrate, ester, or analogs thereof.

In some embodiments, an uncoated stent strut thickness of the stent is at most 64 micrometers.

In some embodiments, the stent has a closed cell design. In some embodiments, the stent has an open cell design. In some embodiments, the stent has a hybrid of an open and a closed cell design.

In some embodiments, the elongate member has a useable length of about 140 centimeters.

In some embodiments, the stent system pushability is achieved with at least one of: at most 5% coating delamination, at most 10% coating delamination, at most 15% coating delamination, and at most 20% coating delamination. In some embodiments, the coating delamination is tested by visual inspection.

In some embodiments, the stent system pushability is achieved with at least one of: at most 5% coating cracking, at most 10% coating cracking, at most 15% coating cracking, and at most 20% coating cracking. In some embodiments, the coating delamination is tested by visual inspection.

Provided herein is a stent delivery system comprising: an elongate member having an inflation lumen and a guidewire lumen therein; a balloon having an interior that is in fluid communication with the inflation lumen; and a stent comprising a coating mounted on the balloon, in which a stent of about 2.25 mm in diameter to about 4.0 mm in diameter by about 9 mm to about 30 mm in length in an expanded state has a stent system crossability measured as peak cross force of at most 0.15 Newtons.

Provided herein is a stent delivery system comprising: an elongate member having an inflation lumen and a guidewire lumen therein; a balloon having an interior that is in fluid communication with the inflation lumen; and a stent comprising a coating mounted on the balloon, in which a stent of about 2.25 mm in diameter to about 4.0 mm in diameter by about 9 mm to about 30 mm in length in an expanded state has a stent system crossability measured as mean cross force of less than 0.04 Newtons.

In some embodiments, the tortuosity fixture and the simulated lesion are configured according to tortuosity test 1. Provided herein is a the tortuosity fixture and the simulated lesion are configured according to tortuosity test 2.

In some embodiments, the balloon comprises a polymer, and the stent mounted on the balloon has a crossing profile of at most 1.12 mm.

In some embodiments, the polymer of the balloon comprises polyamide. In some embodiments, the polymer of the balloon comprises at least one of: polyethylene, polyethylene terephthalate (PET), high density polyethylene (HDPE), Arnitel, Hyrtrel, polyetherether ketone (PEEK), urethane, polyurethane, urethane elastomer, nylon, polyamide, polyether block amide (PEBAX), a block copolymer of any polymer listed herein, Teflon, polyolefin, and a thermoplastic elastomer.

In some embodiments, the coating is at most 20 micrometers in thickness and comprises a polymer. In some embodiments, the polymer of the coating is hydrophilic. In some embodiments, the hydrophilic polymer of the coating comprises PLGA. In some embodiments, the polymer of the coating is bioabsorbable. In some embodiments, the polymer of the coating comprises at least one of PLGA, a copolymer comprising PLGA (i.e. a PLGA copolymer), a PLGA copolymer with a ratio of about 40:60 to about 60:40, a PLGA copolymer with a ratio of about 70:30 to about 90:10, a PLGA copolymer having a molecular weight of about 10 kD, a PLGA copolymer having a molecular weight of about 19 kD, PGA poly(glycolide), LPLA poly(l-lactide), DLPLA poly(dl-lactide), PCL poly(e-caprolactone) PDO, poly(dioxolane) PGA-TMC, 85/15 DLPLG p(dl-lactide-co-glycolide), 75/25 DLPL, 65/35 DLPLG, 50/50 DLPLG, TMC poly(trimethylcarbonate), p(CPP:SA) poly(1,3-bis-p-(carboxyphenoxy)propane-co-sebacic acid), and a combination thereof.

In some embodiments, the coating comprises a pharmaceutical agent. In some embodiments, the pharmaceutical agent comprises at least one of rapamycin, a prodrug, a derivative, an analog, a hydrate, an ester, and a salt thereof; wherein at least a portion of the pharmaceutical agent is in crystalline form. In some embodiments, the pharmaceutical agent comprises one or more of rapamycin, biolimus (biolimus A9), 40-O-(2-Hydroxyethyl)rapamycin (everolimus), 40-O-Benzyl-rapamycin, 40-O-(4'-Hydroxymethyl)benzyl-rapamycin, 40-O-[4'-(1,2-Dihydroxyethyl)]benzyl-rapamycin, 40-O-Allyl-rapamycin, 40-O-[3'-(2,2-Dimethyl-1,3-dioxolan-4(S)-yl)-prop-2'-en-1'-yl]-rapamycin, (2':E,4'S)-40-O-(4',5'-Dihydroxypent-2'-en-1'-yl)-rapamycin 40-O-(2-Hydroxy)ethoxycar-bonylmethyl-rapamycin, 40-O-(3-Hydroxy)propyl-rapamycin 4O—O-(6-Hydroxy)hexyl-rapamycin 40-O-[2-(2-Hydroxy)ethoxy]ethyl-rapamycin 4O—O-[(3S)-2,2-Dimethyldioxolan-3-yl]methyl-rapamycin, 40-O-[(2S)-2,3-Dihydroxyprop-1-yl]-rapamycin, 4O—O-(2-Acetoxy)ethyl-rapamycin 4O—O-(2-Nicotinoyloxy)ethyl-rapamycin, 4O—O-[2-(N-Morpholino)acetoxy]ethyl-rapamycin 4O—O-(2-N-Imidazolylacetoxy)ethyl-rapamycin, 40-O-[2-(N-Methyl-N'-piperazinyl)acetoxy]ethyl-rapamycin, 39-O-Desmethyl-39,40-O,O-ethylene-rapamycin, (26R)-26-Dihydro-40-O-(2-hydroxy)ethyl-rapamycin, 28-O-Methyl-rapamycin, 4O—O-(2-Aminoethyl)-rapamycin, 4O—O-(2-Acetaminoethyl)-rapamycin 4O—O-(2-Nicotinamidoethyl)-rapamycin, 4O—O-(2-(N-Methyl-imidazo-2'-ylcarbethoxamido)ethyl)-rapamycin, 4O—O-(2-Ethoxycarbonylaminoethyl)-rapamycin, 40-O-(2-Tolylsulfonamidoethyl)-rapamycin, 40-O-[2-(4',5'-Dicarboethoxy-1',2',3'-triazol-1'-yl)-ethyl]-rapamycin, 42-Epi-(tetrazolyl)rapamycin (tacrolimus), 42-[3-hydroxy-2-(hydroxymethyl)-2-methylpropanoate]rapamycin (temsirolimus), (42S)-42-Deoxy-42-(1H-tetrazol-1-yl)-rapamycin (zotarolimus), picrolimus, novolimus, myolimus, and salts, derivatives, isomers, racemates, diastereoisomers, prodrugs, hydrate, ester, or analogs thereof.

In some embodiments, an uncoated stent strut thickness of the stent is at most 64 micrometers.

In some embodiments, the stent system crossability expressed as peak cross force is at most 0.1 Newton. In some embodiments, the stent system crossability expressed as mean cross force is at most 0.03 Newtons.

In some embodiments, the stent has a closed cell design. In some embodiments, the stent has an open cell design. In some embodiments, the stent has a hybrid of an open and a closed cell design.

In some embodiments, the elongate member has a useable length of about 140 centimeters.

In some embodiments, the stent system crossability is achieved with at least one of: at most 5% coating delamination, at most 10% coating delamination, at most 15% coating delamination, and at most 20% coating delamination. In some embodiments, the coating delamination is tested by visual inspection.

In some embodiments, the stent system crossability is achieved with at least one of: at most 5% coating cracking, at most 10% coating cracking, at most 15% coating cracking, and at most 20% coating cracking. In some embodiments, the coating delamination is tested by visual inspection.

Provided herein is a method of concurrently delivering a first coated stent to a first target location in a body and a second coated stent to second target location in the body, the method comprising: advancing a first stent delivery system through a guiding catheter in which the first stent delivery system comprises a first elongate member having a first inflation lumen and a first guidewire lumen therein, a first balloon having a first interior that is in fluid communication with the first inflation lumen; and a first coated stent mounted on the first balloon, and advancing a second stent delivery system through the guiding catheter in which the second stent delivery system comprises a second elongate member having a second inflation lumen and a second guidewire lumen therein, a second balloon having a second interior that is in fluid communication with the second inflation lumen; and a second coated stent mounted on the second balloon, wherein the advancing of the second stent delivery system is performed while the first stent delivery system is also in the guiding catheter.

In some embodiments, the first balloon comprises a polymer, and the first coated stent mounted on the balloon has a crossing profile of at most 1.06 mm for a 2.25 mm diameter stent, 1.09 mm for a 2.5 mm diameter stent, 1.11 mm for a 2.75 mm diameter stent, 1.12 mm for a 3.0 mm diameter stent, 1.18 mm for a 3.5 mm diameter stent, and 1.25 mm for a 4.0 mm diameter stent, wherein the diameter is an expanded stent diameter.

In some embodiments, the polymer of the first balloon comprises polyamide. In some embodiments, the polymer of the first balloon comprises at least one of: polyethylene, polyethylene terephthalate (PET), high density polyethylene (HDPE), Arnitel, Hyrtrel, polyetherether ketone (PEEK), urethane, polyurethane, urethane elastomer, nylon, polyamide, polyether block amide (PEBAX), a block copolymer of any polymer listed herein, Teflon, polyolefin, and a thermoplastic elastomer.

In some embodiments, the first coated stent comprises a first coating which is at most 20 micrometers in thickness and comprises a polymer. In some embodiments, the first coating is hydrophilic. In some embodiments, the hydrophilic polymer comprises PLGA. In some embodiments, the polymer of the first coating is bioabsorbable. In some embodiments, the polymer of the first coating comprises at least one of PLGA, a copolymer comprising PLGA (i.e. a PLGA copolymer), a PLGA copolymer with a ratio of about 40:60 to about 60:40, a PLGA copolymer with a ratio of about 70:30 to about 90:10, a PLGA copolymer having a molecular weight of about 10 kD, a PLGA copolymer having a molecular weight of about 19 kD, PGA poly(glycolide), LPLA poly(l-lactide), DLPLA poly(dl-lactide), PCL poly(e-caprolactone) PDO, poly(dioxolane) PGA-TMC, 85/15 DLPLG p(dl-lactide-co-glycolide), 75/25 DLPL, 65/35 DLPLG, 50/50 DLPLG, TMC poly(trimethylcarbonate), p(CPP:SA) poly(1,3-bis-p-(carboxyphenoxy)propane-co-sebacic acid), and a combination thereof.

In some embodiments, the second balloon comprises a polymer, and the second coated stent mounted on the balloon has a crossing profile of at most 1.06 mm for a 2.25 mm diameter stent, 1.09 mm for a 2.5 mm diameter stent, 1.11 mm for a 2.75 mm diameter stent, 1.12 mm for a 3.0 mm diameter stent, 1.18 mm for a 3.5 mm diameter stent, and 1.25 mm for a 4.0 mm diameter stent, wherein the diameter is an expanded stent diameter.

In some embodiments, the polymer of the second balloon comprises polyamide. In some embodiments, the polymer of the second balloon comprises at least one of: polyethylene, polyethylene terephthalate (PET), high density polyethylene (HDPE), Arnitel, Hyrtrel, polyetherether ketone (PEEK), urethane, polyurethane, urethane elastomer, nylon, polyamide, polyether block amide (PEBAX), a block copolymer of any polymer listed herein, Teflon, polyolefin, and a thermoplastic elastomer.

In some embodiments, the second coated stent comprises a second coating which is at most 20 micrometers in thickness and comprises a polymer. In some embodiments, the polymer of the second coating is hydrophilic. In some embodiments, the hydrophilic polymer comprises PLGA. In some embodiments, the polymer of the second coating is bioabsorbable. In some embodiments, the polymer of the second coating comprises at least one of PLGA, a copolymer comprising PLGA (i.e. a PLGA copolymer), a PLGA copolymer with a ratio of about 40:60 to about 60:40, a PLGA copolymer with a ratio of about 70:30 to about 90:10, a PLGA copolymer having a molecular weight of about 10 kD, a PLGA copolymer having a molecular weight of about 19 kD, PGA poly(glycolide), LPLA poly(l-lactide), DLPLA poly(dl-lactide), PCL poly(e-caprolactone) PDO, poly(dioxolane) PGA-TMC, 85/15 DLPLG p(dl-lactide-co-glycolide), 75/25 DLPL, 65/35 DLPLG, 50/50 DLPLG, TMC poly(trimethylcarbonate), p(CPP:SA) poly(1,3-bis-p-(carboxyphenoxy)propane-co-sebacic acid), and a combination thereof.

In some embodiments, an uncoated stent strut thickness of the first coated stent is at most 64 micrometers. In some embodiments, an uncoated stent strut thickness of the second coated stent is at most 64 micrometers.

In some embodiments, the first stent delivery system and the second stent delivery system are configured to be simultaneously advanced distally.

In some embodiments, the first stent delivery system and the second stent delivery system are configured to be simultaneously withdrawn proximally.

In some embodiments, the first stent delivery system and the second stent delivery system each are manipulable when both systems are within the guiding catheter.

In some embodiments, the guiding catheter is a 7F guiding catheter.

In some embodiments, the first elongate member has a useable length of about 140 centimeters. In some embodiments, the second elongate member has a useable length of about 140 centimeters.

Provided herein is a stent delivery system comprising: an elongate member having an inflation lumen and a guidewire lumen therein; a balloon having an interior that is in fluid communication with the inflation lumen; and a stent comprising a coating mounted on the balloon, wherein when at least a portion of the stent system that includes the mounted stent is tested using Lubricity Test 1, the lubricity is at most 20 g.

In some embodiments, at least the portion of the stent system that includes the mounted stent is tested using Lubricity Test 1 the lubricity is at most 15 g.

In some embodiments, the balloon comprises a polymer, and the stent mounted on the balloon has a crossing profile of at most 1.12 mm.

In some embodiments, the polymer of the balloon comprises polyamide. In some embodiments, the polymer of the balloon comprises at least one of: polyethylene, polyethylene terephthalate (PET), high density polyethylene (HDPE), Arnitel, Hyrtrel, polyetherether ketone (PEEK), urethane, polyurethane, urethane elastomer, nylon, polyamide, polyether block amide (PEBAX), a block copolymer of any polymer listed herein, Teflon, polyolefin, and a thermoplastic elastomer.

In some embodiments, the coating is at most 20 micrometers in thickness and comprises a polymer. In some embodiments, the polymer of the coating is hydrophilic. In some embodiments, the hydrophilic polymer of the coating comprises PLGA. In some embodiments, the polymer of the coating is bioabsorbable. In some embodiments, the polymer of the coating comprises at least one of PLGA, a copolymer comprising PLGA (i.e. a PLGA copolymer), a PLGA copolymer with a ratio of about 40:60 to about 60:40, a PLGA copolymer with a ratio of about 70:30 to about 90:10, a PLGA copolymer having a molecular weight of about 10 kD, a PLGA copolymer having a molecular weight of about 19 kD, PGA poly(glycolide), LPLA poly(l-lactide), DLPLA poly(dl-lactide), PCL poly(e-caprolactone) PDO, poly(dioxolane) PGA-TMC, 85/15 DLPLG p(dl-lactide-co-glycolide), 75/25 DLPL, 65/35 DLPLG, 50/50 DLPLG, TMC poly(trimethylcarbonate), p(CPP:SA) poly(1,3-bis-p-(carboxyphenoxy)propane-co-sebacic acid), and a combination thereof.

In some embodiments, the coating comprises a pharmaceutical agent. In some embodiments, the pharmaceutical agent comprises at least one of rapamycin, a prodrug, a derivative, an analog, a hydrate, an ester, and a salt thereof; wherein at least a portion of the pharmaceutical agent is in crystalline form. In some embodiments, the pharmaceutical agent comprises one or more of rapamycin, biolimus (biolimus A9), 40-O-(2-Hydroxyethyl)rapamycin (everolimus), 40-O-Benzyl-rapamycin, 40-O-(4'-Hydroxymethyl)benzyl-rapamycin, 40-O-[4'-(1,2-Dihydroxyethyl)]benzyl-rapamycin, 40-O-Allyl-rapamycin, 40-O-[3'-(2,2-Dimethyl-1,3-dioxolan-4(S)-yl)-prop-2'-en-1'-yl]-rapamycin, (2':E,4'S)-40-O-(4',5'-Dihydroxypent-2'-en-1'-yl)-rapamycin 40-O-(2-Hydroxy)ethoxycar-bonylmethyl-rapamycin, 40-O-(3-Hydroxy)propyl-rapamycin 4O—O-(6-Hydroxy)hexyl-rapamycin 40-O-[2-(2-Hydroxy)ethoxy]ethyl-rapamycin 4O—O-[(3S)-2,2-Dimethyldioxolan-3-yl]methyl-rapamycin, 40-O-[(2S)-2,3-Dihydroxyprop-1-yl]-rapamycin, 4O—O-(2-Acetoxy)ethyl-rapamycin 4O—O-(2-Nicotinoyloxy)ethyl-rapamycin, 4O—O-[2-(N-Morpholino)acetoxy]ethyl-rapamycin 4O—O-(2-N-Imidazolylacetoxy)ethyl-rapamycin, 40-O-[2-(N-Methyl-N'-piperazinyl)acetoxy]ethyl-rapamycin, 39-O-Desmethyl-39,40-O,O-ethylene-rapamycin, (26R)-26-Dihydro-40-O-(2-hydroxy)ethyl-rapamycin, 28-O-Methyl-rapamycin, 4O—O-(2-Aminoethyl)-rapamycin, 4O—O-(2-Acetaminoethyl)-rapamycin 4O—O-(2-Nicotinamidoethyl)-rapamycin, 4O—O-(2-(N-Methyl-imidazo-2'-ylcarbethoxamido)ethyl)-rapamycin, 4O—O-(2-Ethoxycarbonylaminoethyl)-rapamycin, 40-O-(2-Tolylsulfonamidoethyl)-rapamycin, 40-O-[2-(4',5'-Dicarboethoxy-1',2',3'-triazol-1'-yl)-ethyl]-rapamycin, 42-Epi-(tetrazolyl)rapamycin (tacrolimus), 42-[3-hydroxy-2-(hydroxymethyl)-2-methylpropanoate]rapamycin (temsirolimus), (42S)-42-Deoxy-42-(1H-tetrazol-1-yl)-rapamycin (zotarolimus), picrolimus, novolimus, myolimus, and salts, derivatives, isomers, racemates, diastereoisomers, prodrugs, hydrate, ester, or analogs thereof.

In some embodiments, at least the portion of the stent system that includes the mounted stent is tested using Lubricity Test 1 and has a lubricity of at least one of: at most about 14 g, at most about 13 g, at most about 12 g, at most about 11 g at most about 10 g, at most about 9 g, at most about 8 g, at most about 7 g, at most about 6 g, and at most about 5 g.

In some embodiments, the stent has a closed cell design. In some embodiments, the stent has an open cell design. In some embodiments, the stent has a hybrid of an open and a closed cell design.

In some embodiments, the elongate member has a useable length of about 140 centimeters.

Provided herein is a stent comprising: a coating of at most 20 micrometers thickness comprising polymer and a pharmaceutical agent, in which the coated stent comprises a surface hardness (Hf) of at most 2 GPa when measured by Nanoindentation Test 1.

Provided herein is a stent comprising: a coating of at most 20 micrometers thickness comprising polymer and a pharmaceutical agent, in which the coated stent tested in a wetted state comprises a surface hardness (Hf) of at least one of: at most 2 GPa, at most 1.8 GPa, at most 1.6 GPa, at most 1.4 GPa, at most 1.2 GPa, at most 1 GPa, at most 0.8 GPa, at most 0.75 GPa, and at most 0.5 GPa, when measured by Nanoindentation Test 1.

In some embodiments, the polymer comprises PLGA. In some embodiments, the polymer is hydrophilic. In some embodiments, the polymer is bioabsorbable. In some embodiments, the polymer comprises at least one of PLGA, a copolymer comprising PLGA (i.e. a PLGA copolymer), a PLGA copolymer with a ratio of about 40:60 to about 60:40, a PLGA copolymer with a ratio of about 70:30 to about 90:10, a PLGA copolymer having a molecular weight of about 10 kD, a PLGA copolymer having a molecular weight of about 19 kD, PGA poly(glycolide), LPLA poly(l-lactide), DLPLA poly(dl-lactide), PCL poly(e-caprolactone) PDO, poly(dioxolane) PGA-TMC, 85/15 DLPLG p(dl-lactide-co-glycolide), 75/25 DLPL, 65/35 DLPLG, 50/50 DLPLG, TMC poly(trimethylcarbonate), p(CPP:SA) poly(1,3-bis-p-(carboxyphenoxy)propane-co-sebacic acid), and a combination thereof.

In some embodiments, the uncoated stent strut thickness is at most 64 micrometers.

T In some embodiments, the coating comprises a pharmaceutical agent. In some embodiments, the pharmaceutical agent comprises at least one of rapamycin, a prodrug, a derivative, an analog, a hydrate, an ester, and a salt thereof; wherein at least a portion of the pharmaceutical agent is in crystalline form. In some embodiments, the pharmaceutical agent comprises one or more of rapamycin, biolimus (biolimus A9), 40-O-(2-Hydroxyethyl)rapamycin (everolimus), 40-O-Benzyl-rapamycin, 40-O-(4'-Hydroxymethyl)benzyl-rapamycin, 40-O-[4'-(1,2-Dihydroxyethyl)]benzyl-rapamycin, 40-O-Allyl-rapamycin, 40-O-[3'-(2,2-Dimethyl-1,3-dioxolan-4(S)-yl)-prop-2'-en-1'-yl]-rapamycin, (2':E,4'S)-40-O-(4',5'-Dihydroxypent-2'-en-1'-yl)-rapamycin 40-O-(2-Hydroxy)ethoxycar-bonylmethyl-rapamycin, 40-O-(3-Hydroxy)propyl-rapamycin 4O—O-(6-Hydroxy)hexyl-rapamycin 40-O-[2-(2-Hydroxy)ethoxy]ethyl-rapamycin 4O—O-[(3S)-2,2-Dimethyldioxolan-3-yl]methyl-rapamycin, 40-O-[(2S)-2,3-Dihydroxyprop-1-yl]-rapamycin, 4O—O-(2-Acetoxy)ethyl-rapamycin 4O—O-(2-Nicotinoyloxy)ethyl-rapamycin, 4O—O-[2-(N-Morpholino)acetoxy]ethyl-rapamycin 4O—O-(2-N-Imidazolylacetoxy)ethyl-rapamycin, 40-O-[2-(N-Methyl-N-piperazinyl)acetoxy]ethyl-rapamycin, 39-O-Desmethyl-39,40-O,O-ethylene-rapamycin, (26R)-26-Dihydro-40-O-(2-hydroxy)ethyl-rapamycin, 28-O-Methyl-rapamycin, 4O—O-(2-Aminoethyl)-rapamycin, 4O—O-(2-Acetaminoethyl)-rapamycin 4O—O-(2-Nicotinamidoethyl)-rapamycin, 4O—O-(2-(N-Methyl-imidazo-2'-ylcarbethoxamido)ethyl)-rapamycin, 4O—O-(2-Ethoxycarbonylaminoethyl)-rapamycin, 40-O-(2-Tolylsulfonamidoethyl)-rapamycin, 40-O-[2-(4',5'-Dicarboethoxy-1',2',3'-triazol-1'-yl)-ethyl]-rapamycin, 42-Epi-(tetrazolyl)rapamycin (tacrolimus), 42-[3-hydroxy-2-(hydroxymethyl)-2-methylpropanoate]rapamycin (temsirolimus), (42S)-42-Deoxy-42-(1H-tetrazol-1-yl)-rapamycin (zotarolimus), picrolimus, novolimus, myolimus, and salts, derivatives, isomers, racemates, diastereoisomers, prodrugs, hydrate, ester, or analogs thereof.

In some embodiments, the coated stent comprises a surface hardness (Hf) of at least one of: at most 1.5 GPa, at most 1.4 GPa, at most 1.3 GPa, at most 1.2 GPa, at most 1.1 GPa, at most 1.0 GPa, at most 0.9 GPa, at most 0.8 GPa, at most 0.7 GPa, at most 0.6 GPa, at most 0.5 GPa, at most 0.4 GPa, at most 0.3 GPa, at most 0.2 GPa, when measured by Nanoindentation Test 1.

In some embodiments, the coated stent is wetted in a saline solution for about 5 minutes prior to surface hardness (Hf) testing. In some embodiments, the coated stent is wetted in a saline solution for about 4 hours prior to surface hardness (Hf) testing.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
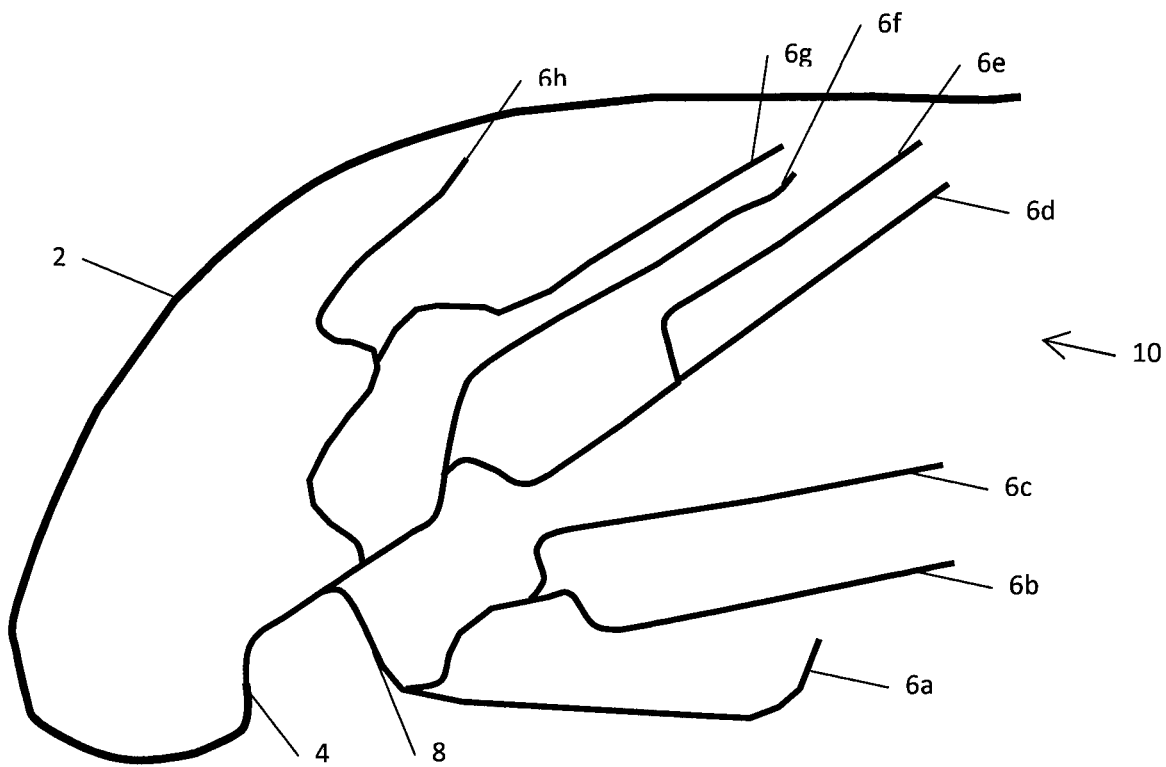
FIG. 1 depicts an in-vitro tortuosity fixture, such as is used on Tortuosity Test 2, showing various simulated paths of the coronary vasculature.

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments contemplated herein will be apparent to those skilled in the art in light of the instant disclosure, which do not depart from the instant invention. Hence, the following specification is intended to illustrate selected embodiments of the invention, and not to exhaustively specify all permutations, combinations and variations thereof.

Definitions

As used in the present specification, the following words and phrases are generally intended to have the meanings as set forth below, except to the extent that the context in which they are used indicates otherwise.

"Substrate" as used herein, refers to any surface upon which it is desirable to deposit a coating comprising a polymer and a pharmaceutical or biological agent, wherein the coating process does not substantially modify the morphology of the pharmaceutical agent or the activity of the biological agent. Biomedical implants are of particular interest for the present invention; however the present invention is not intended to be restricted to this class of substrates. Those of skill in the art will appreciate alternate substrates that could benefit from the coating process described herein, such as pharmaceutical tablet cores, as part of an assay apparatus or as components in a diagnostic kit (e.g. a test strip).

"Biomedical implant" as used herein refers to any implant for insertion into the body of a human or animal subject, including but not limited to stents (e.g., coronary stents, vascular stents including peripheral stents and graft stents, urinary tract stents, urethral/prostatic stents, rectal stent, oesophageal stent, biliary stent, pancreatic stent), electrodes, catheters, leads, implantable pacemaker, cardioverter or defibrillator housings, joints, screws, rods, ophthalmic implants, femoral pins, bone plates, grafts, anastomotic devices, perivascular wraps, sutures, staples, shunts for hydrocephalus, dialysis grafts, colostomy bag attachment devices, ear drainage tubes, leads for pace makers and implantable cardioverters and defibrillators, vertebral disks, bone pins, suture anchors, hemostatic barriers, clamps, screws, plates, clips, vascular implants, tissue adhesives and sealants, tissue scaffolds, various types of dressings (e.g., wound dressings), bone substitutes, intraluminal devices, vascular supports, etc.

The implants may be formed from any suitable material, including but not limited to polymers (including stable or inert polymers, organic polymers, organic-inorganic copolymers, inorganic polymers, and biodegradable polymers), metals, metal alloys, inorganic materials such as silicon, and composites thereof, including layered structures with a core of one material and one or more coatings of a different material. Substrates made of a conducting material facilitate electrostatic capture. However, the invention contemplates the use of electrostatic capture, as described below, in conjunction with substrate having low conductivity or which are non-conductive. To enhance electrostatic capture when a non-conductive substrate is employed, the substrate is processed for example while maintaining a strong electrical field in the vicinity of the substrate.

Subjects into which biomedical implants of the invention may be applied or inserted include both human subjects (including male and female subjects and infant, juvenile, adolescent, adult and geriatric subjects) as well as animal subjects (including but not limited to pig, rabbit, mouse, dog, cat, horse, monkey, etc.) for veterinary purposes and/or medical research.

In a preferred embodiment the biomedical implant is an expandable intraluminal vascular graft or stent (e.g., comprising a wire mesh tube) that can be expanded within a blood vessel by an angioplasty balloon associated with a catheter to dilate and expand the lumen of a blood vessel, such as described in U.S. Pat. No. 4,733,665 to Palmaz.

"Pharmaceutical agent" as used herein refers to any of a variety of drugs or pharmaceutical compounds that can be used as active agents to prevent or treat a disease (meaning any treatment of a disease in a mammal, including preventing the disease, i.e. causing the clinical symptoms of the disease not to develop; inhibiting the disease, i.e. arresting the development of clinical symptoms; and/or relieving the disease, i.e. causing the regression of clinical symptoms). It is possible that the pharmaceutical agents of the invention may also comprise two or more drugs or pharmaceutical compounds. Pharmaceutical agents, include but are not limited to antirestenotic agents, antidiabetics, analgesics, antiinflammatory agents, antirheumatics, antihypotensive agents, antihypertensive agents, psychoactive drugs, tranquillizers, antiemetics, muscle relaxants, glucocorticoids, agents for treating ulcerative colitis or Crohn's disease, antiallergics, antibiotics, antiepileptics, anticoagulants, antimycotics, antitussives, arteriosclerosis remedies, diuretics, proteins, peptides, enzymes, enzyme inhibitors, gout remedies, hormones and inhibitors thereof, cardiac glycosides, immunotherapeutic agents and cytokines, laxatives, lipid-lowering agents, migraine remedies, mineral products, otologicals, anti parkinson agents, thyroid therapeutic agents, spasmolytics, platelet aggregation inhibitors, vitamins, cytostatics and metastasis inhibitors, phytopharmaceuticals, chemotherapeutic agents and amino acids. Examples of suitable active ingredients are acarbose, antigens, beta-receptor blockers, non-steroidal antiinflammatory drugs (NSAIDs), cardiac glycosides, acetylsalicylic acid, virustatics, aclarubicin, acyclovir, cisplatin, actinomycin, alpha- and beta-sympatomimetics, dmeprazole, allopurinol, alprostadil, prostaglandins, amantadine, ambroxol, amlodipine, methotrexate, S-aminosalicylic acid, amitriptyline, amoxicillin, anastrozole, atenolol, azathioprine, balsalazide, beclomethasone, betahistine, bezafibrate, bicalutamide, diazepam and diazepam derivatives, budesonide, bufexamac, buprenorphine, methadone, calcium salts, potassium salts, magnesium salts, candesartan, carbamazepine, captopril, cefalosporins, cetirizine, chenodeoxycholic acid, ursodeoxycholic acid, theophylline and theophylline derivatives, trypsins, cimetidine, clarithromycin, clavulanic acid, clindamycin, clobutinol, clonidine, cotrimoxazole, codeine, caffeine, vitamin D and derivatives of vitamin D, colestyramine, cromoglicic acid, coumarin and coumarin derivatives, cysteine, cytarabine, cyclophosphamide, ciclosporin, cyproterone, cytabarine, dapiprazole, desogestrel, desonide, dihydralazine, diltiazem, ergot alkaloids, dimenhydrinate, dimethyl sulphoxide, dimeticone, domperidone and domperidan derivatives, dopamine, doxazosin, doxorubizin, doxylamine, dapiprazole, benzodiazepines, diclofenac, glycoside antibiotics, desipramine, econazole, ACE inhibitors, enalapril, ephedrine, epinephrine, epoetin and epoetin derivatives, morphinans, calcium antagonists, irinotecan, modafinil, orlistat, peptide antibiotics, phenyloin, riluzoles, risedronate, sildenafil, topiramate, macrolide antibiotics, oestrogen and oestrogen derivatives, progestogen and progestogen derivatives, testosterone and testosterone derivatives, androgen and androgen derivatives, ethenzamide, etofenamate, etofibrate, fenofibrate, etofylline, etoposide, famciclovir, famotidine, felodipine, fenofibrate, fentanyl, fenticonazole, gyrase inhibitors, fluconazole, fludarabine, fluarizine, fluorouracil, fluoxetine, flurbiprofen, ibuprofen, flutamide, fluvastatin, follitropin, formoterol, fosfomicin, furosemide, fusidic acid, gallopamil, ganciclovir, gemfibrozil, gentamicin, ginkgo, Saint John's wort, glibenclamide, urea derivatives as oral antidiabetics, glucagon, glucosamine and glucosamine derivatives, glutathione, glycerol and glycerol derivatives, hypothalamus hormones, goserelin, gyrase inhibitors, guanethidine, halofantrine, haloperidol, heparin and heparin derivatives, hyaluronic acid, hydralazine, hydrochlorothiazide and hydrochlorothiazide derivatives, salicylates, hydroxyzine, idarubicin, ifosfamide, imipramine, indometacin, indoramine, insulin, interferons, iodine and iodine derivatives, isoconazole, isoprenaline, glucitol and glucitol derivatives, itraconazole, ketoconazole, ketoprofen, ketotifen, lacidipine, lansoprazole, levodopa, levomethadone, thyroid hormones, lipoic acid and lipoic acid derivatives, lisinopril, lisuride, lofepramine, lomustine, loperamide, loratadine, maprotiline, mebendazole, mebeverine, meclozine, mefenamic acid, mefloquine, meloxicam, mepindolol, meprobamate, meropenem, mesalazine, mesuximide, metamizole, metformin, methotrexate, methylphenidate, methylprednisolone, metixene, metoclopramide, metoprolol, metronidazole, mianserin, miconazole, minocycline, minoxidil, misoprostol, mitomycin, mizolastine, moexipril, morphine and morphine derivatives, evening primrose, nalbuphine, naloxone, tilidine, naproxen, narcotine, natamycin, neostigmine, nicergoline, nicethamide, nifedipine, niflumic acid, nimodipine, nimorazole, nimustine, nisoldipine, adrenaline and adrenaline derivatives, norfloxacin, novamine sulfone, noscapine, nystatin, ofloxacin, olanzapine, olsalazine, omeprazole, omoconazole, ondansetron, oxaceprol, oxacillin, oxiconazole, oxymetazoline, pantoprazole, paracetamol, paroxetine, penciclovir, oral penicillins, pentazocine, pentifylline, pentoxifylline, perphenazine, pethidine, plant extracts, phenazone, pheniramine, barbituric acid derivatives, phenylbutazone, phenyloin, pimozide, pindolol, piperazine, piracetam, pirenzepine, piribedil, piroxicam, pramipexole, pravastatin, prazosin, procaine, promazine, propiverine, propranolol, propyphenazone, prostaglandins, protionamide, proxyphylline, quetiapine, quinapril, quinaprilat, ramipril, ranitidine, reproterol, reserpine, ribavirin, rifampicin, risperidone, ritonavir, ropinirole, roxatidine, roxithromycin, ruscogenin, rutoside and rutoside derivatives, sabadilla, salbutamol, salmeterol, scopolamine, selegiline, sertaconazole, sertindole, sertralion, silicates, sildenafil, simvastatin, sitosterol, sotalol, spaglumic acid, sparfloxacin, spectinomycin, spiramycin, spirapril, spironolactone, stavudine, streptomycin, sucralfate, sufentanil, sulbactam, sulphonamides, sulfasalazine, sulpiride, sultamicillin, sultiam, sumatriptan, suxamethonium chloride, tacrine, tacrolimus, taliolol, tamoxifen, taurolidine, tazarotene, temazepam, teniposide, tenoxicam, terazosin, terbinafine, terbutaline, terfenadine, terlipressin, tertatolol, tetracyclins, teryzoline, theobromine, theophylline, butizine, thiamazole, phenothiazines, thiotepa, tiagabine, tiapride, propionic acid derivatives, ticlopidine, timolol, tinidazole, tioconazole, tioguanine, tioxolone, tiropramide, tizanidine, tolazoline, tolbutamide, tolcapone, tolnaftate, tolperisone, topotecan, torasemide, antioestrogens, tramadol, tramazoline, trandolapril, tranylcypromine, trapidil, trazodone, triamcinolone and triamcinolone derivatives, triamterene, trifluperidol, trifluridine, trimethoprim, trimipramine, tripelennamine, triprolidine, trifosfamide, tromantadine, trometamol, tropalpin, troxerutine, tulobuterol, tyramine, tyrothricin, urapidil, ursodeoxycholic acid, chenodeoxycholic acid, valaciclovir, valproic acid, vancomycin, vecuronium chloride, Viagra, venlafaxine, verapamil, vidarabine, vigabatrin, viloazine, vinblastine, vincamine, vincristine, vindesine, vinorelbine, vinpocetine, viquidil, warfarin, xantinol nicotinate, xipamide, zafirlukast, zalcitabine, zidovudine, zolmitriptan, zolpidem, zoplicone, zotipine and the like. See, e.g., U.S. Pat. No. 6,897,205; see also U.S. Pat. Nos. 6,838,528; 6,497,729.

In some embodiments of the methods and/or devices provided herein, the pharmaceutical agent comprises a macrolide immunosuppressive drug. In some embodiments, the active agent is selected from rapamycin, a prodrug, a derivative, an analog, a hydrate, an ester, and a salt thereof. In some embodiments, the active agent is selected from sirolimus, a prodrug, a derivative, an analog, a hydrate, an ester, and a salt thereof. As used herein, rapamycin and sirolimus are interchangable terms. In some embodiments, the active agent is selected from one or more of sirolimus, everolimus, zotarolimus and biolimus. In some embodiments, the active agent comprises a macrolide immunosuppressive (limus) drug.

In some embodiments, the pharmaceutical agent comprises one or more of rapamycin, biolimus (biolimus A9), 40-O-(2-Hydroxyethyl)rapamycin (everolimus), 40-O-Benzyl-rapamycin, 40-O-(4'-Hydroxymethyl)benzyl-rapamycin, 40-O-[4'-(1,2-Dihydroxyethyl)]benzyl-rapamycin, 40-O-Allyl-rapamycin, 40-O-[3'-(2,2-Dimethyl-1,3-dioxolan-4(S)-yl)-prop-2'-en-1'-yl]-rapamycin, (2':E,4'S)-40-O-(4',5'-Dihydroxypent-2'-en-1'-yl)-rapamycin 40-O-(2-Hydroxy)ethoxycar-bonylmethyl-rapamycin, 40-O-(3-Hydroxy)propyl-rapamycin 4O—O-(6-Hydroxy)hexyl-rapamycin 40-O-[2-(2-Hydroxy)ethoxy]ethyl-rapamycin 4O—O-[(3S)-2,2-Dimethyldioxolan-3-yl]methyl-rapamycin, 40-O-[(2S)-2,3-Dihydroxyprop-1-yl]-rapamycin, 4O—O-(2-Acetoxy)ethyl-rapamycin 4O—O-(2-Nicotinoyloxy)ethyl-rapamycin, 4O—O-[2-(N-Morpholino)acetoxy]ethyl-rapamycin 4O—O-(2-N-Imidazolylacetoxy)ethyl-rapamycin, 40-O-[2-(N-Methyl-N'-piperazinyl)acetoxy]ethyl-rapamycin, 39-O-Desmethyl-39,40-O,O-ethylene-rapamycin, (26R)-26-Dihydro-40-O-(2-hydroxy)ethyl-rapamycin, 28-O-Methyl-rapamycin, 4O—O-(2-Aminoethyl)-rapamycin, 4O—O-(2-Acetaminoethyl)-rapamycin 4O—O-(2-Nicotinamidoethyl)-rapamycin, 4O—O-(2-(N-Methyl-imidazo-2'-ylcarbethoxamido)ethyl)-rapamycin, 4O—O-(2-Ethoxycarbonylaminoethyl)-rapamycin, 40-O-(2-Tolylsulfonamidoethyl)-rapamycin, 40-O-[2-(4',5'-Dicarboethoxy-1',2',3'-triazol-1'-yl)-ethyl]-rapamycin, 42-Epi-(tetrazolyl)rapamycin (tacrolimus), 42-[3-hydroxy-2-(hydroxymethyl)-2-methylpropanoate]rapamycin (temsirolimus), (42S)-42-Deoxy-42-(1H-tetrazol-1-yl)-rapamycin (zotarolimus), picrolimus, novolimus, myolimus, and salts, derivatives, isomers, racemates, diastereoisomers, prodrugs, hydrate, ester, or analogs thereof.

The pharmaceutical agents may, if desired, also be used in the form of their pharmaceutically acceptable salts or derivatives (meaning salts which retain the biological effectiveness and properties of the compounds of this invention and which are not biologically or otherwise undesirable), and in the case of chiral active ingredients it is possible to employ both optically active isomers and racemates or mixtures of diastereoisomers. As well, the pharmaceutical agent may include a prodrug, a hydrate, an ester, a derivative or analogs of a compound or molecule.

A "pharmaceutically acceptable salt" may be prepared for any pharmaceutical agent having a functionality capable of forming a salt, for example an acid or base functionality. Pharmaceutically acceptable salts may be derived from organic or inorganic acids and bases. The term "pharmaceutically-acceptable salts" in these instances refers to the relatively non-toxic, inorganic and organic base addition salts of the pharmaceutical agents.

"Prodrugs" are derivative compounds derivatized by the addition of a group that endows greater solubility to the compound desired to be delivered. Once in the body, the prodrug is typically acted upon by an enzyme, e.g., an esterase, amidase, or phosphatase, to generate the active compound.

"Stability" as used herein in refers to the stability of the drug in a polymer coating deposited on a substrate in its final product form (e.g., stability of the drug in a coated stent). The term stability may define 5% or less degradation of the drug in the final product form. In some embodiments, the term stability will define 10% or less degradation of the drug in the final product form. In some embodiments, the term stability will define 15% or less degradation of the drug in the final product form. In some embodiments, the term stability will define 20% or less degradation of the drug in the final product form.

Some embodiments comprise active biological agents. In some embodiments, the coating comprises an active biological agent. "Active biological agent" as used herein refers to a substance, originally produced by living organisms, that can be used to prevent or treat a disease (meaning any treatment of a disease in a mammal, including preventing the disease, i.e. causing the clinical symptoms of the disease not to develop; inhibiting the disease, i.e. arresting the development of clinical symptoms; and/or relieving the disease, i.e. causing the regression of clinical symptoms). It is possible that the active biological agents of the invention may also comprise two or more active biological agents or an active biological agent combined with a pharmaceutical agent, a stabilizing agent or chemical or biological entity. Although the active biological agent may have been originally produced by living organisms, those of the present invention may also have been synthetically prepared, or by methods combining biological isolation and synthetic modification. By way of a non-limiting example, a nucleic acid could be isolated form from a biological source, or prepared by traditional techniques, known to those skilled in the art of nucleic acid synthesis. Furthermore, the nucleic acid may be further modified to contain non-naturally occurring moieties. Non-limiting examples of active biological agents include peptides, proteins, enzymes, glycoproteins, nucleic acids (including deoxyribonucleotide or ribonucleotide polymers in either single or double stranded form, and unless otherwise limited, encompasses known analogues of natural nucleotides that hybridize to nucleic acids in a manner similar to naturally occurring nucleotides), antisense nucleic acids, fatty acids, antimicrobials, vitamins, hormones, steroids, lipids, polysaccharides, carbohydrates and the like. They further include, but are not limited to, antirestenotic agents, antidiabetics, analgesics, antiinflammatory agents, antirheumatics, antihypotensive agents, antihypertensive agents, psychoactive drugs, tranquillizers, antiemetics, muscle relaxants, glucocorticoids, agents for treating ulcerative colitis or Crohn's disease, antiallergics, antibiotics, antiepileptics, anticoagulants, antimycotics, antitussives, arteriosclerosis remedies, diuretics, proteins, peptides, enzymes, enzyme inhibitors, gout remedies, hormones and inhibitors thereof, cardiac glycosides, immunotherapeutic agents and cytokines, laxatives, lipid-lowering agents, migraine remedies, mineral products, otologicals, anti parkinson agents, thyroid therapeutic agents, spasmolytics, platelet aggregation inhibitors, vitamins, cytostatics and metastasis inhibitors, phytopharmaceuticals and chemotherapeutic agents. Preferably, the active biological agent is a peptide, protein or enzyme, including derivatives and analogs of natural peptides, proteins and enzymes. The active biological agent may also be a hormone, gene therapies, RNA, siRNA, and/or cellular therapies (for non-limiting example, stem cells or T-cells).

In some embodiments, the coating of the device comprises a combination of a pharmaceutical agent and an active biological agent.

In some embodiments, the device comprises an active agent. In some embodiments, the coating of the device comprises an active agent. "Active agent" as used herein refers to any pharmaceutical agent or active biological agent as described herein.

"Activity" as used herein refers to the ability of a pharmaceutical or active biological agent to prevent or treat a disease (meaning any treatment of a disease in a mammal, including preventing the disease, i.e. causing the clinical symptoms of the disease not to develop; inhibiting the disease, i.e. arresting the development of clinical symptoms; and/or relieving the disease, i.e. causing the regression of clinical symptoms). Thus the activity of a pharmaceutical or active biological agent should be of therapeutic or prophylactic value.

"Secondary, tertiary and quaternary structure" as used herein are defined as follows. The active biological agents of the present invention will typically possess some degree of secondary, tertiary, or quaternary structure, or a combination thereof, upon which the activity of the agent depends. As an illustrative, non-limiting example, proteins possess secondary, tertiary and quaternary structure. Secondary structure refers to the spatial arrangement of amino acid residues that are near one another in the linear sequence. The α-helix and the β-strand are elements of secondary structure. Tertiary structure refers to the spatial arrangement of amino acid residues that are far apart in the linear sequence and to the pattern of disulfide bonds. Proteins containing more than one polypeptide chain exhibit an additional level of structural organization. Each polypeptide chain in such a protein is called a subunit. Quaternary structure refers to the spatial arrangement of subunits and the nature of their contacts. For example hemoglobin consists of two α and two β chains. It is well known that protein function arises from its conformation or three dimensional arrangement of atoms (a stretched out polypeptide chain is devoid of activity). Thus one aspect of the present invention is to manipulate active biological agents, while being careful to maintain their conformation, so as not to lose their therapeutic activity.

"Polymer" as used herein, refers to a series of repeating monomeric units that have been cross-linked or polymerized. Any suitable polymer can be used to carry out the present invention. It is possible that the polymers of the invention may also comprise two, three, four or more different polymers. In some embodiments, of the invention only one polymer is used. In some preferred embodiments a combination of two polymers are used. Combinations of polymers can be in varying ratios, to provide coatings with differing properties. Those of skill in the art of polymer chemistry will be familiar with the different properties of polymeric compounds. Polymers are referred to herein with respect to coating polymers and with regard to balloon polymers. These may be different polymers having different attributes. For example, the coating polymer is meant to be implanted in the subject when the device is implanted, however, the balloon polymer is part of the delivery system and is used to expand the device to the desired dimensions. Thus, the two polymers serve very different purposes and are typically made of different polymers, as described herein.

Typical balloon polymers are well known and may comprise any number of types of polymers that are compliant, semi-compliant, or non-compliant in use, for example. Polymers of the balloon may comprise, for non-limiting example, polyamide. Polymers of the balloon may comprise, for non-limiting example, at least one of: polyethylene, polyethylene terephthalate (PET), high density polyethylene (HDPE), Arnitel, Hyrtrel, polyetherether ketone (PEEK), urethane, polyurethane, urethane elastomer, nylon, polyamide, polyether block amide (PEBAX), a block copolymer of any polymer listed herein, Teflon, polyolefin, and a thermoplastic elastomer.

The balloon may be formed of any material which may be made by radial expansion, typically thermoplastic polymers. It is possible to make balloons from a variety of thermoplastic polymers. Some balloons may comprise low, linear low, medium and high density polyethylenes; polypropylenes; poly(ethylene vinyl acetate) (EVA); poly(ethylene vinyl alcohol) (EVOH) and EVA/EVOH terpolymers; polyolefin-ionomers; ethylene-butylene-styrene block copolymers blended with low molecular weight polystyrene and, optionally, polypropylene, and similar compositions substituting butadiene or isoprene in place of the ethylene and butylene; poly(vinyl chloride); polyurethanes; polyesters and copolyesters; polycarbonate; thermoplastic elastomers; silicone-polycarbonate copolymers; polyamides; thermoplastic polyimides; liquid crystal polymers; ABS (acrylonitrile butadiene styrene); ANS (acrylonitrile styrene); Delrin polyacetal; PEI (polyetherimide); and PES (polyether sulfone). Physical blends and copolymers of such materials may also be used.

Orientable polyesters, especially polyethylene terephthalate (PET), in some embodiments form the balloon of the delivery system. Suitable PET polymers have an initial intrinsic viscosity of at least 0.5, for instance, 0.6-1.3. Other high strength polyester materials, such as poly(ethylene napthalenedicarboxylate) (PEN); and poly(butylene terephthalate may also be used. Polyester copolymers such as the random copolymer made from dimethyl terephthalate dimethyl isophthalate and ethylene glycol described in U.S. Pat. No. 5,330,428 Wang, et al. (incorporated in its entirety by reference herein) may also be employed.

Examples of polyamides which may be used in some embodiments include nylon 6, nylon 64, nylon 66, nylon 610, nylon 610, nylon 612, nylon 46, nylon 9, nylon 10, nylon 11, nylon 12, and mixtures thereof.

The balloon may be formed of polyurethanes such as Tecothane from Thermedics. Tecothane. is a thermoplastic, aromatic, polyether polyurethane synthesized from methylene diisocyanate (MDI), polytetramethylene ether glycol (PTMEG) and 1,4 butanediol chain extender. Tecothane. 1065D and 1075D are examples. Other polyurethanes which have been used are Isoplast. 301, a high strength engineering thermoplastic polyurethane, and Pellethane. 2363-75D, both sold by Dow Chemical Co. References illustrating polyurethane balloon materials include U.S. Pat. No. 4,950,239, to Gahara, U.S. Pat. No. 5,500,180 to Anderson et al., U.S. Pat. No. 6,146,356 to Wang, et al., and U.S. Pat. No. 6,572,813, to Zhang, et al., which are incorporated herein by reference in their entirety.

Other suitable polymeric materials include Engage from DuPont Dow Elastomers (an ethylene alpha-olefin polymer) and Exact, available from Exxon Chemical, both of which are thermoplastic polymers and are believed to be polyolefin elastomers produced from metallocene catalysts. These are compliant materials which provide balloons which have a substantial range of available diameters to which they may be expanded and still recover elastically.

Balloons of the invention may be also made of polyamide/polyether block copolymers. The polyamide/polyether block copolymers are commonly identified by the acronym PEBA (polyether block amide). The polyamide and polyether segments of these block copolymers may be linked through amide linkages or ester linked segmented polymers, i.e. polyamide/polyether polyesters. Such polyamide/polyether/polyester block copolymers are made by a molten state polycondensation reaction of a dicarboxylic polyamide and a polyether diol. The result is a short chain polyester made up of blocks of polyamide and polyether.

Polyamide/polyether polyesters are sold commercially under the Pebax, trademark by Elf Atochem North America, Inc., Philadelphia Pa. Examples of suitable commercially available polymers are the Pebax 33 series polymers with hardness 60 and above, Shore D scale, especially Pebax 6333, 7033 and 7233. These polymers are made up of nylon 12 segments and poly(tetramethylene ether) segments.

It is also possible to utilize polyester/polyether segmented block copolymers and obtain similar balloon properties. Such polymers are made up of at least two polyester and at least two polyether segments. The polyether segments are the same as previously described for the polyamide/polyether block copolymers useful in the invention. The polyester segments are polyesters of an aromatic dicarboxylic acid and a two to four carbon diol. The polyether segments of the polyester/polyether segmented block copolymers are aliphatic polyethers having at least 2 and no more than 10 linear saturated aliphatic carbon atoms between ether linkages. More preferably the ether segments have 4-6 carbons between ether linkages, and most preferably they are poly(tetramethylene ether) segments. Examples of other polyethers which may be employed in place of the preferred tetramethylene ether segments include polyethylene glycol, polypropylene glycol, poly(pentamethylene ether) and poly (hexamethylene ether). The hydrocarbon portions of the polyether may be optionally branched. An example is the polyether of 2-ethylhexane diol. Generally such branches will contain no more than two carbon atoms. The molecular weight of the polyether segments is suitably between about 400 and 2,500, preferably between 650 and 1000.

The polyester segments are polyesters of an aromatic dicarboxylic acid and a two to four carbon diol. Suitable dicarboxylic acids used to prepare the polyester segments of the polyester/polyether block copolymers are ortho-, meta- or para-phthalic acid, napthalenedicarboxylic acid or meta-terphenyl-4,4'-dicarboxylic acids. Preferred polyester/polyether block copolymers are poly(butylene terephthalate)-block-poly(tetramethylene oxide) polymers such as Arnitel EM 740, sold by DSM Engineering Plastics, and Hytrel polymers, sold by DuPont, such as Hytrel 8230.

Examples of thermoplastic polyimides are described in T. L. St. Clair and H. D. Burks, "Thermoplastic/Melt-Processable Polyimides," NASA Conf. Pub. #2334 (1984), pp. 337-355, incorporated herein by reference in its entirety. A suitable thermoplastic polyimide is described in U.S. Pat. No. 5,096,848 (incorporated herein by reference in its entirety) and is available commercially under the tradename Aurum from Mitsui Toatsu Chemicals, Inc., of Tokyo, Japan.

Examples of liquid crystal polymers include the products Vectra from Hoechst Celanese; Rodrun from Unitika; LX and HX series polymers and Zenite polymers from DuPont; Sumikosuper and Ekonol from Sumitomo Chemical; Granlar from Grandmont; and Xydar® from Amoco. Suitably the liquid crystal polymer materials are blended with another thermoplastic polymer such as PET, nylon 12, or a block copolymer such as Pebax7033 or 7233 or Arintel EM 740 or Hytrel 8230. The liquid crystal polymer may be present as fibers in a matrix of the blend polymer.

The balloon material may be multilayered, for instance combining an outer layer of a material which is relatively soft and flexible, and/or lubricious, with an inner layer of a stronger polymer. Alternatively, or additionally, an innermost layer may be provided which is selected for compatibility with direct bonding, e.g. by fusion welding, or adhesive bonding, to the catheter material.

Polymers used for coatings described herein may be durable (non-bioabsorbable), bioabsorbable, or a combination thereof. Durable polymers and/or bioabsorbable polymers known in the art may be used in some embodiments described herein. Polymers may be hydrophilic and/or hydrophobic, depending on the embodiment. Some coating polymers known in the art and may include polylactic acid, polycaprolactone, polyethylene glucol, ethylvinylacetate, polyorganophosphazine, polyurethane, polytetrafluoroethane, phosphorylcholine, methacrylo-phosphorylcholine-lauryl-methacrulate, combinations thereof, and/or copolymers thereof. Representative polymers for coatings in some embodiments include, but are not limited to, poly(ester amide), polystyrene-polyisobutylene-polystyrene block copolymer (SIS), polystyrene, polyisobutylene, polycaprolactone (PCL), poly(L-lactide), poly(D,L-lactide), poly(lactides), polylactic acid (PLA), poly(lactide-co-glycolide), poly(glycolide), polyalkylene, polyfluoroalkylene, polyhydroxyalkanoate, poly(3-hydroxybutyrate), poly(4-hydroxybutyrate), poly(3-hydroxyvalerate), poly(3-hydroxybutyrate-co-3-hydroxyvalerate), poly(3-hydroxyhexanoate), poly(4-hyroxyhexanoate), mid-chain polyhydroxyalkanoate, poly (trimethylene carbonate), poly (ortho ester), polyphosphazenes, poly (phosphoester), poly(tyrosine derived arylates), poly(tyrosine derived carbonates), polydimethyloxanone (PDMS), polyvinylidene fluoride (PVDF), polyhexafluoropropylene (HFP), polydimethylsiloxane, poly (vinylidene fluoride-co-hexafluoropropylene) (PVDF-HFP), poly (vinylidene fluoride-co-chlorotrifluoroethylene) (PVDF-CTFE), poly(methacrylates) such as poly(butyl methacrylate) (PBMA) or poly(methyl methacrylate) (PMMA), poly(vinyl acetate), poly(ethylene-co-vinyl acetate), poly(ethylene-co-vinyl alcohol), poly(ester urethanes), poly(ether-urethanes), poly(carbonate-urethanes), poly(silicone-urethanes), poly(urea-urethanes) or a combination thereof.

In some other embodiments, the coating polymer may be, but is not limited to, polymers and co-polymers of PEG acrylate (PEGA), PEG methacrylate, 2-methacryloyloxyethylphosphorylcholine (MPC) and n-vinyl pyrrolidone (VP), carboxylic acid bearing monomers such as methacrylic acid (MA), acrylic acid (AA), hydroxyl bearing monomers such as HEMA, hydroxypropyl methacrylate (HPMA), hydroxypropylmethacrylamide, and 3-trimethylsilylpropyl methacrylate (TMSPMA), poly(ethylene glycol) (PEG), poly (propylene glycol), SIS-PEG, polystyrene-PEG, polyisobutylene-PEG, PCL-PEG, PLA-PEG, PMMA-PEG, PDMS-PEG, PVDF-PEG, PLURONIC™ surfactants (polypropylene oxide-co-polyethylene glycol), poly(tetramethylene glycol), poly(L-lysine-ethylene glycol) (PLL-g-PEG), poly(L-g-lysine-hyaluronic acid) (PLL-g-HA), poly(L-lysine-g-phosphoryl choline) (PLL-g-PC), poly(L-lysine-g-vinylpyrrolidone) (PLL-g-PVP), poly(ethylimine-g-ethylene glycol) (PEI-g-PEG), poly(ethylimine-g-hyaluronic acid) (PEI-g-HA), poly(ethylimine-g-phosphoryl choline) (PEI-g-PC), and poly(ethylimine-g-vinylpyrrolidone) (PEI-g-PVP), PLL-co-HA, PLL-co-PC, PLL-co-PVP, PEI-co-PEG, PEI-co-HA, PEI-co-PC, and PEI-co-PVP, hydroxy functional poly(vinyl pyrrolidone), polyalkylene oxide, dextran, dextrin, sodium hyaluronate, hyaluronic acid, elastin, chitosan, acrylic sulfate, acrylic sulfonate, acrylic sulfamate, methacrylic sulfate, methacrylic sulfonate, methacrylic sulfamate and combination thereof. The non-fouling polymer can be, for example, poly(ethylene glycol), poly(alkylene oxide), hydroxyethylmethacrylate (HEMA) polymer and copolymers, poly(n-propylmethacrylamide), sulfonated polystyrene, hyaluronic acid, poly(vinyl alcohol), poly(N-vinyl-2-pyrrolidone), sulfonated dextran, phosphoryl choline, choline, or combinations thereof.

In some other embodiments, the coating polymer comprises at least one of: PLGA, a copolymer comprising PLGA (i.e. a PLGA copolymer), a PLGA copolymer with a ratio of about 40:60 to about 60:40, a PLGA copolymer with a ratio of about 70:30 to about 90:10, a PLGA copolymer having a molecular weight of about 10 kD, a PLGA copolymer having a molecular weight of about 19 kD, PGA poly (glycolide), LPLA poly(l-lactide), DLPLA poly(dl-lactide), PCL poly(e-caprolactone) PDO, poly(dioxolane) PGA-TMC, 85/15 DLPLG p(dl-lactide-co-glycolide), 75/25 DLPL, 65/35 DLPLG, 50/50 DLPLG, TMC poly(trimethylcarbonate), p(CPP:SA) poly(1,3-bis-p-(carboxyphenoxy) propane-co-sebacic acid), and a combination thereof "Copolymer" as used herein refers to a polymer being composed of two or more different monomers. A copolymer may also and/or alternatively refer to random, block, graft, copolymers known to those of skill in the art.

"Biocompatible" as used herein, refers to any material that does not cause injury or death to the animal or induce an adverse reaction in an animal when placed in intimate contact with the animal's tissues. Adverse reactions include for example inflammation, infection, fibrotic tissue formation, cell death, or thrombosis. The terms "biocompatible" and "biocompatibility" when used herein are art-recognized and mean that the referent is neither itself toxic to a host (e.g., an animal or human), nor degrades (if it degrades) at a rate that produces byproducts (e.g., monomeric or oligomeric subunits or other byproducts) at toxic concentrations, causes inflammation or irritation, or induces an immune reaction in the host. It is not necessary that any subject composition have a purity of 100% to be deemed biocompatible. Hence, a subject composition may comprise 99%, 98%, 97%, 96%, 95%, 90% 85%, 80%, 75% or even less of biocompatible agents, e.g., including polymers and other materials and excipients described herein, and still be biocompatible.

To determine whether a polymer or other material is biocompatible, it may be necessary to conduct a toxicity analysis. Such assays are well known in the art. One example of such an assay may be performed with live carcinoma cells, such as GT3TKB tumor cells, in the following manner: the sample is degraded in 1 M NaOH at 37 degrees C. until complete degradation is observed. The solution is then neutralized with 1 M HCl. About 200 microliters of various concentrations of the degraded sample products are placed in 96-well tissue culture plates and seeded with human gastric carcinoma cells (GT3TKB) at 104/well density. The degraded sample products are incubated with the GT3TKB cells for 48 hours. The results of the assay may be plotted as % relative growth vs. concentration of degraded sample in the tissue-culture well. In addition, polymers and formulations of the present invention may also be evaluated by well-known in vivo tests, such as subcutaneous implantations in rats to confirm that they do not cause significant levels of irritation or inflammation at the subcutaneous implantation sites.

The terms "bioabsorbable," "biodegradable," "bioerodible," and "bioresorbable," are art-recognized synonyms. These terms are used herein interchangeably. Bioabsorbable polymers typically differ from non-bioabsorbable polymers in that the former may be absorbed (e.g.; degraded) during use. In certain embodiments, such use involves in vivo use, such as in vivo therapy, and in other certain embodiments, such use involves in vitro use. In general, degradation attributable to biodegradability involves the degradation of a bioabsorbable polymer into its component subunits, or digestion, e.g., by a biochemical process, of the polymer into smaller, non-polymeric subunits. In certain embodiments, biodegradation may occur by enzymatic mediation, degradation in the presence of water (hydrolysis) and/or other chemical species in the body, or both. The bioabsorbabilty of a polymer may be shown in-vitro as described herein or by methods known to one of skill in the art. An in-vitro test for bioabsorbability of a polymer does not require living cells or other biologic materials to show bioabsorption properties (e.g. degradation, digestion). Thus, resorbtion, resorption, absorption, absorbtion, erosion, and dissolution may also be used synonymously with the terms "bioabsorbable," "biodegradable," "bioerodible," and "bioresorbable." Mechanisms of degradation of a bioaborbable polymer may include, but are not limited to, bulk degradation, surface erosion, and combinations thereof.

As used herein, the term "biodegradation" encompasses both general types of biodegradation. The degradation rate of a biodegradable polymer often depends in part on a variety of factors, including the chemical identity of the linkage responsible for any degradation, the molecular weight, crystallinity, biostability, and degree of cross-linking of such polymer, the physical characteristics (e.g., shape and size) of the implant, and the mode and location of administration. For example, the greater the molecular weight, the higher the degree of crystallinity, and/or the greater the biostability, the biodegradation of any bioabsorbable polymer is usually slower.

"Therapeutically desirable morphology" as used herein refers to the gross form and structure of the pharmaceutical agent, once deposited on the substrate, so as to provide for optimal conditions of ex vivo storage, in vivo preservation and/or in vivo release. Such optimal conditions may include, but are not limited to increased shelf life, increased in vivo stability, good biocompatibility, good bioavailability or modified release rates. Typically, for the present invention, the desired morphology of a pharmaceutical agent would be crystalline or semi-crystalline or amorphous, although this may vary widely depending on many factors including, but not limited to, the nature of the pharmaceutical agent, the disease to be treated/prevented, the intended storage conditions for the substrate prior to use or the location within the body of any biomedical implant. Preferably at least 10%, 20%, 30%, 40%, 50%, 60%, 70%, 80%, 90% or 100% of the pharmaceutical agent is in crystalline or semi-crystalline form.

"Stabilizing agent" as used herein refers to any substance that maintains or enhances the stability of the biological agent. Ideally these stabilizing agents are classified as Generally Regarded As Safe (GRAS) materials by the US Food and Drug Administration (FDA). Examples of stabilizing agents include, but are not limited to carrier proteins, such as albumin, gelatin, metals or inorganic salts. Pharmaceutically acceptable excipient that may be present can further be found in the relevant literature, for example in the Handbook of Pharmaceutical Additives: An International Guide to More Than 6000 Products by Trade Name, Chemical, Function, and Manufacturer; Michael and Irene Ash (Eds.); Gower Publishing Ltd.; Aldershot, Hampshire, England, 1995.

"Compressed fluid" as used herein refers to a fluid of appreciable density (e.g., >0.2 g/cc) that is a gas at standard temperature and pressure. "Supercritical fluid", "near-critical fluid", "near-supercritical fluid", "critical fluid", "densified fluid" or "densified gas" as used herein refers to a compressed fluid under conditions wherein the temperature is at least 80% of the critical temperature of the fluid and the pressure is at least 50% of the critical pressure of the fluid, and/or a density of +50% of the critical density of the fluid.

Examples of substances that demonstrate supercritical or near critical behavior suitable for the present invention include, but are not limited to carbon dioxide, isobutylene, ammonia, water, methanol, ethanol, ethane, propane, butane, pentane, dimethyl ether, xenon, sulfur hexafluoride, halogenated and partially halogenated materials such as chlorofluorocarbons, hydrochlorofluorocarbons, hydrofluorocarbons, perfluorocarbon (such as perfluoromethane and perfluoropropane, chloroform, trichloro-fluoromethane, dichloro-difluoromethane, dichloro-tetrafluoroethane) and mixtures thereof. Preferably, the supercritical fluid is hexafluoropropane (FC-236EA), or 1,1,1,2,3,3-hexafluoropropane. Preferably, the supercritical fluid is hexafluoropropane (FC-236EA), or 1,1,1,2,3,3-hexafluoropropane for use in PLGA polymer coatings.

Supercritical fluids are used in some embodiments to manufacture polymer coatings of the device according to an RESS (and/or eRESS) process.

"Sintering" as used herein refers to the process by which parts of the polymer or the entire polymer becomes continuous (e.g., formation of a continuous polymer film). As discussed below, the sintering process is controlled to produce a fully conformal continuous polymer (complete sintering) or to produce regions or domains of continuous coating while producing voids (discontinuities) in the polymer. As well, the sintering process is controlled such that some phase separation is obtained or maintained between polymer different polymers (e.g., polymers A and B) and/or to produce phase separation between discrete polymer particles. Through the sintering process, the adhesions properties of the coating are improved to reduce flaking of detachment of the coating from the substrate during manipulation in use. As described below, in some embodiments, the sintering process is controlled to provide incomplete sintering of the polymer. In embodiments involving incomplete sintering, a polymer is formed with continuous domains, and voids, gaps, cavities, pores, channels or, interstices that provide space for sequestering a therapeutic agent which is released under controlled conditions. Depending on the nature of the polymer, the size of polymer particles and/or other polymer properties, a compressed gas, a densified gas, a near critical fluid or a super-critical fluid may be employed. In one example, carbon dioxide is used to treat a substrate that has been coated with a polymer and a drug, using dry powder and RESS electrostatic coating processes. In another example, isobutylene is employed in the sintering process. In other examples a mixture of carbon dioxide and isobutylene is employed. In another example, 1,1,2,3,3-hexafluoropropane is employed in the sintering process.

When an amorphous material is heated to a temperature above its glass transition temperature, or when a crystalline material is heated to a temperature above a phase transition temperature, the molecules comprising the material are more mobile, which in turn means that they are more active and thus more prone to reactions such as oxidation. However, when an amorphous material is maintained at a temperature below its glass transition temperature, its molecules are substantially immobilized and thus less prone to reactions. Likewise, when a crystalline material is maintained at a temperature below its phase transition temperature, its molecules are substantially immobilized and thus less prone to reactions. Accordingly, processing drug components at mild conditions, such as the deposition and sintering conditions described herein, minimizes cross-reactions and degradation of the drug component. One type of reaction that is minimized by the processes of the invention relates to the ability to avoid conventional solvents which in turn minimizes-oxidation of drug, whether in amorphous, semi-crystalline, or crystalline form, by reducing exposure thereof to free radicals, residual solvents, protic materials, polar-protic materials, oxidation initiators, and autoxidation initiators.

Sintering may be used in some embodiments in order to manufacture the coated stent.

"Rapid Expansion of Supercritical Solutions" or "RESS" as used herein involves the dissolution of a polymer into a compressed fluid, typically a supercritical fluid, followed by rapid expansion into a chamber at lower pressure, typically near atmospheric conditions. The rapid expansion of the supercritical fluid solution through a small opening, with its accompanying decrease in density, reduces the dissolution capacity of the fluid and results in the nucleation and growth of polymer particles. The atmosphere of the chamber is maintained in an electrically neutral state by maintaining an isolating "cloud" of gas in the chamber. Carbon dioxide, nitrogen, argon, helium, or other appropriate gas is employed to prevent electrical charge is transferred from the substrate to the surrounding environment.

Device coatings described herein may be manufactured using an RESS process.

"Bulk properties" properties of a coating including a pharmaceutical or a biological agent that can be enhanced through the methods of the invention include for example: adhesion, smoothness, conformality, thickness, and compositional mixing.

"Electrostatically charged" or "electrical potential" or "electrostatic capture" as used herein refers to the collection of the spray-produced particles upon a substrate that has a different electrostatic potential than the sprayed particles. Thus, the substrate is at an attractive electronic potential with respect to the particles exiting, which results in the capture of the particles upon the substrate. i.e. the substrate and particles are oppositely charged, and the particles transport through the gaseous medium of the capture vessel onto the surface of the substrate is enhanced via electrostatic attraction. This may be achieved by charging the particles and grounding the substrate or conversely charging the substrate and grounding the particles, by charging the particles at one potential (e.g. negative charge) and charging the substrate at an opposed potential (e.g. positive charge), or by some other process, which would be easily envisaged by one of skill in the art of electrostatic capture. A process that includes electrostatically charged particles, or creates an electrical potential between the particles and the substrate, or includes electrostatic capture of the particles on the substrate may be denoted as an "e-" or an "e" process. For non-limiting example, an RESS particle deposition process that further comprises electrostatic capture of the particles on the substrate may be referred to as an "e-RESS" or "eRESS" process herein.

"Intimate mixture" as used herein, refers to two or more materials, compounds, or substances that are uniformly distributed or dispersed together.

"Layer" as used herein refers to a material covering a surface or forming an overlying part or segment. Two different layers may have overlapping portions whereby material from one layer may be in contact with material from another layer. Contact between materials of different layers can be measured by determining a distance between the materials. For example, Raman spectroscopy may be employed in identifying materials from two layers present in close proximity to each other.

While layers defined by uniform thickness and/or regular shape are contemplated herein, several embodiments described below relate to layers having varying thickness and/or irregular shape. Material of one layer may extend into the space largely occupied by material of another layer. For example, in a coating having three layers formed in sequence as a first polymer layer, a pharmaceutical agent layer and a second polymer layer, material from the second polymer layer which is deposited last in this sequence may extend into the space largely occupied by material of the pharmaceutical agent layer whereby material from the second polymer layer may have contact with material from the pharmaceutical layer. It is also contemplated that material from the second polymer layer may extend through the entire layer largely occupied by pharmaceutical agent and contact material from the first polymer layer.

It should be noted however that contact between material from the second polymer layer (or the first polymer layer) and material from the pharmaceutical agent layer (e.g.; a pharmaceutical agent crystal particle or a portion thereof) does not necessarily imply formation of a mixture between the material from the first or second polymer layers and material from the pharmaceutical agent layer. In some embodiments, a layer may be defined by the physical three-dimensional space occupied by crystalline particles of a pharmaceutical agent (and/or biological agent). It is contemplated that such layer may or may not be continuous as physical space occupied by the crystal particles of pharmaceutical agents may be interrupted, for example, by polymer material from an adjacent polymer layer. An adjacent polymer layer may be a layer that is in physical proximity to be pharmaceutical agent particles in the pharmaceutical agent layer. Similarly, an adjacent layer may be the layer formed in a process step right before or right after the process step in which pharmaceutical agent particles are deposited to form the pharmaceutical agent layer.

As described herein, material deposition and layer formation provided herein are advantageous in that the pharmaceutical agent remains largely in crystalline form during the entire process. While the polymer particles and the pharmaceutical agent particles may be in contact, the layer formation process is controlled to avoid formation of a mixture between the pharmaceutical agent particles the polymer particles during formation of a coated device.

"Laminate coating" as used herein refers to a coating made up of two or more layers of material. Means for creating a laminate coating as described herein (e.g.; a laminate coating comprising bioabsorbable polymer(s) and pharmaceutical agent) may include coating the stent with drug and polymer as described herein (RESS, e-RESS, e-DPC, compressed-gas sintering). The process comprises performing multiple and sequential coating steps (with sintering steps for polymer materials) wherein different materials may be deposited in each step, thus creating a laminated structure with a multitude of layers (at least 2 layers) including polymer layers and pharmaceutical agent layers to build the final device (e.g.; laminate coated stent).

Trackability

Provided herein is a stent delivery system comprising: an elongate member having an inflation lumen and a guidewire lumen therein; a balloon having an interior that is in fluid communication with the inflation lumen; and a stent comprising a coating mounted on the balloon, in which for a stent of about 2.25 mm in diameter to about 4.0 mm in diameter by about 9 mm to about 30 mm in length in an expanded state, a stent system trackability expressed as peak force over the track length is at most 1.5 Newtons.

Provided herein is a stent delivery system comprising: an elongate member having an inflation lumen and a guidewire lumen therein; a balloon having an interior that is in fluid communication with the inflation lumen; and a stent comprising a coating mounted on the balloon, in which for a stent of about 2.25 mm in diameter to about 4.0 mm in diameter by about 9 mm to about 30 mm in length in an expanded state, a stent system trackability expressed as mean force over the track length is at most 0.5 Newtons.

"Trackability" as used herein is defined as the ability of the delivery system to advance over a guidewire along the path of a vessel in a simulated anatomy. The trackability of a stent system can describe the stent system's performance tracking through the curved vessel system up to (and in some instances, including) the lesion to be treated in the artery. Thus, the trackability is a combined property, which is mainly determined by the stiffness and profile of the stent, and friction effects between the stent system and the guiding catheter and the guide wire. Trackability can be expressed as a mean track force over the track length, and/or as a peak force measured over the track length. Quantitative assessment can be provided by, for example, the method provided in Schmidt W, Grabow N, Behrens P, Schmitz K-P: "Trackability, Crossability, and Pushability of Coronary Stent Systems—An Experimental Approach" Biomed. Technik 47 (2002), Erg. 1, S. 124-126, which is a method used in Tortuosity Test 1 (which is also described in "New Aspects of in vitro Testing of Arterial Stents based on the new European Standard EN 14299" by Wolfram Schmidt, Peter Behrens, Klaus-Peter Schmitz, Institute for Biomedical Engineering, University of Rostock, Germany at http://www.iib-ev.de/pl/pdf/EN14299.pdf). Another test method that may provide a quantitative assessment of trackability (called Tortuosity Test 2 herein) is described in W. Schmidt, P. Lanzer, P. Behrens, L. D. T. Topoleski, and K.-P. Schmitz "A Comparison of the Mechanical Performance Characteristics of Seven Drug-Eluting Stent Systems" Catheterization and Cardiovascular Interventions 73:350-360 (2009).

In some embodiments, stent system trackability is tested according to Tortuosity test 1. In some embodiments, stent system trackability is tested according to Tortuosity test 2.

Tortuosity Test 1: Trackability testing may be performed according to "New Aspects of in vitro Testing of Arterial Stents based on the new European Standard EN 14299" by Wolfram Schmidt, Peter Behrens, Klaus-Peter Schmitz, Institute for Biomedical Engineering, University of Rostock, Germany at http://www.iib-ev.de/pl/pdf/EN14299.pdf which is incorporated herein by reference in its entirety.

Tortuosity Test 2: Trackability testing may be performed according to W. Schmidt, P. Lanzer, P. Behrens, L. D. T. Topoleski, and K.-P. Schmitz "A Comparison of the Mechanical Performance Characteristics of Seven Drug-Eluting Stent Systems" Catheterization and Cardiovascular Interventions 73:350-360 (2009) which is incorporated herein by reference in its entirety.

FIG. 1 depicts an in-vitro tortuosity fixture 10, such as is used on Tortuosity Test 2 showing various simulated paths of the coronary vasculature. A guiding catheter 2 has been advanced into the aortic arch and its opening 4 is at or about the opening to an artery of the heart. Various arteries branch from this simulated location including the right circumflexus 8. A first path 6a simulates the tortuosity to reach the right posterior venrticule sinistri. A second path 6b and third path 6c simulate the tortuosity to reach the right marginalis sinister and the right postero-lateralis. A fourth path 6d simulates the tortuosity to reach the interverticularis anterior. A fifth path 6e and a sixth path 6f simulate the tortuosity to reach the right diagonalis. A seventh path 6g and an eighth path 6h simulate the tortuosity to reach the right lateralis. For some embodiments, the challenge path used to test the system trackability is the fifth path 6e.

In some embodiments, the balloon comprises a polymer, and the stent mounted on the balloon has a crossing profile of at most 1.12 mm.

In some embodiments, the polymer of the balloon comprises polyamide. In some embodiments, the polymer of the balloon comprises at least one of: polyethylene, polyethylene terephthalate (PET), high density polyethylene (HDPE), Arnitel, Hyrtrel, polyetherether ketone (PEEK), urethane, polyurethane, urethane elastomer, nylon, polyamide, polyether block amide (PEBAX), a block copolymer of any polymer listed herein, Teflon, polyolefin, and a thermoplastic elastomer.

In some embodiments, the coating is at most 20 micrometers in thickness and comprises a polymer. In some embodiments, the coating is at least one of: at most 30 micrometers in thickness, at most 28 micrometers in thickness, at most 25 micrometers in thickness, at most 22 micrometers in thickness, at most 20 micrometers in thickness, at most 18 micrometers in thickness, at most 15 micrometers in thickness, at most 10 micrometers in thickness, and comprises a polymer.

In some embodiments, the polymer of the coating is hydrophilic. In some embodiments, the hydrophilic polymer of the coating comprises PLGA. In some embodiments, the polymer of the coating is bioaborbable. In some embodiments, the polymer of the coating comprises at least one of PLGA, a copolymer comprising PLGA (i.e. a PLGA copolymer), a PLGA copolymer with a ratio of about 40:60 to about 60:40, a PLGA copolymer with a ratio of about 70:30 to about 90:10, a PLGA copolymer having a molecular weight of about 10 kD, a PLGA copolymer having a molecular weight of about 19 kD, PGA poly(glycolide), LPLA poly(l-lactide), DLPLA poly(dl-lactide), PCL poly(e-caprolactone) PDO, poly(dioxolane) PGA-TMC, 85/15 DLPLG p(dl-lactide-co-glycolide), 75/25 DLPL, 65/35 DLPLG, 50/50 DLPLG, TMC poly(trimethylcarbonate), p(CPP:SA) poly(1,3-bis-p-(carboxyphenoxy)propane-co-sebacic acid), and a combination thereof.

In some embodiments, the coating comprises a pharmaceutical agent. In some embodiments, the pharmaceutical agent comprises at least one of rapamycin, a prodrug, a derivative, an analog, a hydrate, an ester, and a salt thereof; wherein at least a portion of the pharmaceutical agent is in crystalline form.

In some embodiments, an uncoated stent strut thickness is at most 64 micrometers. In some embodiments, an uncoated stent strut thickness is at least one of: at most 100 micrometers, at most 90 micrometers, at most 85 micrometers, at most 80 micrometers, at most 75 micrometers, at most 70 micrometers, at most 68 micrometers, at most 65 micrometers, at most 64 micrometers, at most 62 micrometers, at most 60 micrometers, at most 55 micrometers, at most 50 micrometers, at most 45 micrometers, and at most 40 micrometers.

In some embodiments, stent system trackability expressed as peak force over the track length is at most 1 Newton. In some embodiments, stent system trackability expressed as mean force over the track length is at most 0.3 Newtons.

In some embodiments, the stent has a closed cell design. In some embodiments, the stent has an open cell design. In some embodiments, the stent has a hybrid of an open and a closed cell design.

In some embodiments, the elongate member has a useable length of about 140 centimeters. In some embodiments, the elongate member has a useable length of at least one of: about 250 centimeters, about 210 centimeters, about 200 centimeters, about 180 centimeters, about 160 centimeters, about 150 centimeters, about 140 centimeters, about 130 centimeters, and about 110 centimeters. As used with respect to useable length, "about" refers to variability of any of: 1 centimeter, 2 centimeters, 5 centimeters, 10 centimeters, 1-5 centimeters, 2-5 centimeters, 2-10 centimeters, and 5-10 centimeters.

In some embodiments, the stent system trackability is achieved with at least one of: at most 5% coating delamination, at most 10% coating delamination, at most 15% coating delamination, and at most 20% coating delamination. In some embodiments, the stent system trackability is achieved with at least one of: at most about 5% coating delamination, at most about 10% coating delamination, at most about 15% coating delamination, and at most about 20% coating delamination. As used with respect to percent coating delamination, "about" refers to variability of any of: 1%, 2%, 5%, 10%, 15%, 1%-5%, 5%-10%, 1%-15%, and 5%-15%. For example, a delamination that is at most about 5% with a variability of 2% may include delamination of 3% to 7% of the coating. In some embodiments, the coating delamination is tested by visual inspection.

In some embodiments, the stent system trackability is achieved with at least one of: at most 5% coating cracking, at most 10% coating cracking, at most 15% coating cracking, and at most 20% coating cracking. In some embodiments, the stent system trackability is achieved with at least one of: at most about 5% coating cracking, at most about 10% coating cracking, at most about 15% coating cracking, and at most about 20% coating cracking. As used with respect to percent coating cracking, "about" refers to variability of any of: 1%, 2%, 5%, 10%, 15%, 1%-5%, 5%-10%, 1%-15%, and 5%-15%. For example, a cracking that is at most about 5% with a variability of 2% may include cracking of 3% to 7% of the coating. In some embodiments, the coating cracking is tested by visual inspection.

Visual Inspection: Testing of delamination and/or cracking may be achieved by visual inspection. Visual inspection may involve the use of various microscopy techniques which allow visualization of defects in the stent coating.

In order to determine the percentage of delamination, the abluminal surface (or a statistically relevant portion thereof) may be visualized and the total percentage of delamination of the stent may be extrapolated based on the area of delamination and the area of stent (and/or stent coating) visualized. There may be, for example, 9 locations on the stent visualized, corresponding to 3 non-overlapping areas of the distal end of the stent, 3 non-overlapping areas of the proximal end of the stent, and 3 non-overlapping areas of the middle of the stent, wherein none of the 9 areas overlap. The delamination may be scanned before choosing these locations for obvious areas of delamination and these areas additionally included as locations of visual inspection, and the other 9 areas should not overlap these locations if possible based on the level of focus of the device used to visualize the stent abluminal surface.

Likewise, in order to determine the percentage of coating cracking, the abluminal and/or the sidewalls of the stent (or a statistically relevant portion thereof) may be visualized and the total percentage of coating cracking of the stent coating may be extrapolated based on the area of coating cracking and the area of stent coating visualized. The areas of highest stress during stent tracking may be chosen for inspection, which may be the sidewalls of the coated stent, for example. There may be, for example, 9 locations on the stent, visualized, corresponding to 3 non-overlapping areas of the distal end of the stent (whether a sidewall, two sidewalls, an abluminal surface or some combination thereof), 3 non-overlapping areas of the proximal end of the stent (whether a sidewall, two sidewalls, an abluminal surface or some combination thereof), and 3 non-overlapping areas of the middle of the stent (whether a sidewall, two sidewalls, an abluminal surface or some combination thereof), wherein none of the 9 areas overlap. The coating cracking may be scanned before choosing these locations for areas of coating cracking and these should be included as additional locations of visual inspection, and the other 9 areas should not overlap these locations, if possible based on the level of focus of the device used to visualize each coating cracking inspection location.

Pushability

Provided herein is a stent delivery system comprising: an elongate member having an inflation lumen and a guidewire lumen therein; a balloon having an interior that is in fluid communication with the inflation lumen; and a stent comprising a coating mounted on the balloon, in which a stent of about 2.25 mm in diameter to about 4.0 mm in diameter by about 9 mm to about 30 mm in length in an expanded state has a stent system pushability ((Fdist/Fprox)×100%) of at most 18%.

"Pushability" as used herein is defined as the ability of the delivery system to be pushed without bending or buckling. The pushability parameter ((Fdist/Fprox)×100%) can be described as the ability to transmit a proximal push force (Fprox) to the distal part of the stent system (i.e. the force measured at the tip of the system (Fdist). Pushability is essentially the amount of force lost in the system. While this can be a qualitative assessment, it can also be defined by quantitative data, given by the ratio of distal reactive force related to the proximal push force. A total occlusion model may be used which is equipped by two separate load cells (in order to assess distal reactive force and proximal push force). Quantitative assessment can be provided by, for example, the method provided in Schmidt W, Grabow N, Behrens P, Schmitz K-P: "Trackability, Crossability, and Pushability of Coronary Stent Systems—An Experimental Approach" Biomed. Technik 47 (2002), Erg. 1, S. 124-126. Another similar test method provides a quantitative assessment of trackability (called Tortuosity Test 2 herein) is described in W. Schmidt, P. Lanzer, P. Behrens, L. D. T. Topoleski, and K.-P. Schmitz "A Comparison of the Mechanical Performance Characteristics of Seven Drug-Eluting Stent Systems" Catheterization and Cardiovascular Interventions 73:350-360 (2009).

In some embodiments, the stent system pushability is measured according to Tortuosity Test 2.

Tortuosity Test 2: Pushability testing may be performed according to W. Schmidt, P. Lanzer, P. Behrens, L. D. T. Topoleski, and K.-P. Schmitz "A Comparison of the Mechanical Performance Characteristics of Seven Drug-Eluting Stent Systems" Catheterization and Cardiovascular Interventions 73:350-360 (2009) which is incorporated herein by reference in its entirety.

In some embodiments, the balloon comprises a polymer, and the stent mounted on the balloon has a crossing profile of at most 1.06 mm for a 2.25 diameter balloon, at most 1.09 mm for a 2.5 diameter balloon, at most 1.11 mm for a 2.75 diameter balloon, at most 1.12 mm for a 3.0 diameter balloon, at most 1.18 mm for a 3.5 diameter balloon, and at most 1.35 mm for a 4.0 diameter balloon.

In some embodiments, the polymer of the balloon comprises polyamide. In some embodiments, the polymer of the balloon comprises at least one of: polyethylene, polyethylene terephthalate (PET), high density polyethylene (HDPE), Arnitel, Hyrtrel, polyetherether ketone (PEEK), urethane, polyurethane, urethane elastomer, nylon, polyamide, polyether block amide (PEBAX), a block copolymer of any polymer listed herein, Teflon, polyolefin, and a thermoplastic elastomer.

In some embodiments, the coating is at most 20 micrometers in thickness and comprises a polymer. In some embodiments, the coating is at least one of: at most 30 micrometers in thickness, at most 28 micrometers in thickness, at most 25 micrometers in thickness, at most 22 micrometers in thickness, at most 20 micrometers in thickness, at most 18 micrometers in thickness, at most 15 micrometers in thickness, at most 10 micrometers in thickness, and comprises a polymer.

In some embodiments, the polymer of the coating is hydrophilic. In some embodiments, the hydrophilic polymer of the coating comprises PLGA. In some embodiments, the polymer of the coating is bioabsorbable. In some embodiments, the polymer of the coating comprises at least one of PLGA, a copolymer comprising PLGA (i.e. a PLGA copolymer), a PLGA copolymer with a ratio of about 40:60 to about 60:40, a PLGA copolymer with a ratio of about 70:30 to about 90:10, a PLGA copolymer having a molecular weight of about 10 kD, a PLGA copolymer having a molecular weight of about 19 kD, PGA poly(glycolide), LPLA poly(l-lactide), DLPLA poly(dl-lactide), PCL poly(e-caprolactone) PDO, poly(dioxolane) PGA-TMC, 85/15 DLPLG p(dl-lactide-co-glycolide), 75/25 DLPL, 65/35 DLPLG, 50/50 DLPLG, TMC poly(trimethylcarbonate), p(CPP:SA) poly(1,3-bis-p-(carboxyphenoxy)propane-co-sebacic acid), and a combination thereof.

In some embodiments, the coating comprises a pharmaceutical agent. In some embodiments, the pharmaceutical agent comprises at least one of rapamycin, a prodrug, a derivative, an analog, a hydrate, an ester, and a salt thereof; wherein at least a portion of the pharmaceutical agent is in crystalline form.

In some embodiments, an uncoated stent strut thickness of the stent is at most 64 micrometers. In some embodiments, an uncoated stent strut thickness is at least one of: at most 100 micrometers, at most 90 micrometers, at most 85 micrometers, at most 80 micrometers, at most 75 micrometers, at most 70 micrometers, at most 68 micrometers, at most 65 micrometers, at most 64 micrometers, at most 62 micrometers, at most 60 micrometers, at most 55 micrometers, at most 50 micrometers, at most 45 micrometers, and at most 40 micrometers.

In some embodiments, the stent has a closed cell design. In some embodiments, the stent has an open cell design. In some embodiments, the stent has a hybrid of an open and a closed cell design.

In some embodiments, the elongate member has a useable length of about 140 centimeters. In some embodiments, the elongate member has a useable length of at least one of: about 250 centimeters, about 210 centimeters, about 200 centimeters, about 180 centimeters, about 160 centimeters, about 150 centimeters, about 140 centimeters, about 130 centimeters, and about 110 centimeters. As used with respect to useable length, "about" refers to variability of any of: 1 centimeter, 2 centimeters, 5 centimeters, 10 centimeters, 1-5 centimeters, 2-5 centimeters, 2-10 centimeters, and 5-10 centimeters.

In some embodiments, the stent system pushability is achieved with at least one of: at most 5% coating delamination, at most 10% coating delamination, at most 15% coating delamination, and at most 20% coating delamination. In some embodiments, the stent system trackability is achieved with at least one of: at most about 5% coating delamination, at most about 10% coating delamination, at most about 15% coating delamination, and at most about 20% coating delamination. As used with respect to percent coating delamination, "about" refers to variability of any of: 1%, 2%, 5%, 10%, 15%, 1%-5%, 5%-10%, 1%-15%, and 5%-15%. For example, a delamination that is at most about 5% with a variability of 2% may include delamination of 3% to 7% of the coating. In some embodiments, the coating delamination is tested by visual inspection.

In some embodiments, the stent system pushability is achieved with at least one of: at most 5% coating cracking, at most 10% coating cracking, at most 15% coating cracking, and at most 20% coating cracking. In some embodiments, the stent system trackability is achieved with at least one of: at most about 5% coating cracking, at most about 10% coating cracking, at most about 15% coating cracking, and at most about 20% coating cracking. As used with respect to percent coating cracking, "about" refers to variability of any of: 1%, 2%, 5%, 10%, 15%, 1%-5%, 5%-10%, 1%-15%, and 5%-15%. For example, a cracking that is at most about 5% with a variability of 2% may include cracking of 3% to 7% of the coating. In some embodiments, the coating delamination is tested by visual inspection.

Visual Inspection: Testing of delamination and/or cracking may be achieved by visual inspection. Visual inspection may involve the use of various microscopy techniques which allow visualization of defects in the stent coating.

In order to determine the percentage of delamination, the abluminal surface (or a statistically relevant portion thereof) may be visualized and the total percentage of delamination of the stent may be extrapolated based on the area of delamination and the area of stent (and/or stent coating) visualized. There may be, for example, 9 locations on the stent visualized, corresponding to 3 non-overlapping areas of the distal end of the stent, 3 non-overlapping areas of the proximal end of the stent, and 3 non-overlapping areas of the middle of the stent, wherein none of the 9 areas overlap. The delamination may be scanned before choosing these locations for obvious areas of delamination and these areas additionally included as locations of visual inspection, and the other 9 areas should not overlap these locations if possible based on the level of focus of the device used to visualize the stent abluminal surface.

Likewise, in order to determine the percentage of coating cracking, the abluminal and/or the sidewalls of the stent (or a statistically relevant portion thereof) may be visualized and the total percentage of coating cracking of the stent coating may be extrapolated based on the area of coating cracking and the area of stent coating visualized. The areas of highest stress during stent tracking may be chosen for inspection, which may be the sidewalls of the coated stent, for example. There may be, for example, 9 locations on the stent visualized, corresponding to 3 non-overlapping areas of the distal end of the stent (whether a sidewall, two sidewalls, an abluminal surface or some combination thereof), 3 non-overlapping areas of the proximal end of the stent (whether a sidewall, two sidewalls, an abluminal surface or some combination thereof), and 3 non-overlapping areas of the middle of the stent (whether a sidewall, two sidewalls, an abluminal surface or some combination thereof), wherein none of the 9 areas overlap. The coating cracking may be scanned before choosing these locations for areas of coating cracking and these should be included as additional locations of visual inspection, and the other 9 areas should not overlap these locations, if possible based on the level of focus of the device used to visualize each coating cracking inspection location.

Crossability

Provided herein is a stent delivery system comprising: an elongate member having an inflation lumen and a guidewire lumen therein; a balloon having an interior that is in fluid communication with the inflation lumen; and a stent comprising a coating mounted on the balloon, in which a stent of about 2.25 mm in diameter to about 4.0 mm in diameter by about 9 mm to about 30 mm in length in an expanded state has a stent system crossability measured as peak cross force of at most 0.15 Newtons.

Provided herein is a stent delivery system comprising: an elongate member having an inflation lumen and a guidewire lumen therein; a balloon having an interior that is in fluid communication with the inflation lumen; and a stent comprising a coating mounted on the balloon, in which a stent of about 2.25 mm in diameter to about 4.0 mm in diameter by about 9 mm to about 30 mm in length in an expanded state has a stent system crossability measured as mean cross force of less than 0.04 Newtons.

"Crossability" as used herein is defined as the ability of the distal part of the stent system to pass through a narrowed vessel lesion. Crossability (or cross force) can be expressed as a mean cross force, and/or as a peak cross force. Quantitative assessment can be provided by, for example, the method provided in Schmidt W, Grabow N, Behrens P, Schmitz K-P: "Trackability, Crossability, and Pushability of Coronary Stent Systems—An Experimental Approach" Biomed. Technik 47 (2002), Erg. 1, S. 124-126, which is a method used in Tortuosity Test 1 (which is also described in "New Aspects of in vitro Testing of Arterial Stents based on the new European Standard EN 14299" by Wolfram Schmidt, Peter Behrens, Klaus-Peter Schmitz, Institute for Biomedical Engineering, University of Rostock, Germany at http://www.iib-ev.de/pl/pdf/EN14299.pdf). Another test method that may provide a quantitative assessment of trackability (called Tortuosity Test 2 herein) is described in W. Schmidt, P. Lanzer, P. Behrens, L. D. T. Topoleski, and K.-P. Schmitz "A Comparison of the Mechanical Performance Characteristics of Seven Drug-Eluting Stent Systems" Catheterization and Cardiovascular Interventions 73:350-360 (2009).

In some embodiments, the tortuosity fixture and the simulated lesion are configured according to Tortuosity Test 1. In some embodiments, the tortuosity fixture and the simulated lesion are configured according to tortuosity test 2.

Tortuosity Test 1: Crossability testing may be performed according to "New Aspects of in vitro Testing of Arterial Stents based on the new European Standard EN 14299" by Wolfram Schmidt, Peter Behrens, Klaus-Peter Schmitz, Institute for Biomedical Engineering, University of Rostock, Germany at http://www.iib-ev.de/pl/pdf/EN14299.pdf which is incorporated herein by reference in its entirety.

Tortuosity Test 2: Crossability testing may be performed according to W. Schmidt, P. Lanzer, P. Behrens, L. D. T. Topoleski, and K.-P. Schmitz "A Comparison of the Mechanical Performance Characteristics of Seven Drug-Eluting Stent Systems" Catheterization and Cardiovascular Interventions 73:350-360 (2009) which is incorporated herein by reference in its entirety.

In some embodiments, the balloon comprises a polymer, and the stent mounted on the balloon has a crossing profile of at most 1.06 mm for a 2.25 diameter balloon, at most 1.09 mm for a 2.5 diameter balloon, at most 1.11 mm for a 2.75 diameter balloon, at most 1.12 mm for a 3.0 diameter balloon, at most 1.18 mm for a 3.5 diameter balloon, and at most 1.35 mm for a 4.0 diameter balloon.

In some embodiments, the polymer of the balloon comprises polyamide. In some embodiments, the polymer of the balloon comprises at least one of: polyethylene, polyethylene terephthalate (PET), high density polyethylene (HDPE), Arnitel, Hyrtrel, polyetherether ketone (PEEK), urethane, polyurethane, urethane elastomer, nylon, polyamide, polyether block amide (PEBAX), a block copolymer of any polymer listed herein, Teflon, polyolefin, and a thermoplastic elastomer.

In some embodiments, the coating is at most 20 micrometers in thickness and comprises a polymer. In some embodiments, the coating is at least one of: at most 30 micrometers in thickness, at most 28 micrometers in thickness, at most 25 micrometers in thickness, at most 22 micrometers in thickness, at most 20 micrometers in thickness, at most 18 micrometers in thickness, at most 15 micrometers in thickness, at most 10 micrometers in thickness, and comprises a polymer.

In some embodiments, the polymer of the coating is hydrophilic. In some embodiments, the hydrophilic polymer of the coating comprises PLGA. In some embodiments, the polymer of the coating is bioabsorbable. In some embodiments, the polymer of the coating comprises at least one of PLGA, a copolymer comprising PLGA (i.e. a PLGA copolymer), a PLGA copolymer with a ratio of about 40:60 to about 60:40, a PLGA copolymer with a ratio of about 70:30 to about 90:10, a PLGA copolymer having a molecular weight of about 10 kD, a PLGA copolymer having a molecular weight of about 19 kD, PGA poly(glycolide), LPLA poly(l-lactide), DLPLA poly(dl-lactide), PCL poly(e-caprolactone) PDO, poly(dioxolane) PGA-TMC, 85/15 DLPLG p(dl-lactide-co-glycolide), 75/25 DLPL, 65/35 DLPLG, 50/50 DLPLG, TMC poly(trimethylcarbonate), p(CPP:SA) poly(1,3-bis-p-(carboxyphenoxy)propane-co-sebacic acid), and a combination thereof.

In some embodiments, the coating comprises a pharmaceutical agent. In some embodiments, the pharmaceutical agent comprises at least one of rapamycin, a prodrug, a derivative, an analog, a hydrate, an ester, and a salt thereof; wherein at least a portion of the pharmaceutical agent is in crystalline form.

In some embodiments, an uncoated stent strut thickness of the stent is at most 64 micrometers. In some embodiments, an uncoated stent strut thickness is at least one of: at most 100 micrometers, at most 90 micrometers, at most 85 micrometers, at most 80 micrometers, at most 75 micrometers, at most 70 micrometers, at most 68 micrometers, at most 65 micrometers, at most 64 micrometers, at most 62 micrometers, at most 60 micrometers, at most 55 micrometers, at most 50 micrometers, at most 45 micrometers, and at most 40 micrometers.

In some embodiments, the stent system crossability expressed as peak cross force is at most 0.1 Newton. In some embodiments, the stent system crossability expressed as mean cross force is at most 0.03 Newtons.

In some embodiments, the stent has a closed cell design. In some embodiments, the stent has an open cell design. In some embodiments, the stent has a hybrid of an open and a closed cell design.

In some embodiments, the elongate member has a useable length of about 140 centimeters. In some embodiments, the elongate member has a useable length of at least one of: about 250 centimeters, about 210 centimeters, about 200 centimeters, about 180 centimeters, about 160 centimeters, about 150 centimeters, about 140 centimeters, about 130 centimeters, and about 110 centimeters. As used with respect to useable length, "about" refers to variability of any of: 1 centimeter, 2 centimeters, 5 centimeters, 10 centimeters, 1-5 centimeters, 2-5 centimeters, 2-10 centimeters, and 5-10 centimeters.

In some embodiments, the stent system crossability is achieved with at least one of: at most 5% coating delamination, at most 10% coating delamination, at most 15% coating delamination, and at most 20% coating delamination. In some embodiments, the stent system trackability is achieved with at least one of: at most about 5% coating delamination, at most about 10% coating delamination, at most about 15% coating delamination, and at most about 20% coating delamination. As used with respect to percent coating delamination, "about" refers to variability of any of: 1%, 2%, 5%, 10%, 15%, 1%-5%, 5%-10%, 1%-15%, and 5%-15%. For example, a delamination that is at most about 5% with a variability of 2% may include delamination of 3% to 7% of the coating. In some embodiments, the coating delamination is tested by visual inspection.

In some embodiments, the stent system crossability is achieved with at least one of: at most 5% coating cracking, at most 10% coating cracking, at most 15% coating cracking, and at most 20% coating cracking. In some embodiments, the stent system trackability is achieved with at least one of: at most about 5% coating cracking, at most about 10% coating cracking, at most about 15% coating cracking, and at most about 20% coating cracking. As used with respect to percent coating cracking, "about" refers to variability of any of: 1%, 2%, 5%, 10%, 15%, 1%-5%, 5%-10%, 1%-15%, and 5%-15%. For example, a cracking that is at most about 5% with a variability of 2% may include cracking of 3% to 7% of the coating. In some embodiments, the coating delamination is tested by visual inspection.

Visual Inspection: Testing of delamination and/or cracking may be achieved by visual inspection. Visual inspection may involve the use of various microscopy techniques which allow visualization of defects in the stent coating.

In order to determine the percentage of delamination, the abluminal surface (or a statistically relevant portion thereof) may be visualized and the total percentage of delamination of the stent may be extrapolated based on the area of delamination and the area of stent (and/or stent coating) visualized. There may be, for example, 9 locations on the stent visualized, corresponding to 3 non-overlapping areas of the distal end of the stent, 3 non-overlapping areas of the proximal end of the stent, and 3 non-overlapping areas of the middle of the stent, wherein none of the 9 areas overlap. The delamination may be scanned before choosing these locations for obvious areas of delamination and these areas additionally included as locations of visual inspection, and the other 9 areas should not overlap these locations if possible based on the level of focus of the device used to visualize the stent abluminal surface.

Likewise, in order to determine the percentage of coating cracking, the abluminal and/or the sidewalls of the stent (or a statistically relevant portion thereof) may be visualized and the total percentage of coating cracking of the stent coating may be extrapolated based on the area of coating cracking and the area of stent coating visualized. The areas of highest stress during stent tracking may be chosen for inspection, which may be the sidewalls of the coated stent, for example. There may be, for example, 9 locations on the stent visualized, corresponding to 3 non-overlapping areas of the distal end of the stent (whether a sidewall, two sidewalls, an abluminal surface or some combination thereof), 3 non-overlapping areas of the proximal end of the stent (whether a sidewall, two sidewalls, an abluminal surface or some combination thereof), and 3 non-overlapping areas of the middle of the stent (whether a sidewall, two sidewalls, an abluminal surface or some combination thereof), wherein none of the 9 areas overlap. The coating cracking may be scanned before choosing these locations for areas of coating cracking and these should be included as additional locations of visual inspection, and the other 9 areas should not overlap these locations, if possible based on the level of focus of the device used to visualize each coating cracking inspection location.

Multiple Stent Systems Through a Guiding Catheter

Provided herein is a method of concurrently delivering a first coated stent to a first target location in a body and a second coated stent to second target location in the body, the method comprising: advancing a first stent delivery system through a guiding catheter in which the first stent delivery system comprises a first elongate member having a first inflation lumen and a first guidewire lumen therein, a first balloon having a first interior that is in fluid communication with the first inflation lumen; and a first coated stent mounted on the first balloon, and advancing a second stent delivery system through the guiding catheter in which the second stent delivery system comprises a second elongate member having a second inflation lumen and a second guidewire lumen therein, a second balloon having a second interior that is in fluid communication with the second inflation lumen; and a second coated stent mounted on the second balloon, wherein the advancing of the second stent delivery system is performed while the first stent delivery system is also in the guiding catheter.

Figure 2:
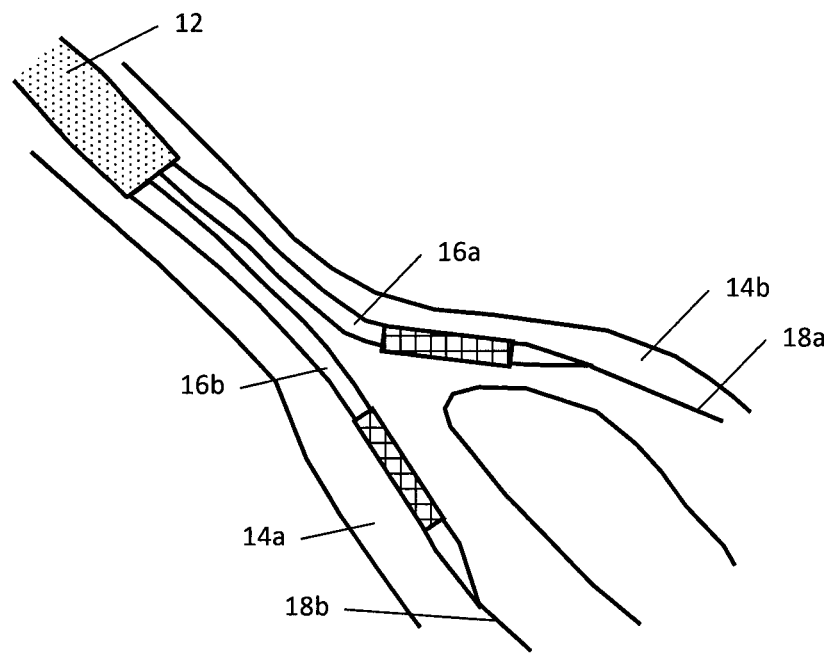
FIG. 2 depicts a stent delivery systems of embodiments described herein advanced through a single guiding catheter concurrently and to two branches of an artery.

FIG. 2 depicts a stent delivery systems 16a, 16b of embodiments described herein advanced through a single guiding catheter 12 concurrently and to two branches 14a, 14b of an artery. Also depicted here are two guidewires 18a and 18b which are passed through the vasculature to the target lesion(s) prior to advancing the respective delivery systems 16a, 16b.

Figure 3A:
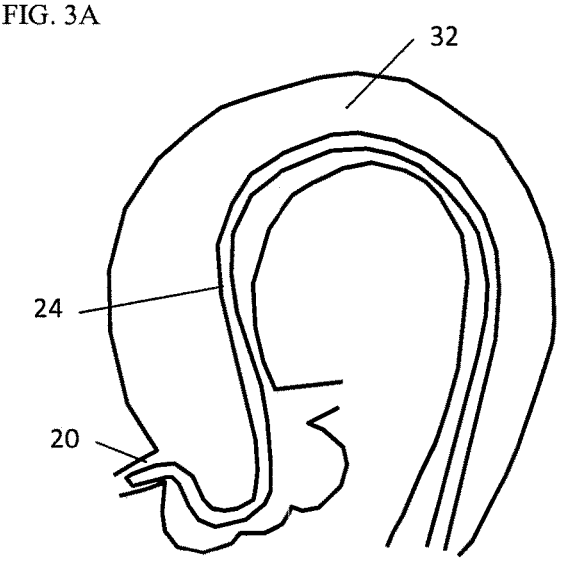
FIGS. 3A-3D depicts a guiding catheters in an aortic arch through which two stent delivery system embodiments described herein may be advanced concurrently to reach two locations in a coronary artery.
Figure 3B:
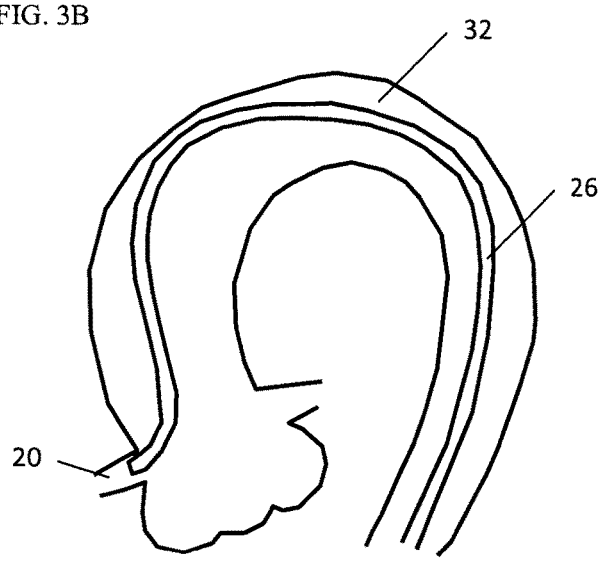
Figure 3C:
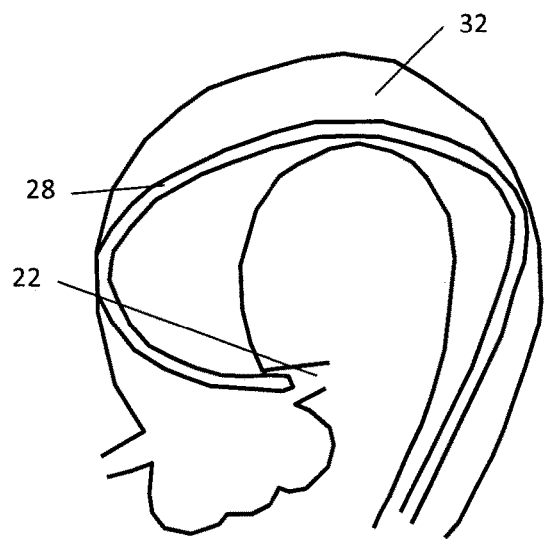
Figure 3D:
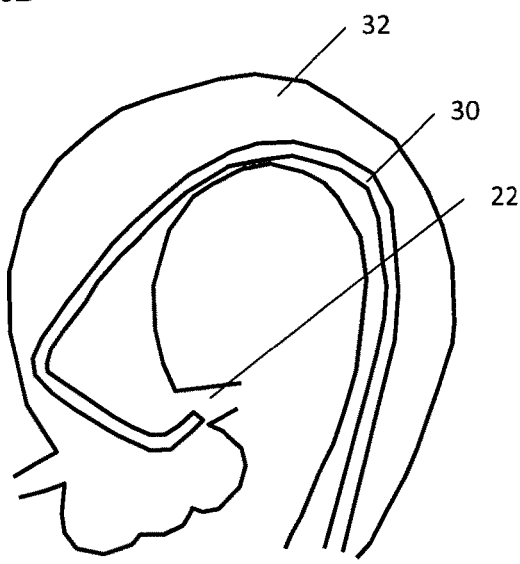

FIGS. 3A-3D depict embodiments of guiding catheters in an aortic arch 32 through which two stent delivery system embodiments described herein may be advanced concurrently to reach two locations in a coronary artery. FIG. 3A shows an Amplatz-like catheter 24 passed over the aortic arch 32 and engaged in the right coronary artery 20. FIG. 3B shows a Judkins-like catheter 26 passed over the aortic arch 32 and minimally engaged in the right coronary artery 20. FIG. 3C shows an EBU-like (extra back-up) catheter 28 passed over the aortic arch 32 and engaged in the left main stem 22. FIG. 3D shows an Judkins-like catheter 30 passed over the aortic arch 32 and engaged in the left main stem 22. Other guiding catheters may be used and are contemplated herein, despite the limited number of guiding catheters depicted in FIGS. 3A-3D. In some embodiments, the guiding catheter is delivered into the aortic arch 32, the delivery systems are passed through the guiding catheter concurrently (or simultaneously), and guidewires guide the delivery systems to different branches of the vasculature (for non-limiting example, the right coronary artery and the left main branch).

In some embodiments, the first balloon comprises a polymer, and the first coated stent mounted on the balloon has a crossing profile of at most 1.06 mm for a 2.25 mm diameter stent, 1.09 mm for a 2.5 mm diameter stent, 1.11 mm for a 2.75 mm diameter stent, 1.12 mm for a 3.0 mm diameter stent, 1.18 mm for a 3.5 mm diameter stent, and 1.25 mm for a 4.0 mm diameter stent, wherein the diameter is an expanded stent diameter.

In some embodiments, the polymer of the first balloon comprises polyamide. In some embodiments, the polymer of the first balloon comprises at least one of: polyethylene, polyethylene terephthalate (PET), high density polyethylene (HDPE), Arnitel, Hyrtrel, polyetherether ketone (PEEK), urethane, polyurethane, urethane elastomer, nylon, polyamide, polyether block amide (PEBAX), a block copolymer of any polymer listed herein, Teflon, polyolefin, and a thermoplastic elastomer.

In some embodiments, the first coated stent comprises a first coating which is at most 20 micrometers in thickness and comprises a polymer. In some embodiments, the coating is at least one of: at most 30 micrometers in thickness, at most 28 micrometers in thickness, at most 25 micrometers in thickness, at most 22 micrometers in thickness, at most 20 micrometers in thickness, at most 18 micrometers in thickness, at most 15 micrometers in thickness, at most 10 micrometers in thickness, and comprises a polymer.

In some embodiments, the first coating is hydrophilic. In some embodiments, the hydrophilic polymer comprises PLGA. In some embodiments, the polymer of the first coating is bioabsorbable. In some embodiments, the polymer of the first coating comprises at least one of PLGA, a copolymer comprising PLGA (i.e. a PLGA copolymer), a PLGA copolymer with a ratio of about 40:60 to about 60:40, a PLGA copolymer with a ratio of about 70:30 to about 90:10, a PLGA copolymer having a molecular weight of about 10 kD, a PLGA copolymer having a molecular weight of about 19 kD, PGA poly(glycolide), LPLA poly(l-lactide), DLPLA poly(dl-lactide), PCL poly(e-caprolactone) PDO, poly(dioxolane) PGA-TMC, 85/15 DLPLG p(dl-lactide-co-glycolide), 75/25 DLPL, 65/35 DLPLG, 50/50 DLPLG, TMC poly(trimethylcarbonate), p(CPP:SA) poly(1,3-bis-p-(carboxyphenoxy)propane-co-sebacic acid), and a combination thereof.

In some embodiments, the second balloon comprises a polymer, and the second coated stent mounted on the balloon has a crossing profile of at most 1.06 mm for a 2.25 mm diameter stent, 1.09 mm for a 2.5 mm diameter stent, 1.11 mm for a 2.75 mm diameter stent, 1.12 mm for a 3.0 mm diameter stent, 1.18 mm for a 3.5 mm diameter stent, and 1.25 mm for a 4.0 mm diameter stent, wherein the diameter is an expanded stent diameter.

In some embodiments, the polymer of the second balloon comprises polyamide. In some embodiments, the polymer of the second balloon comprises at least one of: polyethylene, polyethylene terephthalate (PET), high density polyethylene (HDPE), Arnitel, Hyrtrel, polyetherether ketone (PEEK), urethane, polyurethane, urethane elastomer, nylon, polyamide, polyether block amide (PEBAX), a block copolymer of any polymer listed herein, Teflon, polyolefin, and a thermoplastic elastomer.

In some embodiments, the second coated stent comprises a second coating which is at most 20 micrometers in thickness and comprises a polymer. In some embodiments, the coating is at least one of: at most 30 micrometers in thickness, at most 28 micrometers in thickness, at most 25 micrometers in thickness, at most 22 micrometers in thickness, at most 20 micrometers in thickness, at most 18 micrometers in thickness, at most 15 micrometers in thickness, at most 10 micrometers in thickness, and comprises a polymer.

In some embodiments, the polymer of the second coating is hydrophilic. In some embodiments, the hydrophilic polymer comprises PLGA. In some embodiments, the polymer of the second coating is bioabsorbable. In some embodiments, the polymer of the second coating comprises at least one of PLGA, a copolymer comprising PLGA (i.e. a PLGA copolymer), a PLGA copolymer with a ratio of about 40:60 to about 60:40, a PLGA copolymer with a ratio of about 70:30 to about 90:10, a PLGA copolymer having a molecular weight of about 10 kD, a PLGA copolymer having a molecular weight of about 19 kD, PGA poly(glycolide), LPLA poly(l-lactide), DLPLA poly(dl-lactide), PCL poly(e-caprolactone) PDO, poly(dioxolane) PGA-TMC, 85/15 DLPLG p(dl-lactide-co-glycolide), 75/25 DLPL, 65/35 DLPLG, 50/50 DLPLG, TMC poly(trimethylcarbonate), p(CPP:SA) poly(1,3-bis-p-(carboxyphenoxy)propane-co-sebacic acid), and a combination thereof.

In some embodiments, an uncoated stent strut thickness of the first coated stent is at most 64 micrometers. In some embodiments, an uncoated stent strut thickness of the second coated stent is at most 64 micrometers. In some embodiments, an uncoated stent strut thickness is at least one of: at most 100 micrometers, at most 90 micrometers, at most 85 micrometers, at most 80 micrometers, at most 75 micrometers, at most 70 micrometers, at most 68 micrometers, at most 65 micrometers, at most 64 micrometers, at most 62 micrometers, at most 60 micrometers, at most 55 micrometers, at most 50 micrometers, at most 45 micrometers, and at most 40 micrometers.

In some embodiments, the first stent delivery system and the second stent delivery system are configured to be simultaneously advanced distally.

In some embodiments, the first stent delivery system and the second stent delivery system are configured to be simultaneously withdrawn proximally.

In some embodiments, the first stent delivery system and the second stent delivery system each are manipulable when both systems are within the guiding catheter.

In some embodiments, the guiding catheter is a 7F guiding catheter.

In some embodiments, the first elongate member has a useable length of about 140 centimeters. In some embodiments, the second elongate member has a useable length of about 140 centimeters. In some embodiments, the elongate member has a useable length of at least one of: about 250 centimeters, about 210 centimeters, about 200 centimeters, about 180 centimeters, about 160 centimeters, about 150 centimeters, about 140 centimeters, about 130 centimeters, and about 110 centimeters. As used with respect to useable length, "about" refers to variability of any of: 1 centimeter, 2 centimeters, 5 centimeters, 10 centimeters, 1-5 centimeters, 2-5 centimeters, 2-10 centimeters, and 5-10 centimeters.

Lubricity/Friction Testing

Provided herein is a stent delivery system comprising: an elongate member having an inflation lumen and a guidewire lumen therein; a balloon having an interior that is in fluid communication with the inflation lumen; and a stent comprising a coating mounted on the balloon, wherein when at least a portion of the stent system that includes the mounted stent is tested using Lubricity Test 1, the lubricity is at most 20 g.

"Lubricity" as used herein is defined as how slippery a surface is. A surface is lubricious if it is a slippery surface. A coating on the outer or inner surface of a medical device, such as a catheter or a stent delivery system, is considered lubricious if (when wetted) it can be inserted into the intended body part without leading to injuries and/or causing unacceptable levels of discomfort to the subject. To test lubricity on the bench, in-vitro, a coating is considered lubricious if it has a friction as measured on a Harland FTS5000 Friction Tester (HFT) of 20 g or less, preferably of 15 g or less, at a clamp-force of 300 g, a pull speed of 1 cm/s, a temperature of 22° C. and 35% relative humidity. The test method (herein referred to as Lubricity Test 1) is performed as indicated in US Patent Application 20080292776, which is incorporated here by reference in its entirety, with modification to test method in order to capture the mounted stent lubricity (rather than the catheter lubricity), including adjusting the travel distance (transport movement) to at least the stent length but no more than about 2 cm greater than the stent length, with further adjustment to allow for acceleration time prior to the friction tester pads reaching the mounted stent (about 2 cm in order to account for acceleration time).

In some embodiments, at least the portion of the stent system that includes the mounted stent is tested using Lubricity Test 1 the lubricity is at most 15 g.

Lubricity Test 1: Lubricity may be tested according to US Patent Application 20080292776, which is incorporated here by reference in its entirety.

In some embodiments, the balloon comprises a polymer, and the stent mounted on the balloon has a crossing profile of at most 1.06 mm for a 2.25 diameter balloon, at most 1.09 mm for a 2.5 diameter balloon, at most 1.11 mm for a 2.75 diameter balloon, at most 1.12 mm for a 3.0 diameter balloon, at most 1.18 mm for a 3.5 diameter balloon, and at most 1.35 mm for a 4.0 diameter balloon.

In some embodiments, the polymer of the balloon comprises polyamide. In some embodiments, the polymer of the balloon comprises at least one of: polyethylene, polyethylene terephthalate (PET), high density polyethylene (HDPE), Arnitel, Hyrtrel, polyetherether ketone (PEEK), urethane, polyurethane, urethane elastomer, nylon, polyamide, polyether block amide (PEBAX), a block copolymer of any polymer listed herein, Teflon, polyolefin, and a thermoplastic elastomer.

In some embodiments, the coating is at most 20 micrometers in thickness and comprises a polymer. In some embodiments, the coating is at least one of: at most 30 micrometers in thickness, at most 28 micrometers in thickness, at most 25 micrometers in thickness, at most 22 micrometers in thickness, at most 20 micrometers in thickness, at most 18 micrometers in thickness, at most 15 micrometers in thickness, at most 10 micrometers in thickness, and comprises a polymer.

In some embodiments, the polymer of the coating is hydrophilic. In some embodiments, the hydrophilic polymer of the coating comprises PLGA. In some embodiments, the polymer of the coating is bioabsorbable. In some embodiments, the polymer of the coating comprises at least one of PLGA, a copolymer comprising PLGA (i.e. a PLGA copolymer), a PLGA copolymer with a ratio of about 40:60 to about 60:40, a PLGA copolymer with a ratio of about 70:30 to about 90:10, a PLGA copolymer having a molecular weight of about 10 kD, a PLGA copolymer having a molecular weight of about 19 kD, PGA poly(glycolide), LPLA poly(l-lactide), DLPLA poly(dl-lactide), PCL poly(e-caprolactone) PDO, poly(dioxolane) PGA-TMC, 85/15 DLPLG p(dl-lactide-co-glycolide), 75/25 DLPL, 65/35 DLPLG, 50/50 DLPLG, TMC poly(trimethylcarbonate), p(CPP:SA) poly(1,3-bis-p-(carboxyphenoxy)propane-co-sebacic acid), and a combination thereof.

In some embodiments, the coating comprises a pharmaceutical agent. In some embodiments, the pharmaceutical agent comprises at least one of rapamycin, a prodrug, a derivative, an analog, a hydrate, an ester, and a salt thereof; wherein at least a portion of the pharmaceutical agent is in crystalline form.

In some embodiments, the pharmaceutical agent comprises one or more of rapamycin, biolimus (biolimus A9), 40-O-(2-Hydroxyethyl)rapamycin (everolimus), 40-O-Benzyl-rapamycin, 40-O-(4'-Hydroxymethyl)benzyl-rapamycin, 40-O-[4'-(1,2-Dihydroxyethyl)]benzyl-rapamycin, 40-O-Allyl-rapamycin, 40-O-[3'-(2,2-Dimethyl-1,3-dioxolan-4(S)-yl)-prop-2'-en-1'-yl]-rapamycin, (2':E,4'S)-40-O-(4',5'-Dihydroxypent-2'-en-1'-yl)-rapamycin 40-O-(2-Hydroxy)ethoxycar-bonylmethyl-rapamycin, 40-O-(3-Hydroxy)propyl-rapamycin 4O—O-(6-Hydroxy)hexyl-rapamycin 40-O-[2-(2-Hydroxy)ethoxy]ethyl-rapamycin 4O—O-[(3S)-2,2-Dimethyldioxolan-3-yl]methyl-rapamycin, 40-O-[(2S)-2,3-Dihydroxyprop-1-yl]-rapamycin, 4O—O-(2-Acetoxy)ethyl-rapamycin 4O—O-(2-Nicotinoyloxy)ethyl-rapamycin, 4O—O-[2-(N-Morpholino)acetoxy]ethyl-rapamycin 4O—O-(2-N-Imidazolylacetoxy)ethyl-rapamycin, 40-O-[2-(N-Methyl-N'-piperazinyl)acetoxy]ethyl-rapamycin, 39-O-Desmethyl-39,40-O,O-ethylene-rapamycin, (26R)-26-Dihydro-40-O-(2-hydroxy)ethyl-rapamycin, 28-O-Methyl-rapamycin, 4O—O-(2-Aminoethyl)-rapamycin, 4O—O-(2-Acetaminoethyl)-rapamycin 4O—O-(2-Nicotinamidoethyl)-rapamycin, 4O—O-(2-(N-Methyl-imidazo-2'-ylcarbethoxamido)ethyl)-rapamycin, 4O—O-(2-Ethoxycarbonylaminoethyl)-rapamycin, 40-O-(2-Tolylsulfonamidoethyl)-rapamycin, 40-O-[2-(4',5'-Dicarboethoxy-1',2',3'-triazol-1'-yl)-ethyl]-rapamycin, 42-Epi-(tetrazolyl)rapamycin (tacrolimus), 42-[3-hydroxy-2-(hydroxymethyl)-2-methylpropanoate]rapamycin (temsirolimus), (42S)-42-Deoxy-42-(1H-tetrazol-1-yl)-rapamycin (zotarolimus), picrolimus, novolimus, myolimus, and salts, derivatives, isomers, racemates, diastereoisomers, prodrugs, hydrate, ester, or analogs thereof.

In some embodiments, at least the portion of the stent system that includes the mounted stent is tested using Lubricity Test 1 and has a lubricity of at least one of: at most about 14 g, at most about 13 g, at most about 12 g, at most about 11 g at most about 10 g, at most about 9 g, at most about 8 g, at most about 7 g, at most about 6 g, and at most about 5 g. As used with respect to lubricity, the term "about" refers to variability of any of: 0.5 g, 1 g, 1.5 g, 2 g, 2.5 g, 3 g, 1 g-3 g, 5%, 10%, 15%, 20%, 25%, 35%, 50%, 5%-50%, 10-25%, and 10%-35%.

In some embodiments, the stent has a closed cell design. In some embodiments, the stent has an open cell design. In some embodiments, the stent has a hybrid of an open and a closed cell design.

In some embodiments, the elongate member has a useable length of about 140 centimeters. In some embodiments, the elongate member has a useable length of at least one of: about 250 centimeters, about 210 centimeters, about 200 centimeters, about 180 centimeters, about 160 centimeters, about 150 centimeters, about 140 centimeters, about 130 centimeters, and about 110 centimeters. As used with respect to useable length, "about" refers to variability of any of: 1 centimeter, 2 centimeters, 5 centimeters, 10 centimeters, 1-5 centimeters, 2-5 centimeters, 2-10 centimeters, and 5-10 centimeters.

Surface Hardness

Provided herein is a stent comprising: a coating of at most 20 micrometers thickness comprising polymer and a pharmaceutical agent, in which the coated stent comprises a surface hardness (Hf) of at most 2 GPa when measured by Nanoindentation Test 1. In some embodiments, the coating is at least one of: at most 30 micrometers in thickness, at most 28 micrometers in thickness, at most 25 micrometers in thickness, at most 22 micrometers in thickness, at most 20 micrometers in thickness, at most 18 micrometers in thickness, at most 15 micrometers in thickness, at most 10 micrometers in thickness, and comprises a polymer.

Provided herein is a stent comprising: a coating of at most 20 micrometers thickness comprising polymer and a pharmaceutical agent, in which the coated stent tested in a wetted state comprises a surface hardness (Hf) of at least one of: at most 2 GPa, at most 1.8 GPa, at most 1.6 GPa, at most 1.4 GPa, at most 1.2 GPa, at most 1 GPa, at most 0.8 GPa, at most 0.75 GPa, and at most 0.5 GPa, when measured by Nanoindentation Test 1. In some embodiments, the coating is at least one of: at most 30 micrometers in thickness, at most 28 micrometers in thickness, at most 25 micrometers in thickness, at most 22 micrometers in thickness, at most 20 micrometers in thickness, at most 18 micrometers in thickness, at most 15 micrometers in thickness, at most 10 micrometers in thickness, and comprises a polymer.

Surface Hardness: Nanoindentation is a widely used technique for measuring the hardness (surface hardness) and Young's modulus of many types of thin films. One method for determining the surface hardness of the coating using nanoindentation (Tapping AFM) is found in: Bruno A. Latella, Bee K. Gan, Christophe J. Barbé, and David J. Cassidy "Nanoindentation hardness, Young's modulus, and creep behavior of organic-inorganic silica-based sol-gel thin films on copper" J. Mater. Res., Vol. 23, No. 9: 2357-2365, September 2008 (referred to as Nanoindentation Test 1 herein). In some embodiments, the coating is tested wetted as noted below.

Wetted: The term "wetted" is generally known in the art and—in a broad sense—means "containing water". In particular, the term is used herein to describe a coating that contains sufficient water to be lubricious. In terms of water concentration, in some embodiments a wetted coating contains at least 10 wt % of water based on the dry weight of the coating. In terms of water concentration, in some embodiments a wetted coating contains at least 50 wt % of water based on the dry weight of the coating. In terms of water concentration, in some embodiments a wetted coating contains at least 100 wt % of water based on the dry weight of the coating. Examples of wetting fluids include treated or untreated water, water-containing mixtures with, for example, organic solvents or aqueous solutions. The solvents or aqueous solutions may comprise salts, proteins, or polysaccharides, for example. In some embodiments, the coating (or coated stent) is wetted using a saline solution. In some embodiments, the coating (or coated stent) is wetted by immersing the coated stent in a saline solution for about 5 minutes.

In some embodiments, the coating (or coated stent) is wetted by immersing the coated stent in a saline solution for about 15 minutes. In some embodiments, the coating (or coated stent) is wetted by immersing the coated stent in a saline solution for about 30 minutes. In some embodiments, the coating (or coated stent) is wetted by immersing the coated stent in a saline solution for about 45 minutes. In some embodiments, the coating (or coated stent) is wetted by immersing the coated stent in a saline solution for at least 5 minutes. In some embodiments, the coating (or coated stent) is wetted by immersing the coated stent in a saline solution for at least 15 minutes. In some embodiments, the coating (or coated stent) is wetted by immersing the coated stent in a saline solution for at least 30 minutes. In some embodiments, the coating (or coated stent) is wetted by immersing the coated stent in a saline solution for at least 45 minutes. In some embodiments, the coating (or coated stent) is wetted by immersing the coated stent in a saline solution for between about 5 minutes and about 4 hours. In some embodiments, the coating (or coated stent) is wetted by immersing the coated stent in a saline solution for about 1 hour. In some embodiments, the coating (or coated stent) is wetted by immersing the coated stent in a saline solution for about 1.5 hours. In some embodiments, the coating (or coated stent) is wetted by immersing the coated stent in a saline solution for about 2 hours. In some embodiments, the coating (or coated stent) is wetted by immersing the coated stent in a saline solution for about 2.5 hours. In some embodiments, the coating (or coated stent) is wetted by immersing the coated stent in a saline solution for about 3 hours. In some embodiments, the coating (or coated stent) is wetted by immersing the coated stent in a saline solution for about 3.5 hours. In some embodiments, the coating (or coated stent) is wetted by immersing the coated stent in a saline solution for about 4 hours. In some embodiments, the coating (or coated stent) is wetted by immersing the coated stent in a saline solution for between about 30 minutes and about 1 hour. In some embodiments, the coating (or coated stent) is wetted by immersing the coated stent in a saline solution for between about 30 minutes and about 2 hours. In some embodiments, the coating (or coated stent) is wetted by immersing the coated stent in a saline solution for between about 1 hour and about 2 hours. In some embodiments, the coating (or coated stent) is wetted by immersing the coated stent in a saline solution for between about 2 hours and about 3 hours. In some embodiments, the coating (or coated stent) is wetted by immersing the coated stent in a saline solution for between about 3 hours and about 4 hours. As used herein, the term "about" when used in reference to immersion times for wetting a coated stent can mean variations of at least one of 1%, 5%, 10%, 25%, 50%, 75%, for immersion times less than 10 minutes, variations of 1 minute, 2 minutes, and 3 minutes, for times longer than 1 hour, variations of 1 minute, 5 minutes, 10 minutes, 15 minutes, 20 minutes, 30 minutes, and 45 minutes.

In some embodiments, the polymer comprises PLGA. In some embodiments, the polymer is hydrophilic. In some embodiments, the polymer is bioabsorbable. In some embodiments, the polymer comprises at least one of PLGA, a copolymer comprising PLGA (i.e. a PLGA copolymer), a PLGA copolymer with a ratio of about 40:60 to about 60:40, a PLGA copolymer with a ratio of about 70:30 to about 90:10, a PLGA copolymer having a molecular weight of about 10 kD, a PLGA copolymer having a molecular weight of about 19 kD, PGA poly(glycolide), LPLA poly(l-lactide), DLPLA poly(dl-lactide), PCL poly(e-caprolactone) PDO, poly(dioxalone) PGA-TMC, 85/15 DLPLG p(dl-lactide-co-glycolide), 75/25 DLPL, 65/35 DLPLG, 50/50 DLPLG, TMC poly(trimethylcarbonate), p(CPP:SA) poly(1,3-bis-p-(carboxyphenoxy)propane-co-sebacic acid), and a combination thereof.

In some embodiments, the uncoated stent strut thickness is at most 64 micrometers. In some embodiments, an uncoated stent strut thickness is at least one of: at most 100 micrometers, at most 90 micrometers, at most 85 micrometers, at most 80 micrometers, at most 75 micrometers, at most 70 micrometers, at most 68 micrometers, at most 65 micrometers, at most 64 micrometers, at most 62 micrometers, at most 60 micrometers, at most 55 micrometers, at most 50 micrometers, at most 45 micrometers, and at most 40 micrometers.

In some embodiments, the coating comprises a pharmaceutical agent. In some embodiments, the pharmaceutical agent comprises at least one of rapamycin, a prodrug, a derivative, an analog, a hydrate, an ester, and a salt thereof; wherein at least a portion of the pharmaceutical agent is in crystalline form.

In some embodiments, the pharmaceutical agent comprises one or more of rapamycin, biolimus (biolimus A9), 40-O-(2-Hydroxyethyl)rapamycin (everolimus), 40-O-Benzyl-rapamycin, 40-O-(4'-Hydroxymethyl)benzyl-rapamycin, 40-O-[4'-(1,2-Dihydroxyethyl)]benzyl-rapamycin, 40-O-Allyl-rapamycin, 40-O-[3'-(2,2-Dimethyl-1,3-dioxolan-4(S)-yl)-prop-2'-en-1'-yl]-rapamycin, (2':E,4'S)-40-O-(4',5'-Dihydroxypent-2'-en-1'-yl)-rapamycin 40-O-(2-Hydroxy)ethoxycar-bonylmethyl-rapamycin, 40-O-(3-Hydroxy)propyl-rapamycin 4O—O-(6-Hydroxy)hexyl-rapamycin 40-O-[2-(2-Hydroxy)ethoxy]ethyl-rapamycin 4O—O-[(3S)-2,2-Dimethyldioxolan-3-yl]methyl-rapamycin, 40-O-[(2S)-2,3-Dihydroxyprop-1-yl]-rapamycin, 4O—O-(2-Acetoxy)ethyl-rapamycin 4O—O-(2-Nicotinoyloxy)ethyl-rapamycin, 4O—O-[2-(N-Morpholino)acetoxy]ethyl-rapamycin 4O—O-(2-N-Imidazolylacetoxy)ethyl-rapamycin, 40-O-[2-(N-Methyl-N'-piperazinyl)acetoxy]ethyl-rapamycin, 39-O-Desmethyl-39,40-O,O-ethylene-rapamycin, (26R)-26-Dihydro-40-O-(2-hydroxy)ethyl-rapamycin, 28-O-Methyl-rapamycin, 4O—O-(2-Aminoethyl)-rapamycin, 4O—O-(2-Acetaminoethyl)-rapamycin 4O—O-(2-Nicotinamidoethyl)-rapamycin, 4O—O-(2-(N-Methyl-imidazo-2'-ylcarbethoxamido)ethyl)-rapamycin, 4O—O-(2-Ethoxycarbonylaminoethyl)-rapamycin, 40-O-(2-Tolylsulfonamidoethyl)-rapamycin, 40-O-[2-(4',5'-Dicarboethoxy-1',2',3'-triazol-1'-yl)-ethyl]-rapamycin, 42-Epi-(tetrazolyl)rapamycin (tacrolimus), 42-[3-hydroxy-2-(hydroxymethyl)-2-methylpropanoate]rapamycin (temsirolimus), (42S)-42-Deoxy-42-(1H-tetrazol-1-yl)-rapamycin (zotarolimus), picrolimus, novolimus, myolimus, and salts, derivatives, isomers, racemates, diastereoisomers, prodrugs, hydrate, ester, or analogs thereof.

In some embodiments, the coated stent comprises a surface hardness (Hf) of at least one of: at most 1.5 GPa, at most 1.4 GPa, at most 1.3 GPa, at most 1.2 GPa, at most 1.1 GPa, at most 1.0 GPa, at most 0.9 GPa, at most 0.8 GPa, at most 0.7 GPa, at most 0.6 GPa, at most 0.5 GPa, at most 0.4 GPa, at most 0.3 GPa, and at most 0.2 GPa, when measured by Nanoindentation Test 1. In some embodiments, the coated stent comprises a surface hardness (Hf) of at least one of: at most about 1.5 GPa, at most about 1.4 GPa, at most about 1.3 GPa, at most about 1.2 GPa, at most about 1.1 GPa, at most about 1.0 GPa, at most about 0.9 GPa, at most about 0.8 GPa, at most about 0.7 GPa, at most about 0.6 GPa, at most about 0.5 GPa, at most about 0.4 GPa, at most about 0.3 GPa, and at most about 0.2 GPa, when measured by Nanoindentation Test 1. As used herein, the term "about" when used in reference to surface hardness can mean variations of at least one of 1%, 5%, 10%, 25%, 50%, 75%, 1%-50%, 5%-25%, 25%-50%. and 50%-75%.

In some embodiments, the coated stent is wetted in a saline solution for about 5 minutes prior to surface hardness (Hf) testing. In some embodiments, the coated stent is wetted in a saline solution for about 4 hours prior to surface hardness (Hf) testing.

Systems, devices, and/or methods described herein may comprise the elements described in any of, and/or the methods described in any of: U.S. Provisional Application No. 61/243,955, filed Sep. 18, 2009, U.S. Provisional Application No. 61/212,964, filed Apr. 17, 2009, U.S. Provisional Application No. 61/165,880, filed Apr. 1, 2009, U.S. Provisional Application No. 61/104,669, filed Oct. 10, 2008, U.S. Provisional Application No. 61/045,928, filed Apr. 17, 2008, U.S. Provisional Application No. 60/912,394, filed Apr. 17, 2007, U.S. Provisional Application No. 60/771,725, filed Feb. 8, 2006, U.S. Provisional Application No. 60/752,338, filed Dec. 20, 2005, and the contents of all of these applications are incorporated herein by reference in their entirety.

Systems, devices, and/or methods described herein may comprise the elements described in any of, and/or the methods described in any of: U.S. Provisional Application No. 60/912,408, filed Apr. 17, 2007, U.S. Provisional Application No. 60/884,005, filed Jan. 8, 2007, and U.S. Provisional Application No. 60/981,445, filed Oct. 19, 2007, and the contents of all these applications are incorporated herein by reference in their entirety.

Conventional processes for spray coating stents require that drug and polymer be dissolved in solvent or mutual solvent before spray coating can occur. The platform provided herein the drugs and polymers are coated on the stent framework in discrete steps, which can be carried out simultaneously or alternately. This allows discrete deposition of the active agent (e.g., a drug) within a polymer thereby allowing the placement of more than one drug on a single medical device with or without an intervening polymer layer. For example, the present platform provides a dual drug eluting stent.

Some of the advantages provided by the subject invention include employing compressed fluids (e.g., supercritical fluids, for example e-RESS based methods (which is synonymous with an RESS based method, in some embodiments including electrostatic capture); solvent free deposition methodology; a platform that allows processing at lower temperatures thereby preserving the qualities of the active agent and the polymer; the ability to incorporate two, three or more drugs while minimizing deleterious effects from direct interactions between the various drugs and/or their excipients during the fabrication and/or storage of the drug eluting stents; a dry deposition; enhanced adhesion and mechanical properties of the layers on the stent framework; precision deposition and rapid batch processing; and ability to form intricate structures.

Provided herein is a device comprising a stent; and a plurality of layers that form a laminate coating on said stent; wherein at least one of said layers comprises a bioabsorbable polymer and at least one of said layers comprises one or more active agents; wherein at least a portion of the active agent is in crystalline form.

Provided herein is a device comprising a stent; and a plurality of layers that form a laminate coating on said stent; wherein at least one of said layers comprises a bioabsorbable polymer and at least one of said layers comprises a pharmaceutical agent selected from rapamycin, a prodrug, a derivative, an analog, a hydrate, an ester, and a salt thereof; wherein at least a portion of the pharmaceutical agent is in crystalline form.

In some embodiments, the pharmaceutical agent comprises one or more of rapamycin, biolimus (biolimus A9), 40-O-(2-Hydroxyethyl)rapamycin (everolimus), 40-O-Benzyl-rapamycin, 40-O-(4'-Hydroxymethyl)benzyl-rapamycin, 40-O-[4'-(1,2-Dihydroxyethyl)]benzyl-rapamycin, 40-O-Allyl-rapamycin, 40-O-[3'-(2,2-Dimethyl-1,3-dioxolan-4(S)-yl)-prop-2'-en-1'-yl]-rapamycin, (2':E,4'S)-40-O-(4',5'-Dihydroxypent-2'-en-1'-yl)-rapamycin 40-O-(2-Hydroxy)ethoxycar-bonylmethyl-rapamycin, 40-O-(3-Hydroxy)propyl-rapamycin 4O—O-(6-Hydroxy)hexyl-rapamycin 40-O-[2-(2-Hydroxy)ethoxy]ethyl-rapamycin 4O—O-[(3S)-2,2-Dimethyldioxolan-3-yl]methyl-rapamycin, 40-O-[2S)-2,3-Dihydroxyprop-1-yl]-rapamycin, 4O—O-(2-Acetoxy)ethyl-rapamycin 4O—O-(2-Nicotinoyloxy)ethyl-rapamycin, 4O—O-[2-(N-Morpholino)acetoxy]ethyl-rapamycin 4O—O-(2-N-Imidazolylacetoxy)ethyl-rapamycin, 40-O-[2-(N-Methyl-N'-piperazinyl)acetoxy]ethyl-rapamycin, 39-O-Desmethyl-39,40-O,O-ethylene-rapamycin, (26R)-26-Dihydro-40-O-(2-hydroxy)ethyl-rapamycin, 28-O-Methyl-rapamycin, 4O—O-(2-Aminoethyl)-rapamycin, 4O—O-(2-Acetaminoethyl)-rapamycin 4O—O-(2-Nicotinamidoethyl)-rapamycin, 4O—O-(2-(N-Methyl-imidazo-2'-ylcarbethoxamido)ethyl)-rapamycin, 4O—O-(2-Ethoxycarbonylaminoethyl)-rapamycin, 40-O-(2-Tolylsulfonamidoethyl)-rapamycin, 40-O-[2-(4',5'-Dicarboethoxy-1',2',3'-triazol-1'-yl)-ethyl]-rapamycin, 42-Epi-(tetrazolyl)rapamycin (tacrolimus), 42-[3-hydroxy-2-(hydroxymethyl)-2-methylpropanoate]rapamycin (temsirolimus), (42S)-42-Deoxy-42-(1H-tetrazol-1-yl)-rapamycin (zotarolimus), picrolimus, novolimus, myolimus, and salts, derivatives, isomers, racemates, diastereoisomers, prodrugs, hydrate, ester, or analogs thereof.

In some embodiments, the device has at least one pharmaceutical agent layer defined by a three-dimensional physical space occupied by crystal particles of said pharmaceutical agent and said three dimensional physical space is free of polymer. In some embodiments, at least some of the crystal particles in said three dimensional physical space defining said at least one pharmaceutical agent layer are in contact with polymer particles present in a polymer layer adjacent to said at least one pharmaceutical agent layer defined by said three-dimensional space free of polymer.

In some embodiments, the plurality of layers comprises a first polymer layer comprising a first bioabsorbable polymer and a second polymer layer comprising a second bioabsorbable polymer, wherein said at least one layer comprising said pharmaceutical agent is between said first polymer layer and said second polymer layer. In some embodiments, first and second bioabsorbable polymers are the same polymer. In some embodiments, the first and second bioabsorbable polymers are different. In some embodiments, the second polymer layer has at least one contact point with at least one particle of said pharmaceutical agent in said pharmaceutical agent layer and said second polymer layer has at least one contact point with said first polymer layer.

In some embodiments, the stent has a stent longitudinal axis; and said second polymer layer has a second polymer layer portion along said stent longitudinal wherein said second layer portion is free of contact with particles of said pharmaceutical agent. In some embodiments, the device has at least one pharmaceutical agent layer defined by a three-dimensional physical space occupied by crystal particles of said pharmaceutical agent and said three dimensional physical space is free of polymer.

The second polymer layer may have a layer portion defined along a longitudinal axis of the stent, said polymer layer portion having a thickness less than said maximum thickness of said second polymer layer; wherein said portion is free of contact with particles of said pharmaceutical agent.

The polymer layer portion may be a sub layer which, at least in part, extends along the abluminal surface of the stent along the longitudinal axis of the stent (where the longitudinal axis of the stent is the central axis of the stent along its tubular length). For example, when a coating is removed from the abluminal surface of the stent, such as when the stent is cut along its length, flattened, and the coating is removed by scraping the coating off using a scalpel, knife or other sharp tool, the coating that is removed (despite having a pattern consistent with the stent pattern) has a layer that can be shown to have the characteristics described herein. This may be shown by sampling multiple locations of the coating that is representative of the entire coating.

Alternatively, and/or additionally, since stents are generally comprised of a series of struts and voids. The methods provided herein advantageously allow for coatings extending around each strut, the layers of coating are likewise disposed around each strut. Thus, a polymer layer portion may be a layer which, at least, extends around each strut a distance from said strut (although the distance may vary where the coating thickness on the abluminal surface is different than the coating thickness on the luminal and/or sidewalls).

In some embodiments, the stent comprises at least one strut having a strut length along said stent longitudinal axis, wherein said second layer portion extends substantially along said strut length. In some embodiments, the stent has a stent length along said stent longitudinal axis and said second layer portion extends substantially along said stent length.

In some embodiments, the stent comprises at least five struts, each strut having a strut length along said stent longitudinal axis, wherein said second layer portion extends substantially along substantially the strut length of at least two struts. In some embodiments, the stent comprises at least five struts, each strut having a strut length along said stent longitudinal axis, wherein said second layer portion extends substantially along substantially the strut length of at least three struts. In some embodiments, the stent comprises at least five struts, each strut having a strut length along said stent longitudinal axis, wherein said second layer portion extends substantially along substantially the strut length of least four struts. In some embodiments, the stent comprises at least five struts, each strut having a strut length along said stent longitudinal axis, wherein said second layer portion extends substantially along substantially the strut length of all said at least five struts. In some embodiments, the stent has a stent length along said stent longitudinal axis and said second layer portion extends substantially along said stent length.

In some embodiments, the stent has a stent length along said stent longitudinal axis and said second layer portion extends along at least 50% of said stent length. In some embodiments, the stent has a stent length along said stent longitudinal axis and said second layer portion extends along at least 75% of said stent length. In some embodiments, the stent has a stent length along said stent longitudinal axis and said second layer portion extends along at least 85% of said stent length. In some embodiments, the stent has a stent length along said stent longitudinal axis and said second layer portion extends along at least 90% of said stent length. In some embodiments, the stent has a stent length along said stent longitudinal axis and said second layer portion extends along at least 99% of said stent length.

In some embodiments, the laminate coating has a total thickness and said second polymer layer portion has a thickness of from about 0.01% to about 10% of the total thickness of said laminate coating. In some embodiments, the laminate coating has a total thickness and said horizontal second polymer layer portion has a thickness of from about 1% to about 5% of the total thickness of said laminate coating. In some embodiments, the laminate coating has a total thickness of from about 5 µm to about 50 µm and said horizontal second polymer layer portion has a thickness of from about 0.001 µm to about 5 µm. In some embodiments, the laminate coating has a total thickness of from about 10 µm to about 20 µm and said second polymer layer portion has a thickness of from about 0.01 µm to about 5 µm.

In some embodiments, the laminate coating is at least 25% by volume pharmaceutical agent. In some embodiments, the laminate coating is at least 35% by volume pharmaceutical agent. In some embodiments, the laminate coating is about 50% by volume pharmaceutical agent.

In some embodiments, at least a portion of the pharmaceutical agent is present in a phase separate from one or more phases formed by said polymer.

In some embodiments, the pharmaceutical agent is at least 50% crystalline. In some embodiments, the pharmaceutical agent is at least 75% crystalline. In some embodiments, the pharmaceutical agent is at least 90% crystalline. In some embodiments, the pharmaceutical agent is at least 95% crystalline. In some embodiments, the pharmaceutical agent is at least 99% crystalline.

In some embodiments, the stent has a stent longitudinal length and the coating has a coating outer surface along said stent longitudinal length, wherein said coating comprises pharmaceutical agent in crystalline form present in the coating below said coating outer surface. In some embodiments, the stent has a stent longitudinal length and the coating has a coating outer surface along said stent longitudinal length, wherein said coating comprises pharmaceutical agent in crystalline form present in the coating up to at least 1 µm below said coating outer surface. In some embodiments, the stent has a stent longitudinal length and the coating has a coating outer surface along said stent longitudinal length, wherein said coating comprises pharmaceutical agent in crystalline form present in the coating up to at least 5 µm below said coating outer surface.

In some embodiments, the coating exhibits an X-ray spectrum showing the presence of said pharmaceutical agent in crystalline form. In some embodiments, the coating exhibits a Raman spectrum showing the presence of said pharmaceutical agent in crystalline form. In some embodiments, the coating exhibits a Differential Scanning calorimetry (DSC) curve showing the presence of said pharmaceutical agent in crystalline form. In some embodiments, the coating exhibits Wide Angle X-ray Scattering (WAXS) spectrum showing the presence of said pharmaceutical agent in crystalline form. In some embodiments, the coating exhibits a wide angle radiation scattering spectrum showing the presence of said pharmaceutical agent in crystalline form. In some embodiments, the coating exhibits an Infra Red (IR) spectrum showing the presence of said pharmaceutical agent in crystalline form.

Provided herein is a device comprising: a stent; and a plurality of layers that form a laminate coating on said stent, wherein a first layer comprises a first bioabsorbable polymer, a second layer comprises a pharmaceutical agent, a third layer comprises a second bioabsorbable polymer, a fourth layer comprises the pharmaceutical agent, and a fifth layer comprises a third bioabsorbable polymer, wherein the pharmaceutical agent is selected from rapamycin, a prodrug, a derivative, an analog, a hydrate, an ester, and a salt thereof, and wherein at least a portion of the pharmaceutical agent is in crystalline form.

In some embodiments, the pharmaceutical agent comprises one or more of rapamycin, biolimus (biolimus A9), 40-O-(2-Hydroxyethyl)rapamycin (everolimus), 40-O-Benzyl-rapamycin, 40-O-(4'-Hydroxymethyl)benzyl-rapamycin, 40-O-[4'-(1,2-Dihydroxyethyl)]benzyl-rapamycin, 40-O-Allyl-rapamycin, 40-O-[3'-(2,2-Dimethyl-1,3-dioxolan-4(S)-yl)-prop-2'-en-1'-yl]-rapamycin, (2':E,4'S)-40-O-(4',5'-Dihydroxypent-2'-en-1'-yl)-rapamycin 40-O-(2-Hydroxy)ethoxycar-bonylmethyl-rapamycin, 40-O-(3-Hydroxy)propyl-rapamycin 4O—O-(6-Hydroxy)hexyl-rapamycin 40-O-[2-(2-Hydroxy)ethoxy]ethyl-rapamycin 4O—O-[(3S)-2,2-Dimethyldioxolan-3-yl]methyl-rapamycin, 40-O-[(2S)-2,3-Dihydroxyprop-1-yl]-rapamycin, 4O—O-(2-Acetoxy)ethyl-rapamycin 4O—O-(2-Nicotinoyloxy)ethyl-rapamycin, 40-O-[2-(N-Morpholino)acetoxy]ethyl-rapamycin 4O—O-(2-N-Imidazolylacetoxy)ethyl-rapamycin, 40-O-[2-(N-Methyl-N'-piperazinyl)acetoxy]ethyl-rapamycin, 39-O-Desmethyl-39,40-O,O-ethylene-rapamycin, (26R)-26-Dihydro-40-O-(2-hydroxy)ethyl-rapamycin, 28-O-Methyl-rapamycin, 4O—O-(2-Aminoethyl)-rapamycin, 4O—O-(2-Acetaminoethyl)-rapamycin 4O—O-(2-Nicotinamidoethyl)-rapamycin, 4O—O-(2-(N-Methyl-imidazo-2'-ylcarbethoxamido)ethyl)-rapamycin, 4O—O-(2-Ethoxycarbonylaminoethyl)-rapamycin, 40-O-(2-Tolylsulfonamidoethyl)-rapamycin, 40-O-[2-(4',5'-Dicarboethoxy-1',2',3'-triazol-1'-yl)-ethyl]-rapamycin, 42-Epi-(tetrazolyl)rapamycin (tacrolimus), 42-[3-hydroxy-2-(hydroxymethyl)-2-methylpropanoate]rapamycin (temsirolimus), (42S)-42-Deoxy-42-(1H-tetrazol-1-yl)-rapamycin (zotarolimus), picrolimus, novolimus, myolimus, and salts, derivatives, isomers, racemates, diastereoisomers, prodrugs, hydrate, ester, or analogs thereof.

In some embodiments, at least two of said first bioabsorbable polymer, said second bioabsorbable polymer and said third bioabsorbable polymer are the same polymer. In some embodiments, the first bioabsorbable polymer, the second bioabsorbable polymer and the third bioabsorbable polymer are the same polymer. In some embodiments, at least two of said first bioabsorbable polymer, said second bioabsorbable polymer and said third bioabsorbable polymer are different polymers. In some embodiments, the first bioabsorbable polymer, said second bioabsorbable polymer and said third bioabsorbable polymer are different polymers.

In some embodiments, the third layer has at least one contact point with particles of said pharmaceutical agent in said second layer; and said third layer has at least one contact point with said first layer.

In some embodiments, at least two of the first polymer, the second polymer, and the third polymer are the same polymer, and wherein said same polymer comprises a copolymer comprising PLGA (i.e. a PLGA copolymer). In some embodiments, the third polymer has an in vitro dissolution rate higher than the in vitro dissolution rate of the first polymer. In some embodiments, the third polymer is PLGA copolymer with a ratio of about 40:60 to about 60:40 and the first polymer is a PLGA copolymer with a ratio of about 70:30 to about 90:10. In some embodiments, the third polymer is PLGA copolymer having a molecular weight of about 10 kD and the second polymer is a PLGA copolymer having a molecular weight of about 19 kD.

Provided herein is a device comprising a stent; and a plurality of layers that form a laminate coating on said stent; wherein at least one of said layers comprises a bioabsorbable polymer, at least one of said layers comprises a first active agent and at least one of said layers comprises a second active agent; wherein at least a portion of first and/or second active agents is in crystalline form.

In some embodiments, the bioabsorbable polymer is selected from the group PLGA, PGA poly(glycolide), LPLA poly(l-lactide), DLPLA poly(dl-lactide), PCL poly(e-caprolactone) PDO, poly(dioxolane) PGA-TMC, 85/15 DLPLG p(dl-lactide-co-glycolide), 75/25 DLPL, 65/35 DLPLG, 50/50 DLPLG, TMC poly(trimethylcarbonate), p(CPP:SA) poly(1,3-bis-p-(carboxyphenoxy)propane-co-sebacic acid). In some embodiments, the polymer comprises an intimate mixture of two or more polymers.

In some embodiments, the first and second active agents are independently selected from pharmaceutical agents and active biological agents.

In some embodiments, the stent is formed of stainless steel material. In some embodiments, the stent is formed of a material comprising a cobalt chromium alloy. In some embodiments, the stent is formed from a material comprising the following percentages by weight: about 0.05 to about 0.15 C, about 1.00 to about 2.00 Mn, about 0.04 Si, about 0.03 P, about 0.3 S, about 19.0 to about 21.0 Cr, about 9.0 to about 11.0 Ni, about 14.0 to about 16.00 W, about 3.0 Fe, and Bal. Co. In some embodiments, the stent is formed from a material comprising at most the following percentages by weight: about 0.025 C, about 0.15 Mn, about 0.15 Si, about 0.015 P, about 0.01 S, about 19.0 to about 21.0 Cr, about 33 to about 37 Ni, about 9.0 to about 10.5 Mo, about 1.0 Fe, about 1.0 Ti, and Bal. Co. In some embodiments, thestent is formed from a material comprising L605 alloy.

In some embodiments, the stent has a thickness of from about 50% to about 90% of a total thickness of said device. In some embodiments, the device has a thickness of from about 20 µm to about 500 µm. In some embodiments, the device has a thickness of about 90 µm or less. In some embodiments, the laminate coating has a thickness of from about 5 µm to about 50 µm. In some embodiments, the laminate coating has a thickness of from about 10 µm to about 20 µm. In some embodiments, the stent has a thickness of from about 50 µm to about 80 µm.

Provided herein is a device comprising: a stent, wherein the stent is formed from a material comprising the following percentages by weight: 0.05-0.15 C, 1.00-2.00 Mn, 0.040 Si, 0.030 P, 0.3 S, 19.00-21.00 Cr, 9.00-11.00 Ni, 14.00-16.00 W, 3.00 Fe, and Bal. Co; and a plurality of layers that form a laminate coating on said stent, wherein a first layer comprises a first bioabsorbable polymer, a second layer comprises a pharmaceutical agent, a third layer comprises a second bioabsorbable polymer, a fourth layer comprises the pharmaceutical agent, and a fifth layer comprises a third bioabsorbable polymer, wherein the pharmaceutical agent is selected from rapamycin, a prodrug, a derivative, an analog, a hydrate, an ester, and a salt thereof, wherein at least a portion of the pharmaceutical agent is in crystalline form, and wherein at least one of said first polymer, second polymer and third polymer comprises a PLGA copolymer.

In some embodiments, the pharmaceutical agent comprises one or more of rapamycin, biolimus (biolimus A9), 40-O-(2-Hydroxyethyl)rapamycin (everolimus), 40-O-Benzyl-rapamycin, 40-O-(4'-Hydroxymethyl)benzyl-rapamycin, 40-O-[4'-(1,2-Dihydroxyethyl)]benzyl-rapamycin, 40-O-Allyl-rapamycin, 40-O-[3'-(2,2-Dimethyl-1,3-dioxolan-4(S)-yl)-prop-2'-en-1'-yl]-rapamycin, (2':E,4'S)-40-O-(4',5'-Dihydroxypent-2'-en-1'-yl)-rapamycin 40-O-(2-Hydroxy)ethoxycar-bonylmethyl-rapamycin, 40-O-(3-Hydroxy)propyl-rapamycin 4O—O-(6-Hydroxy)hexyl-rapamycin 40-O-[2-(2-Hydroxy)ethoxy]ethyl-rapamycin 4O—O-[(3S)-2,2-Dimethyldioxolan-3-yl]methyl-rapamycin, 40-O-[(2S)-2,3-Dihydroxyprop-1-yl]-rapamycin, 4O—O-(2-Acetoxy)ethyl-rapamycin 4O—O-(2-Nicotinoyloxy)ethyl-rapamycin, 4O—O-[2-(N-Morpholino)acetoxy] ethyl-rapamycin 4O—O-(2-N-Imidazolylacetoxy)ethyl-rapamycin, 40-O-[2-(N-Methyl-N-piperazinyl)acetoxy]ethyl-rapamycin, 39-O-Desmethyl-39,40-O,O-ethylene-rapamycin, (26R)-26-Dihydro-40-O-(2-hydroxy)ethyl-rapamycin, 28-O-Methyl-rapamycin, 4O—O-(2-Aminoethyl)-rapamycin, 4O—O-(2-Acetaminoethyl)-rapamycin 4O—O-(2-Nicotinamidoethyl)-rapamycin, 4O—O-(2-(N-Methyl-imidazo-2'-ylcarbethoxamido)ethyl)-rapamycin, 4O—O-(2-Ethoxycarbonylaminoethyl)-rapamycin, 40-O-(2-Tolylsulfonamidoethyl)-rapamycin, 40-O-[2-(4',5'-Dicarboethoxy-1',2',3'-triazol-1'-yl)-ethyl]-rapamycin, 42-Epi-(tetrazolyl)rapamycin (tacrolimus), 42-[3-hydroxy-2-(hydroxymethyl)-2-methylpropanoate]rapamycin (temsirolimus), (42S)-42-Deoxy-42-(1H-tetrazol-1-yl)-rapamycin (zotarolimus), picrolimus, novolimus, myolimus, and salts, derivatives, isomers, racemates, diastereoisomers, prodrugs, hydrate, ester, or analogs thereof.

In some embodiments, the device has a pharmaceutical agent content of from about 0.5 µg/mm to about 20 µg/mm. In some embodiments, the device has a pharmaceutical agent content of from about 8 µg/mm to about 12 µg/mm. In some embodiments, the device has a pharmaceutical agent content of from about 5 µg to about 500 µg. In some embodiments, the device has a pharmaceutical agent content of from about 100 µg to about 160 µg. In some embodiments, the device has a pharmaceutical agent content of from about 100 µg to about 160 µg.

Content is expressed herein in units of µg/mm, however, this may simply be converted to µg/mm2 or another amount per area (e.g., µg/cm2).

Provided herein is a method of preparing a device comprising a stent and a plurality of layers that form a laminate coating on said stent; said method comprising: (a) providing a stent; (b) forming a plurality of layers on said stent to form said laminate coating on said stent; wherein at least one of said layers comprises a bioabsorbable polymer and at least one of said layers comprises one or more active agents; wherein at least a portion of the active agent is in crystalline form. The method may further comprise loading the stent on a balloon of a stent delivery catheter.

Provided herein is a method of preparing a device comprising a stent and a plurality of layers that form a laminate coating on said stent; said method comprising: (a) providing a stent; (b) forming a plurality of layers to form said laminate coating on said stent; wherein at least one of said layers comprises a bioabsorbable polymer and at least one of said layers comprises a pharmaceutical agent selected from rapamycin, a prodrug, a derivative, an analog, a hydrate, an ester, and a salt thereof wherein at least a portion of the pharmaceutical agent is in crystalline form. The method may further comprise mounting the stent on a balloon of a stent delivery catheter. In some embodiments, the stent delivery catheter comprises an elongate member having an inflation lumen and a guidewire lumen therein and a balloon having an interior that is in fluid communication with the inflation lumen In some embodiments, the pharmaceutical agent comprises one or more of rapamycin, biolimus (biolimus A9), 40-O-(2-Hydroxyethyl)rapamycin (everolimus), 40-O-Benzyl-rapamycin, 40-O-(4'-Hydroxymethyl)benzyl-rapamycin, 40-O-[4'-(1,2-Dihydroxyethyl)]benzyl-rapamycin, 40-O-Allyl-rapamycin, 40-O-[3'-(2,2-Dimethyl-1,3-dioxolan-4(S)-yl)-prop-2'-en-1'-yl]-rapamycin, (2':E,4'S)-40-O-(4',5'-Dihydroxypent-2'-en-1'-yl)-rapamycin 40-O-(2-Hydroxy)ethoxycar-bonylmethyl-rapamycin, 40-O-(3-Hydroxy)propyl-rapamycin 4O—O-(6-Hydroxy)hexyl-rapamycin 40-O-[2-(2-Hydroxy)ethoxy]ethyl-rapamycin 4O—O-[(3S)-2,2-Dimethyldioxolan-3-yl]methyl-rapamycin, 40-O-[(2S)-2,3-Dihydroxyprop-1-yl]-rapamycin, 4O—O-(2-Acetoxy)ethyl-rapamycin 4O—O-(2-Nicotinoyloxy)ethyl-rapamycin, 4O—O-[2-(N-Morpholino)acetoxy] ethyl-rapamycin 4O—O-(2-N-Imidazolylacetoxy)ethyl-rapamycin, 40-O-[2-(N-Methyl-N'-piperazinyl)acetoxy]ethyl-rapamycin, 39-O-Desmethyl-39,40-O,O-ethylene-rapamycin, (26R)-26-Dihydro-40-O-(2-hydroxy)ethyl-rapamycin, 28-O-Methyl-rapamycin, 4O—O-(2-Aminoethyl)-rapamycin, 4O—O-(2-Acetaminoethyl)-rapamycin 4O—O-(2-Nicotinamidoethyl)-rapamycin, 4O—O-(2-(N-Methyl-imidazo-2'-ylcarbethoxamido)ethyl)-rapamycin, 4O—O-(2-Ethoxycarbonylaminoethyl)-rapamycin, 40-O-(2-Tolylsulfonamidoethyl)-rapamycin, 40-O-[2-(4',5'-Dicarboethoxy-1',2',3'-triazol-1'-yl)-ethyl]-rapamycin, 42-Epi-(tetrazolyl)rapamycin (tacrolimus), 42-[3-hydroxy-2-(hydroxymethyl)-2-methylpropanoate]rapamycin (temsirolimus), (42S)-42-Deoxy-42-(1H-tetrazol-1-yl)-rapamycin (zotarolimus), picrolimus, novolimus, myolimus, and salts, derivatives, isomers, racemates, diastereoisomers, prodrugs, hydrate, ester, or analogs thereof.

Provided herein is a method of preparing a device comprising a stent and a plurality of layers that form a laminate coating on said stent; said method comprising: (a) providing a stent; (b) forming a plurality of layers to form said laminate coating on said stent; wherein at least one of said layers comprises a bioabsorbable polymer and at least one of said layers comprises a pharmaceutical agent selected from rapamycin, a prodrug, a derivative, an analog, a hydrate, an ester, and a salt thereof; wherein at least a portion of the pharmaceutical agent is in crystalline form, wherein said method comprises forming at least one pharmaceutical agent layer defined by a three-dimensional physical space occupied by crystal particles of said pharmaceutical agent and said three dimensional physical space is free of polymer. The method may further comprise mounting the stent on a balloon of a stent delivery catheter. In some embodiments, the stent delivery catheter comprises an elongate member having an inflation lumen and a guidewire lumen therein and a balloon having an interior that is in fluid communication with the inflation lumen In some embodiments, the pharmaceutical agent comprises one or more of rapamycin, biolimus (biolimus A9), 40-O-(2-Hydroxyethyl)rapamycin (everolimus), 40-O-Benzyl-rapamycin, 40-O-(4'-Hydroxymethyl)benzyl-rapamycin, 40-O-[4'-(1,2-Dihydroxyethyl)]benzyl-rapamycin, 40-O-Allyl-rapamycin, 40-O-[3'-(2,2-Dimethyl-1,3-dioxolan-4(S)-yl)-prop-2'-en-1'-yl]-rapamycin, (2':E,4'S)-40-O-(4',5'-Dihydroxypent-2'-en-1'-yl)-rapamycin 40-O-(2-Hydroxy)ethoxycar-bonylmethyl-rapamycin, 40-O-(3-Hydroxy)propyl-rapamycin 4O—O-(6-Hydroxy)hexyl-rapamycin 40-O-[2-(2-Hydroxy)ethoxy]ethyl-rapamycin 4O—O-[(3S)-2,2-Dimethyldioxolan-3-yl]methyl-rapamycin, 40-O-[(2S)-2,3-Dihydroxyprop-1-yl]-rapamycin, 4O—O-(2-Acetoxy)ethyl-rapamycin 4O—O-(2-Nicotinoyloxy)ethyl-rapamycin, 4O—O-[2-(N-Morpholino)acetoxy] ethyl-rapamycin 4O—O-(2-N-Imidazolylacetoxy)ethyl-rapamycin, 40-O-[2-(N-Methyl-N'-piperazinyl)acetoxy]ethyl-rapamycin, 39-O-Desmethyl-39,40-O,O-ethylene-rapamycin, (26R)-26-Dihydro-40-O-(2-hydroxy)ethyl-rapamycin, 28-O-Methyl-rapamycin, 4O—O-(2-Aminoethyl)-rapamycin, 4O—O-(2-Acetaminoethyl)-rapamycin 4O—O-(2-Nicotinamidoethyl)-rapamycin, 4O—O-(2-(N-Methyl-imidazo-2'-ylcarbethoxamido)ethyl)-rapamycin, 4O—O-(2-Ethoxycarbonylaminoethyl)-rapamycin, 40-O-(2-Tolylsulfonamidoethyl)-rapamycin, 40-O-[2-(4',5'-Dicarboethoxy-1',2',3'-triazol-1'-yl)-ethyl]-rapamycin, 42-Epi-(tetrazolyl)rapamycin (tacrolimus), 42-[3-hydroxy-2-(hydroxymethyl)-2-methylpropanoate]rapamycin (temsirolimus), (42S)-42-Deoxy-42-(1H-tetrazol-1-yl)-rapamycin (zotarolimus), picrolimus, novolimus, myolimus, and salts, derivatives, isomers, racemates, diastereoisomers, prodrugs, hydrate, ester, or analogs thereof.

Provided herein is a method of preparing a device comprising a stent and a plurality of layers that form a laminate coating on said stent; said method comprising: (a) providing a stent; (b) discharging at least one pharmaceutical agent and/or at least one active biological agent in dry powder form through a first orifice; (c) forming a supercritical or near supercritical fluid solution comprising at least one supercritical fluid solvent and at least one polymer and discharging said supercritical or near supercritical fluid solution through a second orifice under conditions sufficient to form solid particles of the polymer; (d) depositing the polymer and pharmaceutical agent and/or active biological agent particles onto said substrate, wherein an electrical potential is maintained between the substrate and the polymer and pharmaceutical agent and/or active biological agent particles, thereby forming said coating; and (e) sintering said polymer under conditions that do not substantially modify a morphology of said pharmaceutical agent and/or activity of said biological agent. The method may further comprise mounting the stent on a balloon of a stent delivery catheter. In some embodiments, the stent delivery catheter comprises an elongate member having an inflation lumen and a guidewire lumen therein and a balloon having an interior that is in fluid communication with the inflation lumen In some embodiments, step (b) comprises discharging a pharmaceutical agent selected from rapamycin, a prodrug, a derivative, an analog, a hydrate, an ester, and a salt thereof wherein at least a portion of the pharmaceutical agent is in crystalline form. In some embodiments, the pharmaceutical agent comprises one or more of rapamycin, biolimus (biolimus A9), 40-O-(2-Hydroxyethyl)rapamycin (everolimus), 40-O-Benzyl-rapamycin, 40-O-(4'-Hydroxymethyl)benzyl-rapamycin, 40-O-[4'-(1,2-Dihydroxyethyl)]benzyl-rapamycin, 40-O-Allyl-rapamycin, 40-O-[3'-(2,2-Dimethyl-1,3-dioxolan-4(S)-yl)-prop-2'-en-1'-yl]-rapamycin, (2':E,4'S)-40-O-(4',5'-Dihydroxypent-2'-en-1'-yl)-rapamycin 40-O-(2-Hydroxy)ethoxycar-bonylmethyl-rapamycin, 40-O-(3-Hydroxy)propyl-rapamycin 4O—O-(6-Hydroxy)hexyl-rapamycin 40-O-[2-(2-Hydroxy)ethoxy]ethyl-rapamycin 4O—O-[(3S)-2,2-Dimethyldioxolan-3-yl]methyl-rapamycin, 40-O-[(2S)-2,3-Dihydroxyprop-1-yl]-rapamycin, 4O—O-(2-Acetoxy)ethyl-rapamycin 4O—O-(2-Nicotinoyloxy)ethyl-rapamycin, 4O—O-[2-(N-Morpholino)acetoxy]ethyl-rapamycin 4O—O-(2-N-Imidazolylacetoxy)ethyl-rapamycin, 40-O-[2-(N-Methyl-N'-piperazinyl)acetoxy]ethyl-rapamycin, 39-O-Desmethyl-39,40-O,O-ethylene-rapamycin, (26R)-26-Dihydro-40-O-(2-hydroxy)ethyl-rapamycin, 28-O-Methyl-rapamycin, 4O—O-(2-Aminoethyl)-rapamycin, 4O—O-(2-Acetaminoethyl)-rapamycin 4O—O-(2-Nicotinamidoethyl)-rapamycin, 4O—O-(2-(N-Methyl-imidazo-2'-ylcarbethoxamido)ethyl)-rapamycin, 4O—O-(2-Ethoxycarbonylaminoethyl)-rapamycin, 40-O-(2-Tolylsulfonamidoethyl)-rapamycin, 40-O-[2-(4',5'-Dicarboethoxy-1',2',3'-triazol-1'-yl)-ethyl]-rapamycin, 42-Epi-(tetrazolyl)rapamycin (tacrolimus), 42-[3-hydroxy-2-(hydroxymethyl)-2-methylpropanoate]rapamycin (temsirolimus), (42S)-42-Deoxy-42-(1H-tetrazol-1-yl)-rapamycin (zotarolimus), picrolimus, novolimus, myolimus, and salts, derivatives, isomers, racemates, diastereoisomers, prodrugs, hydrate, ester, or analogs thereof. In some embodiments, step (c) comprises forming solid particles of a bioabsorbable polymer.

In some embodiments, step (e) comprises forming a polymer layer having a length along a horizontal axis of said device wherein said polymer layer has a layer portion along said length, wherein said layer portion is free of pharmaceutical agent.

In some embodiments, step (e) comprises contacting said polymer with a densified fluid. In some embodiments, step (e) comprises contacting said polymer with a densified fluid for a period of time at a temperature of from about 5° C. and 150° C. and a pressure of from about 10 psi to about 500 psi. In some embodiments, step (e) comprises contacting said polymer with a densified fluid for a period of time at a temperature of from about 25° C. and 95° C. and a pressure of from about 25 psi to about 100 psi. In some embodiments, step (e) comprises contacting said polymer with a densified fluid for a period of time at a temperature of from about 50° C. and 85° C. and a pressure of from about 35 psi to about 65 psi.

Provided herein is a method of preparing a device comprising a stent and a plurality of layers that form a laminate coating on said stent; said method comprising: (a) providing a stent; (b) forming a supercritical or near supercritical fluid solution comprising at least one supercritical fluid solvent and a first polymer, discharging said supercritical or near supercritical fluid solution under conditions sufficient to form solid particles of said first polymer, depositing said first polymer particles onto said stent, wherein an electrical potential is maintained between the stent and the first polymer, and sintering said first polymer; (c) depositing pharmaceutical agent particles in dry powder form onto said stent, wherein an electrical potential is maintained between the stent and said pharmaceutical agent particles; and (d) forming a supercritical or near supercritical fluid solution comprising at least one supercritical fluid solvent and a second polymer and discharging said supercritical or near supercritical fluid solution under conditions sufficient to form solid particles of said second polymer, wherein an electrical potential is maintained between the stent and the second polymer, and sintering said second polymer. The method may further comprise mounting the stent on a balloon of a stent delivery catheter. In some embodiments, the stent delivery catheter comprises an elongate member having an inflation lumen and a guidewire lumen therein and a balloon having an interior that is in fluid communication with the inflation lumen In some embodiments, step (c) and step (d) are repeated at least once. In some embodiments, steps (c) and step (d) are repeated 2 to 20 times.

In some embodiments, the pharmaceutical agent is selected from rapamycin, a prodrug, a derivative, an analog, a hydrate, an ester, and a salt thereof; wherein at least a portion of the pharmaceutical agent is in crystalline form. In some embodiments, the pharmaceutical agent comprises one or more of rapamycin, biolimus (biolimus A9), 40-O-(2-Hydroxyethyl)rapamycin (everolimus), 40-O-Benzyl-rapamycin, 40-O-(4'-Hydroxymethyl)benzyl-rapamycin, 40-O-[4'-(1,2-Dihydroxyethyl)]benzyl-rapamycin, 40-O-Allyl-rapamycin, 40-O-[3'-(2,2-Dimethyl-1,3-dioxolan-4(S)-yl)-prop-2'-en-1'-yl]-rapamycin, (2':E,4'S)-40-O-(4',5'-Dihydroxypent-2'-en-1'-yl)-rapamycin 40-O-(2-Hydroxy)ethoxycar-bonylmethyl-rapamycin, 40-O-(3-Hydroxy)propyl-rapamycin 4O—O-(6-Hydroxy)hexyl-rapamycin 40-O-[2-(2-Hydroxy)ethoxy]ethyl-rapamycin 4O—O-[(3S)-2,2-Dimethyldioxolan-3-yl]methyl-rapamycin, 40-O-[(2S)-2,3-Dihydroxyprop-1-yl]-rapamycin, 4O—O-(2-Acetoxy)ethyl-rapamycin 4O—O-(2-Nicotinoyloxy)ethyl-rapamycin, 4O—O-[2-(N-Morpholino)acetoxy]ethyl-rapamycin 4O—O-(2-N-Imidazolylacetoxy)ethyl-rapamycin, 40-O-[2-(N-Methyl-N'-piperazinyl)acetoxy]ethyl-rapamycin, 39-O-Desmethyl-39,40-O,O-ethylene-rapamycin, (26R)-26-Dihydro-40-O-(2-hydroxy)ethyl-rapamycin, 28-O-Methyl-rapamycin, 4O—O-(2-Aminoethyl)-rapamycin, 4O—O-(2-Acetaminoethyl)-rapamycin 4O—O-(2-Nicotinamidoethyl)-rapamycin, 4O—O-(2-(N-Methyl-imidazo-2'-ylcarbethoxamido)ethyl)-rapamycin, 4O—O-(2-Ethoxycarbonylaminoethyl)-rapamycin, 40-O-(2-Tolylsulfonamidoethyl)-rapamycin, 40-O-[2-(4',5'-Dicarboethoxy-1',2',3'-triazol-1'-yl)-ethyl]-rapamycin, 42-Epi-(tetrazolyl)rapamycin (tacrolimus), 42-[3-hydroxy-2-(hydroxymethyl)-2-methylpropanoate]rapamycin (temsirolimus), (42S)-42-Deoxy-42-(1H-tetrazol-1-yl)-rapamycin (zotarolimus), picrolimus, novolimus, myolimus, and salts, derivatives, isomers, racemates, diastereoisomers, prodrugs, hydrate, ester, or analogs thereof. In some embodiments, the first and second polymers are bioabsorbable.

In some embodiments, step (d) comprises forming a polymer layer having a length along a horizontal axis of said device wherein said polymer layer has a layer portion along said length, wherein said layer portion is free of pharmaceutical agent.

In some embodiments, sintering said first and/or sintering said second polymer comprises contacting said first and/or second polymer with a densified fluid.

In some embodiments, the contacting step is carried out for a period of from about 1 minute to about 60 minutes. In some embodiments, the contacting step is carried out for a period of from about 10 minutes to about 30 minutes.

In some embodiments, maintaining said electrical potential between said polymer particles and or pharmaceutical agent particles and said stent comprises maintaining a voltage of from about 5 kvolts to about 100 kvolts. In some embodiments, maintaining said electrical potential between said polymer particles and or pharmaceutical agent particles and said stent comprises maintaining a voltage of from about 20 kvolts to about 30 kvolts.

Provided herein is a device prepared by a process comprising a method as described herein. In some embodiments, the device is a stent. In some embodiments, the stent is mounted to a stent delivery catheter comprising an elongate member having an inflation lumen and a guidewire lumen therein and a balloon having an interior that is in fluid communication with the inflation lumen.

Provided herein is method of treating a subject comprising delivering a device as described herein in a body lumen of the subject.

Provided herein is a method of treating a subject comprising delivering in the body of the subject a device comprising: a stent, wherein the stent is formed from a material comprising the following percentages by weight: 0.05-0.15 C, 1.00-2.00 Mn, 0.040 Si, 0.030 P, 0.3 S, 19.00-21.00 Cr, 9.00-11.00 Ni, 14.00-16.00 W, 3.00 Fe, and Bal. Co; and a plurality of layers that form a laminate coating on said stent, wherein a first layer comprises a first bioabsorbable polymer, a second layer comprises a pharmaceutical agent, a third layer comprises a second bioabsorbable polymer, a fourth layer comprises the pharmaceutical agent, and a fifth layer comprises a third bioabsorbable polymer, wherein the pharmaceutical agent is selected from rapamycin, a prodrug, a derivative, an analog, a hydrate, an ester, and a salt thereof, wherein at least a portion of the pharmaceutical agent is in crystalline form, and wherein at least one of said first polymer, second polymer and third polymer comprises a copolymer comprising PLGA (i.e. a PLGA copolymer). In some embodiments, the pharmaceutical agent comprises one or more of rapamycin, biolimus (biolimus A9), 40-O-(2-Hydroxyethyl)rapamycin (everolimus), 40-O-Benzyl-rapamycin, 40-O-(4'-Hydroxymethyl)benzyl-rapamycin, 40-O-[4'-(1,2-Dihydroxyethyl)]benzyl-rapamycin, 40-O-Allyl-rapamycin, 40-O-[3'-(2,2-Dimethyl-1,3-dioxolan-4(S)-yl)-prop-2'-en-1'-yl]-rapamycin, (2':E,4'S)-40-O-(4',5'-Dihydroxypent-2'-en-1'-yl)-rapamycin 40-O-(2-Hydroxy)ethoxycar-bonylmethyl-rapamycin, 40-O-(3-Hydroxy)propyl-rapamycin 4O—O-(6-Hydroxy)hexyl-rapamycin 40-O-[2-(2-Hydroxy)ethoxy]ethyl-rapamycin 4O—O-[(3S)-2,2-Dimethyldioxolan-3-yl]methyl-rapamycin, 40-O-[(2S)-2,3-Dihydroxyprop-1-yl]-rapamycin, 4O—O-(2-Acetoxy)ethyl-rapamycin 4O—O-(2-Nicotinoyloxy)ethyl-rapamycin, 4O—O-[2-(N-Morpholino)acetoxy]ethyl-rapamycin 4O—O-(2-N-Imidazolylacetoxy)ethyl-rapamycin, 40-O-[2-(N-Methyl-N-piperazinyl)acetoxy]ethyl-rapamycin, 39-O-Desmethyl-39,40-O,O-ethylene-rapamycin, (26R)-26-Dihydro-40-O-(2-hydroxy)ethyl-rapamycin, 28-O-Methyl-rapamycin, 4O—O-(2-Aminoethyl)-rapamycin, 4O—O-(2-Acetaminoethyl)-rapamycin 4O—O-(2-Nicotinamidoethyl)-rapamycin, 40-O-(2-(N-Methyl-imidazo-2'-ylcarbethoxamido)ethyl)-rapamycin, 4O—O-(2-Ethoxycarbonylaminoethyl)-rapamycin, 40-O-(2-Tolylsulfonamidoethyl)-rapamycin, 40-O-[2-(4',5'-Dicarboethoxy-1',2',3'-triazol-1'-yl)-ethyl]-rapamycin, 42-Epi-(tetrazolyl)rapamycin (tacrolimus), 42-[3-hydroxy-2-(hydroxymethyl)-2-methylpropanoate]rapamycin (temsirolimus), (42S)-42-Deoxy-42-(1H-tetrazol-1-yl)-rapamycin (zotarolimus), picrolimus, novolimus, myolimus, and salts, derivatives, isomers, racemates, diastereoisomers, prodrugs, hydrate, ester, or analogs thereof.

In some embodiments, the device has a pharmaceutical agent content of from about 0.5 µg/mm to about 20 µg/mm. In some embodiments, the device has a pharmaceutical agent content of from about 8 µg/mm to about 12 µg/mm. In some embodiments, the device has a pharmaceutical agent content of from about 100 µg to about 160 µg. In some embodiments, the device has a pharmaceutical agent content of from about 120 µg to about 150 µg.

In some embodiments, the device has an initial pharmaceutical agent amount and the amount of pharmaceutical agent delivered by said device to vessel wall tissue of said subject is higher than the amount of pharmaceutical agent delivered by a conventional drug eluting stent having the same initial pharmaceutical agent content as the initial pharmaceutical agent content of said device. In some embodiments, the amount of pharmaceutical agent delivered by said device to vessel wall tissue of said subject is at least 25% more that the amount of pharmaceutical agent delivered to vessel wall tissue of said subject by said conventional drug eluting stent. In some embodiments, the method comprises treating restenosis in a blood vessel of said the subject. In some embodiments, the subject is selected from a pig, a rabbit and a human.

"Vessel wall tissue" as used herein refers to the tissue surrounding the lumen of a vessel, including the endothelium, neointima, tunica media, IEL (internal elastic lamina), EEL (external elastic lamina), and the tunica adventitia.

In some embodiments, the presence of crystallinity is shown by at least one of XRD, Raman Spectroscopy, Infrared analytical methods, and DSC.

In some embodiments, the coating on an abluminal surface of said stent has a greater thickness than coating on a luminal surface of said stent. In some embodiments, the ratio of coating on the abluminal surface to coating on the luminal surface of the device is 80:20. In some embodiments, the ratio of coating on the abluminal surface to coating on the luminal surface of the device is 75:25. In some embodiments, the ratio of coating on the abluminal surface to coating on the luminal surface of the device is 70:30. In some embodiments, the ratio of coating on the abluminal surface to coating on the luminal surface of the device is 60:40.

In some embodiments, the stent is a coronary stent, a vascular stent, a peripheral stent, billiarty stent, and intercranial stent.

EXAMPLES

The following examples are provided to illustrate selected embodiments. They should not be considered as limiting the scope of the invention, but merely as being illustrative and representative thereof. For each example listed below, multiple analytical techniques may be provided. Any single technique of the multiple techniques listed may be sufficient to show the parameter and/or characteristic being tested, or any combination of techniques may be used to show such parameter and/or characteristic. Those skilled in the art will be familiar with a wide range of analytical techniques for the characterization of drug/polymer coatings. Techniques presented here, but not limited to, may be used to additionally and/or alternatively characterize specific properties of the coatings with variations and adjustments employed which would be obvious to those skilled in the art.

Sample Preparation

Generally speaking, coatings on stents, on coupons, or samples prepared for in-vivo models are prepared as below. Nevertheless, modifications for a given analytical method are presented within the examples shown, and/or would be obvious to one having skill in the art. Thus, numerous variations, changes, and substitutions will now occur to those skilled in the art without departing from the invention. It should be understood that various alternatives to the embodiments of the invention described herein and examples provided may be employed in practicing the invention and showing the parameters and/or characteristics described.

Coatings on Stents

Coated stents as described herein and/or made by a method disclosed herein are prepared. In some examples, the coated stents have a targeted thickness of ~15 microns (~5 microns of active agent). In some examples, the coating process is PDPDP (Polymer, sinter, Drug, Polymer, sinter, Drug, Polymer, sinter) using deposition of drug in dry powder form and deposition of polymer particles by RESS methods and equipment described herein. In the illustrations below, resulting coated stents may have a 3-layer coating comprising polymer (for example, PLGA) in the first layer, drug (for example, rapamycin) in a second layer and polymer in the third layer, where a portion of the third layer is substantially drug free (e.g. a sub-layer within the third layer having a thickness equal to a fraction of the thickness of the third layer). As described layer, the middle layer (or drug layer) may be overlapping with one or both first (polymer) and third (polymer) layer. The overlap between the drug layer and the polymer layers is defined by extension of polymer material into physical space largely occupied by the drug. The overlap between the drug and polymer layers may relate to partial packing of the drug particles during the formation of the drug layer. When crystal drug particles are deposited on top of the first polymer layer, voids and or gaps may remain between dry crystal particles. The voids and gaps are available to be occupied by particles deposited during the formation of the third (polymer) layer. Some of the particles from the third (polymer) layer may rest in the vicinity of drug particles in the second (drug) layer. When the sintering step is completed for the third (polymer) layer, the third polymer layer particles fuse to form a continuous film that forms the third (polymer) layer. In some embodiments, the third (polymer) layer however will have a portion along the longitudinal axis of the stent whereby the portion is free of contacts between polymer material and drug particles. The portion of the third layer that is substantially of contact with drug particles can be as thin as 1 nanometer.

Polymer-coated stents having coatings comprising polymer but no drug are made by a method disclosed herein and are prepared having a targeted thickness of, for example, ~5 microns. An example coating process is PPP (PLGA, sinter, PLGA, sinter, PLGA, sinter) using RESS methods and equipment described herein. These polymer-coated stents may be used as control samples in some of the examples, infra.

In some examples, the stents are made of a cobalt-chromium alloy and are 5 to 50 mm in length, preferably 10-20 mm in length, with struts of thickness between 20 and 100 microns, preferably 50-70 microns, measuring from an abluminal surface to a luminal surface, or measuring from a side wall to a side wall. In some examples, the stent may be cut lengthwise and opened to lay flat be visualized and/or assayed using the particular analytical technique provided.

Sample Preparation for In-Vivo Models

Devices comprising stents having coatings disclosed herein are delivered to and implanted to the porcine coronary arteries of pigs (domestic swine, juvenile farm pigs, or Yucatan miniature swine). Porcine coronary stenting is exploited herein since such model yields results that are comparable to other investigations assaying neointimal hyperplasia in human subjects. Deliverability features are assessed during delivery to the arteries of the pigs. In some embodiments, the stents are expanded to a 1:1.1 balloon:artery ratio. At multiple time points, animals may be euthanized (e.g. t=1 day, 7 days, 14 days, 21 days, and 28 days), the stents are explanted, and assayed.

Devices comprising stents having coatings disclosed herein alternatively are implanted in the common iliac arteries of New Zealand white rabbits. The stents are expanded to a 1:1.1 balloon:artery ratio. At multiple time points, animals are euthanized (e.g., t=1 day, 7 days, 14 days, 21 days, and 28 days), the stents are explanted, and assayed.

Example 1

This example illustrates embodiments that provide a coated coronary stent, comprising: a stent framework and a rapamycin-polymer coating wherein at least part of rapamycin is in crystalline form and the rapamycin-polymer coating comprises one or more resorbable polymers.

In these experiments two different polymers were employed:
Polymer A: ~50:50 PLGA-Ester End Group, MW~19 kD, degradation rate ~1-2 months
Polymer B: ~50:50 PLGA-Carboxylate End Group, MW~10 kD, degradation rate ~28 days Metal stents were coated as follows:
AS1: Polymer A/Rapamycin/Polymer A/Rapamycin/Polymer A
AS2: Polymer A/Rapamycin/Polymer A/Rapamycin/Polymer B
AS1 (B) or AS1(213): Polymer B/Rapamycin/Polymer B/Rapamycin/Polymer B
AS1b: Polymer A/Rapamycin/Polymer A/Rapamycin/Polymer A
AS2b: Polymer A/Rapamycin/Polymer A/Rapamycin/Polymer B Example 2—Crystallinity The presence and or quantification of the Active agent crystallinity can be determined from a number of characterization methods known in the art, but not limited to, XRPD, vibrational spectroscopy (FTIR, NR, Raman), polarized optical microscopy, calorimetry, thermal analysis and solid-state NMR.

X-Ray Diffraction to Determine the Presence and/or Quantification of Active Agent Crystallinity Active agent and polymer coated proxy substrates are prepared using 316L stainless steel coupons for X-ray powder diffraction (XRPD) measurements to determine the presence of crystallinity of the active agent. The coating on the coupons is equivalent to the coating on the stents described herein. Coupons of other materials described herein, such as cobalt-chromium alloys, may be similarly prepared and tested. Likewise, substrates such as stents, or other medical devices described herein may be prepared and tested. Where a coated stent is tested, the stent may be cut lengthwise and opened to lay flat in a sample holder.

For example XRPD analyses are performed using an X-ray powder diffractometer (for example, a Bruker D8 Advance X-ray diffractometer) using Cu Kα radiation. Diffractograms are typically collected between 2 and 40 degrees 2 theta. Where required low background XRPD sample holders are employed to minimize background noise.

The diffractograms of the deposited active agent are compared with diffractograms of known crystallized active agents, for example micronized crystalline sirolimus in powder form. XRPD patterns of crystalline forms show strong diffraction peaks whereas amorphous show diffuse and non-distinct patterns. Crystallinity is shown in arbitrary Intensity units.

A related analytical technique which may also be used to provide crystallinity detection is wide angle scattering of radiation (e.g.; Wide Anle X-ray Scattering or WAXS), for example, as described in F. Unger, et al., "Poly(ethylene carbonate): A thermoelastic and biodegradable biomaterial for drug eluting stent coatings?" Journal of Controlled Release, Volume 117, Issue 3, 312-321(2007) for which the technique and variations of the technique specific to a particular sample would be obvious to one of skill in the art.

Raman Spectroscopy

Raman spectroscopy, a vibrational spectroscopy technique, can be useful, for example, in chemical identification, characterization of molecular structures, effects of bonding, identification of solid state form, environment and stress on a sample. Raman spectra can be collected from a very small volume (<1 µm$^3$); these spectra allow the identification of species present in that volume. Spatially resolved chemical information, by mapping or imaging, terms often used interchangeably, can be achieved by Raman microscopy.

Raman spectroscopy and other analytical techniques such as described in Balss, et al., "Quantitative spatial distribution of sirolimus and polymers in drug-eluting stents using confocal Raman microscopy" J. of Biomedical Materials Research Part A, 258-270 (2007), incorporated in its entirety herein by reference, and/or described in Belu et al., "Three-Dimensional Compositional Analysis of Drug Eluting Stent Coatings Using Cluster Secondary Ion Mass Spectroscopy" Anal. Chem. 80: 624-632 (2008) incorporated herein in its entirety by reference may be used.

For example, to test a sample using Raman microscopy and in particular confocal Raman microscopy, it is understood that to get appropriate Raman high resolution spectra sufficient acquisition time, laser power, laser wavelength, sample step size and microscope objective need to be optimized. For example a sample (a coated stent) is prepared as described herein. Alternatively, a coated coupon could be tested in this method. Maps are taken on the coating using Raman microscopy. A WITec CRM 200 scanning confocal Raman microscope using a Nd:YAG laser at 532 nm is applied in the Raman imaging mode. The laser light is focused upon the sample using a 100× dry objective (numerical aperture 0.90), and the finely focused laser spot is scanned into the sample. As the laser scans the sample, over each 0.33 micron interval a Raman spectrum with high signal to noise is collected using 0.3 seconds of integration time. Each confocal cross-sectional image of the coatings displays a region 70 µm wide by 10 µm deep, and results from the gathering of 6300 spectra with a total imaging time of 32 min.

Multivariate analysis using reference spectra from samples of rapamycin (amorphous and crystalline) and polymer are used to deconvolve the spectral data sets, to provide chemical maps of the distribution.

Infrared (IR) Spectroscopy for In-Vitro Testing

Infrared (IR) Spectroscopy such as FTIR and ATR-IR are well utilized techniques that can be applied to show, for example, the quantitative drug content, the distribution of the drug in the sample coating, the quantitative polymer content in the coating, and the distribution of polymer in the coating. Infrared (IR) Spectroscopy such as FTIR and ATR-IR can similarly be used to show, for example, drug crystallinity. The following table (Table 1) lists the typical IR materials for various applications. These IR materials are used for IR windows, diluents or ATR crystals.

TABLE 1

| Material | NaCl | KBr | CsI | AgCl | Ge | ZnSe | Diamond |
|---|---|---|---|---|---|---|---|
| Transmission range (cm−1) | 40,000 ~625 | 40,000 ~400 | 40,000 ~200 | 25,000 ~360 | 5,500 ~625 | 20,000 ~454 | 40,000 ~2,500 & 1667-33 |
| Water sol (g/100 g, 25 C.) | 35.7 | 53.5 | 44.4 | Insol. | Insol. | Insol. | Insol. |

TABLE 1-continued

| Material | NaCl | KBr | CsI | AgCl | Ge | ZnSe | Diamond |
|---|---|---|---|---|---|---|---|
| Attacking materials | Wet Solvents | Wet Solvents | Wet Solvents | Ammonium Salts | H2SO4, aqua regin | Acids, strong alkalies, chlorinated solvents | K2Cr2Os, conc. H2SO4 |

In one test, a coupon of crystalline ZnSe is coated by the processes described herein, creating a PDPDP (Polymer, Drug, Polymer, Drug, Polymer) layered coating that is about 10 microns thick. The coated coupon is analyzed using FTIR. The resulting spectrum shows crystalline drug as determined by comparison to the spectrum obtained for the crystalline form of a drug standard (i.e. a reference spectrum).

Differential Scanning Calorimetry (DSC)

DSC can provide qualitative evidence of the crystallinity of the drug (e.g. rapamycin) using standard DSC techniques obvious to one of skilled in the art. Crystalline melt can be shown using this analytical method (e.g. rapamycin crystalline melting—at about 185 degrees C. to 200 degrees C., and having a heat of fusion at or about 46.8 J/g). The heat of fusion decreases with the percent crystallinity. Thus, the degree of crystallinity could be determined relative to a pure sample, or versus a calibration curve created from a sample of amorphous drug spiked and tested by DSC with known amounts of crystalline drug. Presence (at least) of crystalline drug on a stent could be measured by removing (scraping or stripping) some drug from the stent and testing the coating using the DSC equipment for determining the melting temperature and the heat of fusion of the sample as compared to a known standard and/or standard curve.

Example 3

SEM-In-Vitro Testing-Coating Visualization

Testing of delamination and/or cracking may be achieved by visual inspection. Visual inspection may involve the use of various microscopy techniques which allow visualization of defects in the stent coating.

Testing may be performed prior to and following in-vitro deliverability testing according to Tortuosity Test 1 or Tortuosity Test 2, as noted herein. The dried stent is visualized using SEM for changes in coating.

Testing may be performed prior to and following in-vivo deliverability testing according at time 0. A dried stent is visualized using SEM for changes in coating.

For example the samples are observed by SEM using a Hitachi S-4800 with an accelerating voltage of 800V. Various magnifications may used to evaluate the coating integrity, especially at high strain or high stress regions.

In order to determine the percentage of delamination, the abluminal surface (or a statistically relevant portion thereof) may be visualized and the total percentage of delamination of the stent may be extrapolated based on the area of delamination and the area of stent (and/or stent coating) visualized. There may be, for example, 9 locations on the stent visualized, corresponding to 3 non-overlapping areas of the distal end of the stent, 3 non-overlapping areas of the proximal end of the stent, and 3 non-overlapping areas of the middle of the stent, wherein none of the 9 areas overlap. The delamination may be scanned before choosing these locations for obvious areas of delamination and these areas additionally included as locations of visual inspection, and the other 9 areas should not overlap these locations if possible based on the level of focus of the device used to visualize the stent abluminal surface.

Likewise, in order to determine the percentage of coating cracking, the abluminal and/or the sidewalls of the stent (or a statistically relevant portion thereof) may be visualized and the total percentage of coating cracking of the stent coating may be extrapolated based on the area of coating cracking and the area of stent coating visualized. The areas of highest stress during stent tracking may be chosen for inspection, which may be the sidewalls of the coated stent, for example. There may be, for example, 9 locations on the stent visualized, corresponding to 3 non-overlapping areas of the distal end of the stent (whether a sidewall, two sidewalls, an abluminal surface or some combination thereof), 3 non-overlapping areas of the proximal end of the stent (whether a sidewall, two sidewalls, an abluminal surface or some combination thereof), and 3 non-overlapping areas of the middle of the stent (whether a sidewall, two sidewalls, an abluminal surface or some combination thereof), wherein none of the 9 areas overlap. The coating cracking may be scanned before choosing these locations for areas of coating cracking and these should be included as additional locations of visual inspection, and the other 9 areas should not overlap these locations, if possible based on the level of focus of the device used to visualize each coating cracking inspection location.

Example 4—Preparation of Supercritical Solution Comprising Poly(Lactic-Co-Glycolic Acid) (PLGA) in Hexafluoropropane A view cell at room temperature (with no applied heat) is pressurized with filtered 1,1,1,2,3,3-Hexafluoropropane until it is full and the pressure reaches 4500 psi. Poly(lactic-co-glycolic acid) (PLGA) is added to the cell for a final concentration of 2 mg/ml. The polymer is stirred to dissolve for one hour. The polymer is fully dissolved when the solution is clear and there are no solids on the walls or windows of the cell.

Example 5—Dry Powder Rapamycin Coating on an Electrically Charged L605 Cobalt Chromium Metal Coupon A 1 cm×2 cm L605 cobalt chromium metal coupon serving as a target substrate for rapamycin coating is placed in a vessel and attached to a high voltage electrode. Alternatively, the substrate may be a stent or another biomedical device as described herein, for example. The vessel (V), of approximately 1500 cm$^3$ volume, is equipped with two separate nozzles through which rapamycin or polymers could be selectively introduced into the vessel. Both nozzles are grounded. Additionally, the vessel (V) is equipped with a separate port was available for purging the vessel. Upstream of one nozzle (D) is a small pressure vessel (PV) approximately 5 cm$^3$ in volume with three ports to be used as inlets and outlets. Each port is equipped with a valve which could be actuated opened or closed. One port, port (1) used as an inlet, is an addition port for the dry powdered rapamycin. Port (2), also an inlet is used to feed pressurized gas, liquid, or supercritical fluid into PV. Port (3), used as an outlet, is used to connect the pressure vessel (PV) with nozzle (D) contained in the primary vessel (V) with the target coupon.

Dry powdered Rapamycin obtained from LC Laboratories in a predominantly crystalline solid state, 50 mg milled to an average particle size of approximately 3 microns, is loaded into (PV) through port (1) then port (1) is actuated to the closed position. The metal coupon is then charged to +7.5 kV using a Glassman Series EL high-voltage power source. The drug nozzle on port has a voltage setting of −7.5 kV. After approximately 60-seconds, the drug is injected and the voltage is eliminated. Upon visual inspection of the coupon using an optical microscope, the entire surface area of the coupon is examined for relatively even distribution of powdered material. X-ray diffraction (XRD) is performed as described herein to confirm that the powdered material is largely crystalline in nature as deposited on the metal coupon. UV-Vis and FTIR spectroscopy is performed as describe herein to confirm that the material deposited on the coupon is rapamycin.

Example 6—Polymer Coating on an Electrically Charged L605 Coupon Using Rapid Expansion from a Liquefied Gas A coating apparatus as described in Example 5 above is used in the foregoing example. In this example the second nozzle, nozzle (P), is used to feed precipitated polymer particles into vessel (V) to coat a L605 coupon. Alternatively, the substrate may be a stent or another biomedical device as described herein, for example. Nozzle (P) is equipped with a heater and controller to minimize heat loss due to the expansion of liquefied gases. Upstream of nozzle (P) is a pressure vessel, (PV2), with approximately 25-cm3 internal volume. The pressure vessel (PV2) is equipped with multiple ports to be used for inlets, outlets, thermocouples, and pressure transducers. Additionally, (PV2) is equipped with a heater and a temperature controller. Each port is connected to the appropriate valves, metering valves, pressure regulators, or plugs to ensure adequate control of material into and out of the pressure vessel (PV2). One outlet from (PV2) is connected to a metering valve through pressure rated tubing which was then connected to nozzle (P) located in vessel (V). In the experiment, 150 mg of poly(lactic-co-glycolic acid) (PLGA) is added to pressure vessel (PV2). 1,1,1,2,3,3-hexafluoropropane is added to the pressure vessel (PV2) through a valve and inlet. Pressure vessel (PV2) is set at room temperature with no applied heat and the pressure is 4500 psi. Nozzle (P) is heated to 150° C. A 1-cm×2-cm L605 coupon is placed into vessel (V), attached to an electrical lead and heated via a heat block 110° C. Nozzle (P) is attached to ground. The voltage is set on the polymer spray nozzle and an emitter=pair beaker to a achieve a current greater than or equal to 0.02 mAmps using a Glassman high-voltage power source at which point the metering valve is opened between (PV2) and nozzle (P) in pressure vessel (PV). Polymer dissolved in liquefied gas and is fed at a constant pressure of 200 psig into vessel (V) maintained at atmospheric pressure through nozzle (P) at an approximate rate of 3.0 $cm^3$/min. After approximately 5 seconds, the metering valve is closed discontinuing the polymer-solvent feed. Vessel (V) is Nitrogen gas for 30 seconds to displace the fluorocarbon. After approximately 30 seconds, the metering valve is again opened for a period of approximately 5 seconds and then closed. This cycle is repeated about 4 times. After an additional 1-minute the applied voltage to the coupon was discontinued and the coupon was removed from pressure vessel (V). Upon inspection by optical microscope, a polymer coating is examined for even distribution on all non-masked surfaces of the coupon.

Example 7—Coating of a Metal Cardiovascular Stent with Crystalline Rapamycin and Poly(Lactic-Co-Glycolic Acid) (PLGA)

The apparatus described in Examples 5 and 6 is used in the foregoing example. The metal stent used is made from cobalt chromium alloy of a nominal size of 18 mm in length with struts of 63 microns in thickness measuring from an abluminal surface to a luminal surface, or measuring from a side wall to a side wall. The stent is coated in an alternating fashion whereby the first coating layer of drug is followed by a layer of polymer. These two steps, called a drug/polymer cycle, are repeated twice so there are six layers in an orientation of drug-polymer-drug-polymer-drug-polmer. After completion of each polymer coating step and prior the application of the next drug coating step, the stent is first removed from the vessel (V) and placed in a small pressure vessel where it is exposed to supercritical hexafluoropropane.

Example 8—Layered Coating of a Cardiovascular Stent with an Anti-Restenosis Therapeutic and Polymer in Layers to Control Drug Elution Characteristics A cardiovascular stent is coated using the methods described in Examples herein. The stent is coated in such as way that the drug and polymer are in alternating layers. The first application to the bare stent is a thin layer of a non-resorbing polymer, approximately 2-microns thick. The second layer is a therapeutic agent with anti-restenosis indication. Approximately 35 micrograms are added in this second layer. A third layer of polymer is added at approximately 2-microns thick, followed by a fourth drug layer which is composed of about 25 micrograms of the anti-restenosis agent. A fifth polymer layer, approximately 1-micron thick is added to stent, followed by the sixth layer that includes the therapeutic agent of approximately 15-micrograms. Finally, a last polymer layer is added to a thickness of about 2-microns. After the coating procedure, the stent is annealed using carbon dioxide as described in Example 4 above. In this example a drug eluting stent (DES) is described with low initial drug “burst” properties by virtue of a “sequestered drug layering” process, not possible in conventional solvent-based coating processes. Additionally, by virtue of a higher concentration of drug at the stent ‘inter-layer’ the elution profile is expected to reach as sustained therapeutic release over a longer period of time.

Example 9—Layered Coating of a Cardiovascular Stent with an Anti-Restenosis Therapeutic and an Anti-Thrombotic Therapeutic in a Polymer In one test, devices were coated tested using this method. In these experiments two different polymers were employed: Polymer A: −50:50 PLGA-Ester End Group, MW~19 kD, degradation rate ~70 days; Polymer B: −50:50 PLGA- Carboxylate End Group, MW~10 kD, degradation rate ~28 days. Metal stents were coated as follows: AS1: (n=6) Polymer A/Rapamycin/Polymer A/Rapamycin/Polymer A; AS2: (n=6) Polymer A/Rapamycin/Polymer A/Rapamycin/ Polymer B; AS1(213): (n=6) Polymer B/Rapamycin/Polymer B/Rapamycin/Polymer B; AS1b: (n=6) Polymer A/Rapamycin/Polymer A/Rapamycin/Polymer A; AS2b: (n=6) Polymer A/Rapamycin/Polymer A/Rapamycin/Polymer B.

In this example, after a first polymer layer of approximately 2-microns thick, a drug with anti-thrombotic indication is added in a layer of less than 2-microns in thickness. A third layer consisting of the non-resorbing polymer is added to a thickness of about 4-microns. Next another drug layer is added, a different therapeutic, with an anti-restenosis indication. This layer contains approximately 100 micrograms of the anti-restenosis agent. Finally, a polymer layer approximately 2-microns in thickness is added to the stent. After coating the stent is treated as described in example 20 to sinter the coating using hexafluoropropane.

Example 10—Coating of Stent with Rapamycin and Poly(Lactic-Co-Glycolic Acid) (PLGA)

Micronized Rapamycin is purchased from LC Laboratories. 50:50 PLGA (Mw=~90) are purchased from Aldrich Chemicals. Eurocor CoCr (7 cell) stents are used. The stents are coated by dry electrostatic capture followed by supercritical fluid sintering, using 3 stents/coating run and 3 runs/data set. Analysis of the coated stents is performed by multiple techniques on both stents and coupons with relevant control experiments described herein.

In this example, PLGA is dissolved in 1,1,1,2,3,3-Hexafluoropropane with the following conditions: a) room temperature, with no applied heat; b) 4500 psi; and c) at 2 mg/ml concentration. The spray line is set at 4500 psi, 150° C. and nozzle temperature at 150° C. The solvent (Hexafluoropropane) is rapidly vaporized when coming out of the nozzle (at 150° C.). A negative voltage is set on the polymer spray nozzle to achieve a current of greater than or equal to 0.02 mAmps. The stent is loaded and polymer is sprayed for 15 seconds to create a first polymer coating.

The stent is then transferred to a sintering chamber that is at 75° C. The solvent, in this example 1, 1,2,3,3-hexafluoropropane, slowly enters the sintering chamber to create a pressure at 23 to 27 psi. Stents are sintered at this pressure for 10 minutes.

11.5 mg Rapamycin is loaded into the Drug injection port. The injection pressure is set at 280 psi with +7.5 kV for the stent holder and -7.5 kV for the drug injection nozzle. After the voltage is set for 60 s, the drug is injected into the chamber to create a first drug coating.

A second polymer coating is applied with two 15 second sprays of dissolved polymer with the above first polymer coating conditions. The second coating is also subsequently sintered in the same manner.

A second drug coating is applied with the same parameters as the first drug coating. Lastly, the outer polymer layer is applied with three 15 second sprays of dissolved polymer with the above polymer coating conditions and subsequently sintered.

Example 11—Tortuosity Test 1 with Delamination and/or Cracking Testing

A 3.0 diameter cardiovascular stent is coated using the methods described herein. The stent is mounted to the balloon of a catheter, wherein the balloon comprises polyamide, resulting in a maximum outer diameter (profile) of the mounted (crimped) stent of 1.12 mm. The trackability, pushability, and/or crossability is tested according to Tortuosity Test 1 (according to "New Aspects of in vitro Testing of Arterial Stents based on the new European Standard EN 14299" by Wolfram Schmidt, Peter Behrens, Klaus-Peter Schmitz, Institute for Biomedical Engineering, University of Rostock, Germany at http://www.iib-ev.de/pl/pdf/EN14299.pdf which is incorporated herein by reference in its entirety).

The delamination and/or cracking of the stent coating may also be determined following the Tortuosity testing by visual inspection using, for example, SEM, as noted in Example 3.

Example 12—Tortuosity Test 2 with Delamination and/or Cracking Testing

A 3.0 diameter cardiovascular stent is coated using the methods described herein. The stent is mounted to the balloon of a catheter, resulting in a maximum outer diameter (profile) of the mounted (crimped) stent of 1.12 mm. The system trackability, pushability, and/or crossability is tested according to Tortuosity Test 2 (according to W. Schmidt, P. Lanzer, P. Behrens, L. D. T. Topoleski, and K.-P. Schmitz "A Comparison of the Mechanical Performance Characteristics of Seven Drug-Eluting Stent Systems" Catheterization and Cardiovascular Interventions 73:350-360 (2009) which is incorporated herein by reference in its entirety).

The delamination and/or cracking of the stent coating may also be determined following the Tortuosity testing by visual inspection using, for example, SEM, as noted in Example 3.

Example 13—Delamination and/or Cracking

A 3.0 diameter cardiovascular stent is coated using the methods described herein. The stent is mounted to the balloon of a catheter resulting in a maximum outer diameter (profile) of the mounted (crimped) stent of 1.12 mm.

The stent is run through a tortuosity fixture simulating a delivery path for reaching a coronary artery at least once. The fixture, for example, may be from Tortuosity Test 1 or Tortuosity Test 2. Delamination and/or cracking of the stent coating is determined following the Tortuosity testing by visual inspection using, for example, SEM, as noted in Example 3.

Example 14—Multiple Sizes

At least one of the following is made:
A 2.25 diameter cardiovascular stent is coated using the methods described herein. The stent is mounted to the balloon of a catheter, resulting in a maximum outer diameter (profile) of the mounted (crimped) stent of 1.06 mm.
A 2.5 diameter cardiovascular stent is coated using the methods described herein. The stent is mounted to the balloon of a catheter, resulting in a maximum outer diameter (profile) of the mounted (crimped) stent of 1.09 mm.
A 2.75 diameter cardiovascular stent is coated using the methods described herein. The stent is mounted to the balloon of a resulting in a maximum outer diameter (profile) of the mounted (crimped) stent of 1.11 mm.
A 3.0 diameter cardiovascular stent is coated using the methods described herein. The stent is mounted to the balloon of a catheter, resulting in a maximum outer diameter (profile) of the mounted (crimped) stent of 1.12 mm.

A 3.5 diameter cardiovascular stent is coated using the methods described herein. The stent is mounted to the balloon of a catheter, resulting in a maximum outer diameter (profile) of the mounted (crimped) stent of 1.18 mm.

A 4.0 diameter cardiovascular stent is coated using the methods described herein. The stent is mounted to the balloon of a catheteride, resulting in a maximum outer diameter (profile) of the mounted (crimped) stent of 1.25 mm.

The stent is run through a tortuosity fixture simulating a delivery path for reaching a coronary artery at least once. The fixture, for example, may be from Tortuosity Test 1 or Tortuosity Test 2. Delamination and/or cracking of the stent coating is determined following the Tortuosity testing by visual inspection using, for example, SEM, as noted in Example 3.

Additionally and/or alternatively, the stent is tested according to Tortuosity Test 1 or Tortuosity Test 2. The system trackability, pushability, and/or crossability is determined as noted in the respective Tortuosity Test (1 or 2).

Example 15—Multiple Systems Through a Guiding Catheter

At least two of the following is made (which may be two systems of different sizes, or 2 systems of a same size):

A 2.25 diameter cardiovascular stent is coated using the methods described herein. The stent is mounted to the balloon of a catheter, resulting in a maximum outer diameter (profile) of the mounted (crimped) stent of 1.06 mm.

A 2.5 diameter cardiovascular stent is coated using the methods described herein. The stent is mounted to the balloon of a catheter, resulting in a maximum outer diameter (profile) of the mounted (crimped) stent of 1.09 mm.

A 2.75 diameter cardiovascular stent is coated using the methods described herein. The stent is mounted to the balloon of a catheter, resulting in a maximum outer diameter (profile) of the mounted (crimped) stent of 1.11 mm.

A 3.0 diameter cardiovascular stent is coated using the methods described herein. The stent is mounted to the balloon of a catheter, resulting in a maximum outer diameter (profile) of the mounted (crimped) stent of 1.12 mm.

A 3.5 diameter cardiovascular stent is coated using the methods described herein. The stent is mounted to the balloon of a catheter, resulting in a maximum outer diameter (profile) of the mounted (crimped) stent of 1.18 mm.

A 4.0 diameter cardiovascular stent is coated using the methods described herein. The stent is mounted to the balloon of a catheter, resulting in a maximum outer diameter (profile) of the mounted (crimped) stent of 1.25 mm.

The two systems are delivered concurrently, each to a location in the patient's coronary arterial system (which may be separate arteries or the same artery), by advancing the first system through a 7F guiding catheter such that the stent reaches a first location in the patient's coronary arterial system and delivering said stent to such first location, and, without removing the first system, advancing the second system through the same 7F guiding catheter such that the stent reaches a second location in the patient's coronary arterial system and delivering said stent to such second location. Both systems are then removed from the patient's vasculature.

Example 16—Multiple Systems Through a Guiding Catheter

At least two of the following is made (which may be two systems of different sizes, or 2 systems of a same size):

A 2.25 diameter cardiovascular stent is coated using the methods described herein. The stent is mounted to the balloon of a catheter resulting in a maximum outer diameter (profile) of the mounted (crimped) stent of 1.06 mm.

A 2.5 diameter cardiovascular stent is coated using the methods described herein. The stent is mounted to the balloon of a catheter, resulting in a maximum outer diameter (profile) of the mounted (crimped) stent of 1.09 mm A 2.75 diameter cardiovascular stent is coated using the methods described herein. The stent is mounted to the balloon of a catheter, resulting in a maximum outer diameter (profile) of the mounted (crimped) stent of 1.11 mm A 3.0 diameter cardiovascular stent is coated using the methods described herein. The stent is mounted to the balloon of a catheter, resulting in a maximum outer diameter (profile) of the mounted (crimped) stent of 1.12 mm.

A 3.5 diameter cardiovascular stent is coated using the methods described herein. The stent is mounted to the balloon of a catheter, resulting in a maximum outer diameter (profile) of the mounted (crimped) stent of 1.18 mm.

A 4.0 diameter cardiovascular stent is coated using the methods described herein. The stent is mounted to the balloon of a catheter resulting in a maximum outer diameter (profile) of the mounted (crimped) stent of 1.25 mm.

The two systems are delivered concurrently, each to a location in the patient's coronary arterial system (which may be separate arteries or the same artery), by advancing the first system through a 7F guiding catheter to the patient's coronary arterial system at the same time as a second system is advanced through the same 7F guiding catheter to the patient's coronary arterial system. The first system is then advanced to a first location in the arterial system to be stented, and the stent is delivered to such location. The second system is then advanced to a second location in the arterial system to be stented, and the stent is delivered to such location. Both systems are then removed from the patient's vasculature.

Example 17—Two 3.0×15 Stent Systems Through a 7F Guiding Catheter

Two 3.0 diameter×15 mm length cardiovascular stents were coated using the methods described herein. The stents were mounted to balloons of two catheters, wherein the balloon comprised polyamide, and the mounted stent maximum outer diameters (profiles) were both 1.12 mm.

The two systems were delivered concurrently, each to a location in the patient's coronary arterial system by advancing the first system through a 7F guiding catheter to the patient's coronary arterial system at the same time as a second system was advanced through the same 7F guiding catheter to the patient's coronary arterial system. The first system was then advanced to a first location in the arterial system to be stented, and the stent was delivered to such location. The second system was then advanced to a second location in the arterial system to be stented, and the stent was delivered to such location. Both systems were then removed from the patient's vasculature.

Example 18—Lubricity

At least one of the following is made:
A 2.25 diameter cardiovascular stent is coated using the methods described herein. The stent is mounted to the balloon of a catheter resulting in a maximum outer diameter (profile) of the mounted (crimped) stent of 1.06 mm.
A 2.5 diameter cardiovascular stent is coated using the methods described herein. The stent is mounted to the balloon of a catheter, resulting in a maximum outer diameter (profile) of the mounted (crimped) stent of 1.09 mm.
A 2.75 diameter cardiovascular stent is coated using the methods described herein. The stent is mounted to the balloon of a catheter, resulting in a maximum outer diameter (profile) of the mounted (crimped) stent of 1.11 mm.
A 3.0 diameter cardiovascular stent is coated using the methods described herein. The stent is mounted to the balloon of a catheter, resulting in a maximum outer diameter (profile) of the mounted (crimped) stent of 1.12 mm.
A 3.5 diameter cardiovascular stent is coated using the methods described herein. The stent is mounted to the balloon of a catheter, resulting in a maximum outer diameter (profile) of the mounted (crimped) stent of 1.18 mm.
A 4.0 diameter cardiovascular stent is coated using the methods described herein. The stent is mounted to the balloon of a catheter resulting in a maximum outer diameter (profile) of the mounted (crimped) stent of 1.25 mm.
Lubricity is tested according to US Patent Application 20080292776, which is incorporated here by reference in its entirety.

Example 19—Surface Hardness

A cardiovascular stent is coated using the methods described herein. Surface Hardness (Hf) of the stent coating is tested by Nanoindentation Test 1 using Tapping AFM, as described in Bruno A. Latella, Bee K. Gan, Christophe J. Barbé, and David J. Cassidy "Nanoindentation hardness, Young's modulus, and creep behavior of organic-inorganic silica-based sol-gel thin films on copper" J. Mater. Res., Vol. 23, No. 9: 2357-2365, September 2008, which is incorporated here by reference in its entirety.

Example 20—Surface Hardness—Wetted

A cardiovascular stent is coated using the methods described herein. Surface Hardness (Hf) of the wetted stent coating is tested by Nanoindentation Test 1 using Tapping AFM, as described in Bruno A. Latella, Bee K. Gan, Christophe J. Barbé, and David J. Cassidy "Nanoindentation hardness, Young's modulus, and creep behavior of organic-inorganic silica-based sol-gel thin films on copper" J. Mater. Res., Vol. 23, No. 9: 2357-2365, September 2008, which is incorporated here by reference in its entirety. In order to wet the stent coating prior to testing, the coating (or coated stent) is wetted by immersing the coated stent in a saline solution for about 5 minutes.

Example 21—Surface Hardness—Wetted

A cardiovascular stent is coated using the methods described herein. Surface Hardness (Hf) of the wetted stent coating is tested by Nanoindentation Test 1 using Tapping AFM, as described in Bruno A. Latella, Bee K. Gan, Christophe J. Barbé, and David J. Cassidy "Nanoindentation hardness, Young's modulus, and creep behavior of organic-inorganic silica-based sol-gel thin films on copper" J. Mater. Res., Vol. 23, No. 9: 2357-2365, September 2008, which is incorporated here by reference in its entirety. In order to wet the stent coating prior to testing, the coating (or coated stent) is wetted by immersing the coated stent in a saline solution for about 4 hours.

The foregoing is illustrative of the present invention, and is not to be construed as limiting thereof. While embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The invention claimed is:
1. A stent delivery system comprising:
 a. an elongate member having an inflation lumen and a guidewire lumen therein;
 b. a balloon having an interior that is in fluid communication with the inflation lumen; and
 c. a stent comprising a bioabsorbable polymer coating, consisting essentially of a hydrophilic polymer comprising at least one of PLGA, a PLGA copolymer, poly(glycolide) (PGA), poly(l-lactide) (LPLA), poly (dl-lactide) (DLPLA), poly(e-caprolactone) (PCL), poly(dioxolane) (PDO), PGA-TMC, 85/15 p(dl-lactide-co-glycolide) (PLPLG) 75/25 DLPL, 65/35 (DLPLG), 50/50 DLPLG, poly(trimethylcarbonate) (TMC), and poly(1,3-bis-p-(carboxyphenoxy)propane-co-sebacic acid) (p(CPP:SA), with a pharmaceutical agent dispersed within the polymer, the stent mounted on the balloon,
 wherein when at least a portion of the stent system that includes the mounted stent is tested using Lubricity Test 1, the lubricity is at most 7 g, wherein the polymer coating is at most 20 micrometers in thickness and provides the lubricity.
2. The stent delivery system of claim 1, wherein for a stent of about 2.25 mm in diameter to about 4.0 mm in diameter by about 9 mm to about 30 mm in length in an expanded state, a stent system trackability expressed as a mean force over the track length is at most 0.5 Newtons, wherein the polymer coating is at most 20 micrometers in thickness.
3. The stent delivery system of claim 2, wherein stent system trackability is tested according to at least one of: Tortuosity test 1 and Tortuosity test 2.

4. The stent delivery system of claim 2,
in which the balloon comprises a polymer, and
in which the stent mounted on the balloon has a crossing profile of at most 1.12 mm.

5. The stent delivery system of claim 2, wherein the stent system trackability is achieved with at least one of: at most 5% coating delamination, at most 10% coating delamination, at most 15% coating delamination, at most 20% coating delamination, at most 5% coating cracking, at most 10% coating cracking, at most 15% coating cracking, and at most 20% coating cracking.

6. The stent delivery system of claim 1, wherein a stent of about 2.25 mm in diameter to about 4.0 mm in diameter by about 9 mm to about 30 mm in length in an expanded state has a stent system pushability (($F_{dist}/F_{prox}$)×100%) of at most 18%, wherein the polymer coating is at most 20 micrometers in thickness.

7. The stent delivery system of claim 6, wherein the stent system pushability is measured according to Tortuosity Test 2.

8. The stent delivery system of claim 6,
in which the balloon comprises a polymer, and
in which the stent mounted on the balloon has a crossing profile selected from the group consisting of at most 1.06 mm for a 2.25 diameter balloon, at most 1.09 mm for a 2.5 diameter balloon, at most 1.11 mm for a 2.75 diameter balloon, at most 1.12 mm for a 3.0 diameter balloon, at most 1.18 mm for a 3.5 diameter balloon, and at most 1.35 mm for a 4.0 diameter balloon.

9. The stent delivery system of claim 6, wherein the stent system pushability is achieved with at least one of: at most 5% coating delamination, at most 10% coating delamination, at most 15% coating delamination, at most 20% coating delamination, at most 5% coating cracking, at most 10% coating cracking, at most 15% coating cracking, and at most 20% coating cracking.

10. The stent delivery system of claim 1, wherein a stent of about 2.25 mm in diameter to about 4.0 mm in diameter by about 9 mm to about 30 mm in length in an expanded state has a stent system crossability measured as mean cross force of less than 0.03 Newtons, wherein the polymer coating is at most 20 micrometers in thickness.

11. The stent delivery system of claim 10, wherein the stent system crossability is measured according to at least one of: tortuosity test 1 and tortuosity test 2.

12. The stent delivery system of claim 10,
in which the balloon comprises a polymer, and
in which the stent mounted on the balloon has a crossing profile selected from the group consisting of at most 1.06 mm for a 2.25 diameter balloon, at most 1.09 mm for a 2.5 diameter balloon, at most 1.11 mm for a 2.75 diameter balloon, at most 1.12 mm for a 3.0 diameter balloon, at most 1.18 mm for a 3.5 diameter balloon, and at most 1.35 mm for a 4.0 diameter balloon.

13. The stent delivery system of claim 10, wherein the stent system crossability is at most 0.1 Newton expressed as peak cross force.

14. The stent delivery system of claim 10, wherein the stent system crossability is achieved with at least one of: at most 5% coating delamination, at most 10% coating delamination, at most 15% coating delamination, at most 20% coating delamination, at most 5% coating cracking, at most 10% coating cracking, at most 15% coating cracking, and at most 20% coating cracking.

15. The stent delivery system of claim 1, wherein when tested using Lubricity Test 1, at least the portion of the stent system that includes the mounted stent has a lubricity of at most about 6 g, or at most about 5 g.

16. The stent delivery system of claim 1,
in which the balloon comprises a polymer, and
in which the stent mounted on the balloon has a crossing profile selected from the group consisting of at most 1.06 mm for a 2.25 diameter balloon, at most 1.09 mm for a 2.5 diameter balloon, at most 1.11 mm for a 2.75 diameter balloon, at most 1.12 mm for a 3.0 diameter balloon, at most 1.18 mm for a 3.5 diameter balloon, and at most 1.35 mm for a 4.0 diameter balloon.

* * * * *